United States Patent
Kohn et al.

(10) Patent No.: US 10,760,102 B2
(45) Date of Patent: Sep. 1, 2020

(54) PROCESS FOR PRODUCING LOWER ALKYL ALCOHOLS FROM CELLULOSIC BIOMASS USING MICROORGANISMS

(71) Applicants: Richard Allen Kohn, Columbia, MD (US); Seon-Woo Kim, Columbia, MD (US)

(72) Inventors: Richard Allen Kohn, Columbia, MD (US); Seon-Woo Kim, Columbia, MD (US)

( * ) Notice: Subject to any disclaimer, the term of this patent is extended or adjusted under 35 U.S.C. 154(b) by 641 days.

(21) Appl. No.: 14/845,925

(22) Filed: Sep. 4, 2015

(65) Prior Publication Data

US 2016/0017378 A1 Jan. 21, 2016

Related U.S. Application Data

(62) Division of application No. 12/385,215, filed on Apr. 1, 2009, now Pat. No. 9,193,979.

(60) Provisional application No. 61/113,337, filed on Nov. 11, 2008.

(51) Int. Cl.
| | |
|---|---|
| *C12P 7/10* | (2006.01) |
| *C12P 7/04* | (2006.01) |
| *C12P 7/06* | (2006.01) |
| *C12P 7/16* | (2006.01) |
| *C12R 1/145* | (2006.01) |
| *C12R 1/44* | (2006.01) |
| *C12R 1/46* | (2006.01) |
| *A23K 10/12* | (2016.01) |

(52) U.S. Cl.
CPC ............... *C12P 7/10* (2013.01); *A23K 10/12* (2016.05); *C12P 7/04* (2013.01); *C12P 7/065* (2013.01); *C12P 7/16* (2013.01); *C12R 1/145* (2013.01); *C12R 1/44* (2013.01); *C12R 1/46* (2013.01); *C12P 2201/00* (2013.01); *Y02E 50/10* (2013.01); *Y02E 50/16* (2013.01); *Y02E 50/17* (2013.01)

(58) Field of Classification Search
CPC .... C12P 7/10; C12P 7/04; C12P 7/065; C12P 7/16; C12R 1/145; C12R 1/44; C12R 1/46; Y02E 50/10; Y02E 50/16; Y02E 50/17
See application file for complete search history.

(56) References Cited

U.S. PATENT DOCUMENTS

| | | | |
|---|---|---|---|
| 4,110,475 A | 8/1978 | Singer | |
| 4,443,542 A * | 4/1984 | Hayashida | C12P 7/16 435/160 |
| 5,620,877 A | 4/1997 | Farone et al. | |
| 2003/0077771 A1 | 4/2003 | Verser et al. | |
| 2003/0203454 A1 | 10/2003 | Chotani et al. | |
| 2004/0157301 A1 | 8/2004 | Chotani et al. | |
| 2005/0100996 A1 | 5/2005 | Lantero et al. | |
| 2006/0011491 A1 | 1/2006 | Logan | |
| 2006/0024801 A1 | 2/2006 | Holtzapple et al. | |
| 2006/0084156 A1 | 4/2006 | Lantero et al. | |
| 2007/0178569 A1 | 8/2007 | Leschine et al. | |
| 2007/0275438 A1 | 11/2007 | David | |
| 2008/0193989 A1 | 8/2008 | Verser et al. | |
| 2009/0017513 A1 | 1/2009 | Bell et al. | |
| 2009/0023192 A1 | 1/2009 | Verser et al. | |
| 2009/0035848 A1 | 2/2009 | Hickey | |
| 2009/0068714 A1 | 3/2009 | Lescnine et al. | |

FOREIGN PATENT DOCUMENTS

| | | |
|---|---|---|
| WO | WO2006119052 A1 | 11/2006 |
| WO | WO2007130984 A1 | 11/2007 |

OTHER PUBLICATIONS

Peng, et al, Sheng Wu Gong Cheng Xue Bao, 24(6),Jun. 2008, pp. 1117-1120 (pubmed abstract only), (Year: 2008).*
Alper, H et al. "Engineering Yeast Transcription Machinery for Improved Ethanol Tolerance and Production" Science, Dec. 8, 2006, 314, 1565-1568.
Grosz, R and Stephanopoulos, G, Biotechnology and Bioengineering, 36(10), Dec. 5, 1990,pp. 1006-1019.
Grosz, R and Stephanopoulos, G, Biotechnology and Bioengineering,36(10), Dec. 5, 1990,pp. 1020-1029.
Grosz, R and Stephanopoulos, G, Biotechnology and Bioengineering,36(10), Dec. 5, 1990,pp. 1030-1040.
Goho, A. "Arnold, Frances: TR10: Cellulolytic Enzymes" MIT Technology Review, published on line Apr. 15, 2008, pp. 1-2 (printed on 4 pages).
Wang, DIC, Avgerinos, GC, Biocic, I, Wang S-D, Fang, H-Y, and Young, FE "Ethanol from Cellulosic Biomass" Philosophical Transactions of the Royal Society of London. Series B, Biological Sciences, Jan. 26, 1983, 300(1100), pp. 323-333.
Benat, I M; Nigam, P; Singh, D; Marchant, R; McHale, A P "Review: Ethanol Production at Elevated Temperatures and Alcohol Concentrations: Part I—Yeasts in General" World Journal of Microbiology & Biotechnology, 1998, 14, pp. 809-821.
Sudha Rani, K. and Seenayya, G. "High Ethanol Tolerance of New Isolates of Clostridium thermocellum strains SS21 end SS22" World Journal of Microbiology & Biotechnology, 1999, 15, pp. 173-178.
Zayed, G.; Meyer, 0. "The Single-Batch Bioconversion of Wheat Straw to Ethanol Employing the Fungus *Trichoderma viride* and the Yeast *Pachysolen tannophylus*" Applied Microbiology and Biotechnology, 1996, 45(4), pp. 551-555.
Holtzapple, M. "Conversion of Waste Biomass to Animal Feed, Chemicals, and Fuels" 1996 Green Chemistry Academic Award, USEPA, archived online <URL:http://www.epa.gov/greenchemistry/pubs/pgcc/winners/aa96.html>, 1996, 1 page.

(Continued)

*Primary Examiner* — Aaron J Kosar

(57) ABSTRACT

At least one isolated microorganism, which converts at least 10% by weight, and preferably 50% by weight, of cellulosic biomass to a lower alkyl alcohol by direct digestion, and which produces at least 4% by volume of the lower alkyl alcohol in an aqueous-based digestion medium.

21 Claims, 12 Drawing Sheets

Specification includes a Sequence Listing.

(56) References Cited

OTHER PUBLICATIONS

Icyarris, L. "Microbes Produce Fuels Directly from Biomass" News Release: Lawrence Berkeley National Laboratory , Jan. 27, 2010, 3 pages.
Cocconcelli, PS et al "Plasmid transformation of Ruminococcus albus by means of high-voltage electroporation." FEMS Microbial Lett, Jul. 15, 1992, 73(3),pp. 203-207(Abstract Only).

* cited by examiner

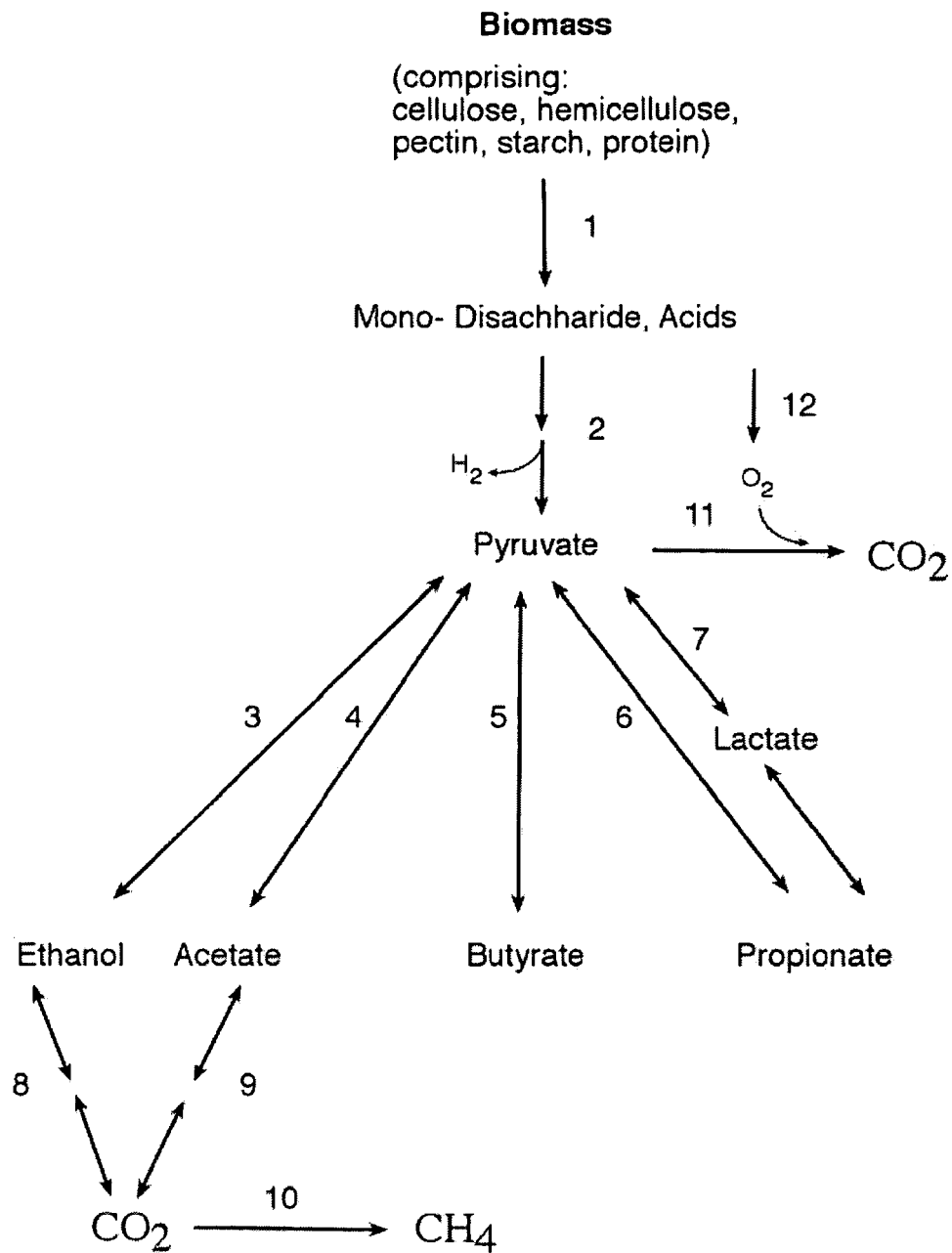
Figure 1. Optional pathways for digestion and conversion of complex carbohydrate. The means to control these pathways is an aspect of the present invention. Hydrogen flows are not shown but are a major aspect of the control.

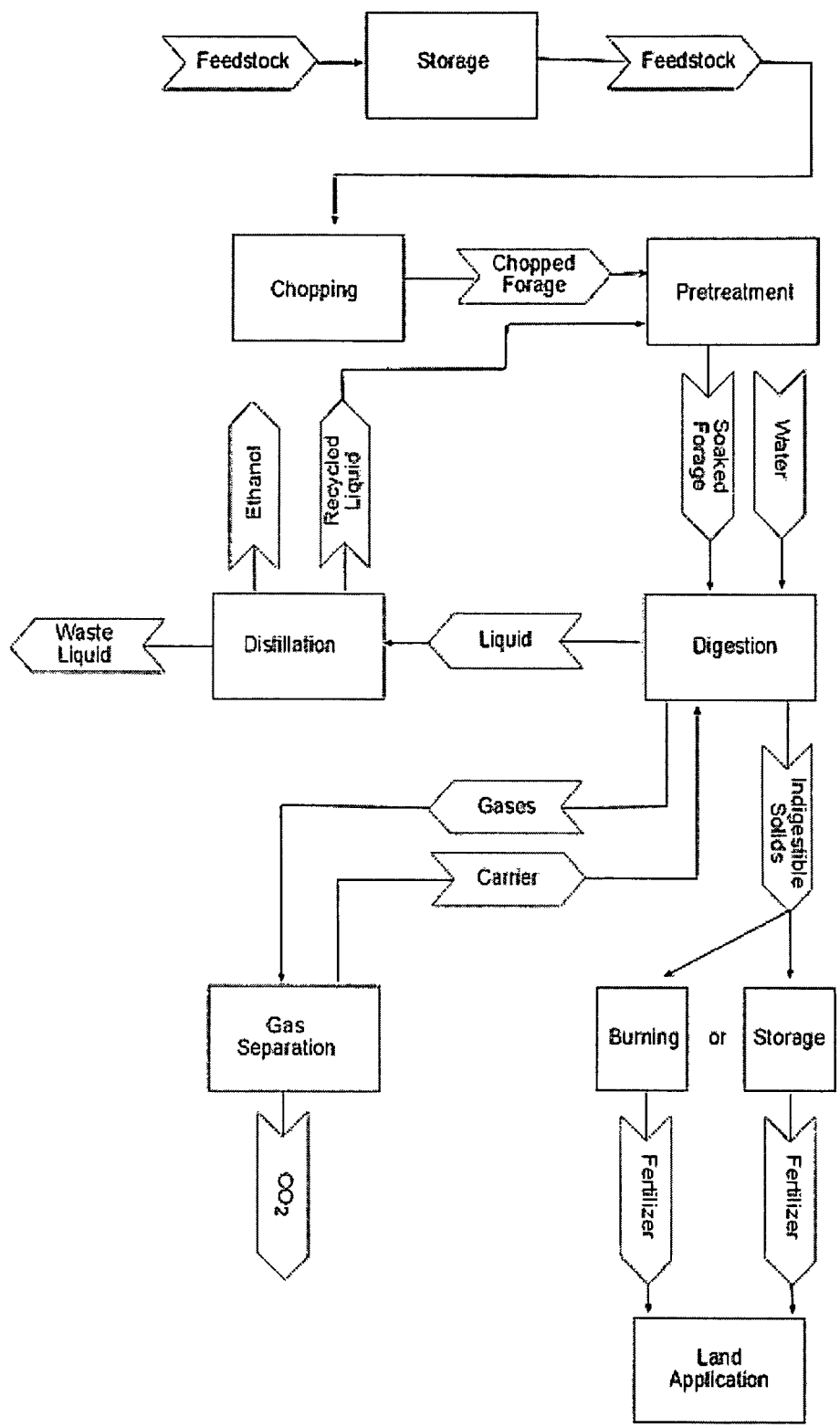
Figure 2. Material flow diagram for a process to produce ethanol from cellulosic biomass.

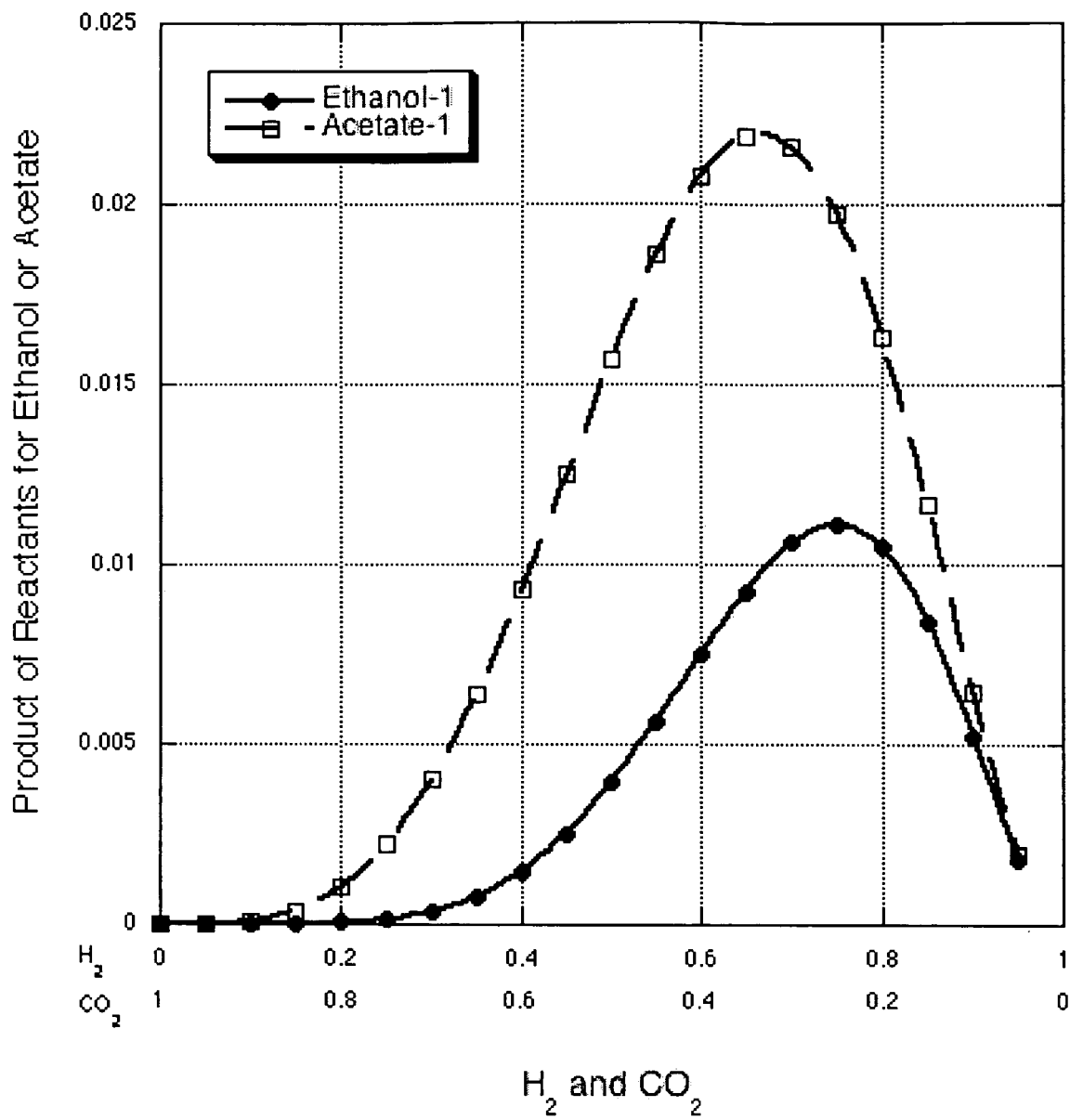
Figure 3. The product of reactant gas concentrations (atmospheres) for reactants to make ethanol or acetic acid where partial pressure of hydrogen ($H_2$) increases with constant total gas pressure of 1 atm comprising $H_2$ and carbon dioxide ($CO_2$) gas.

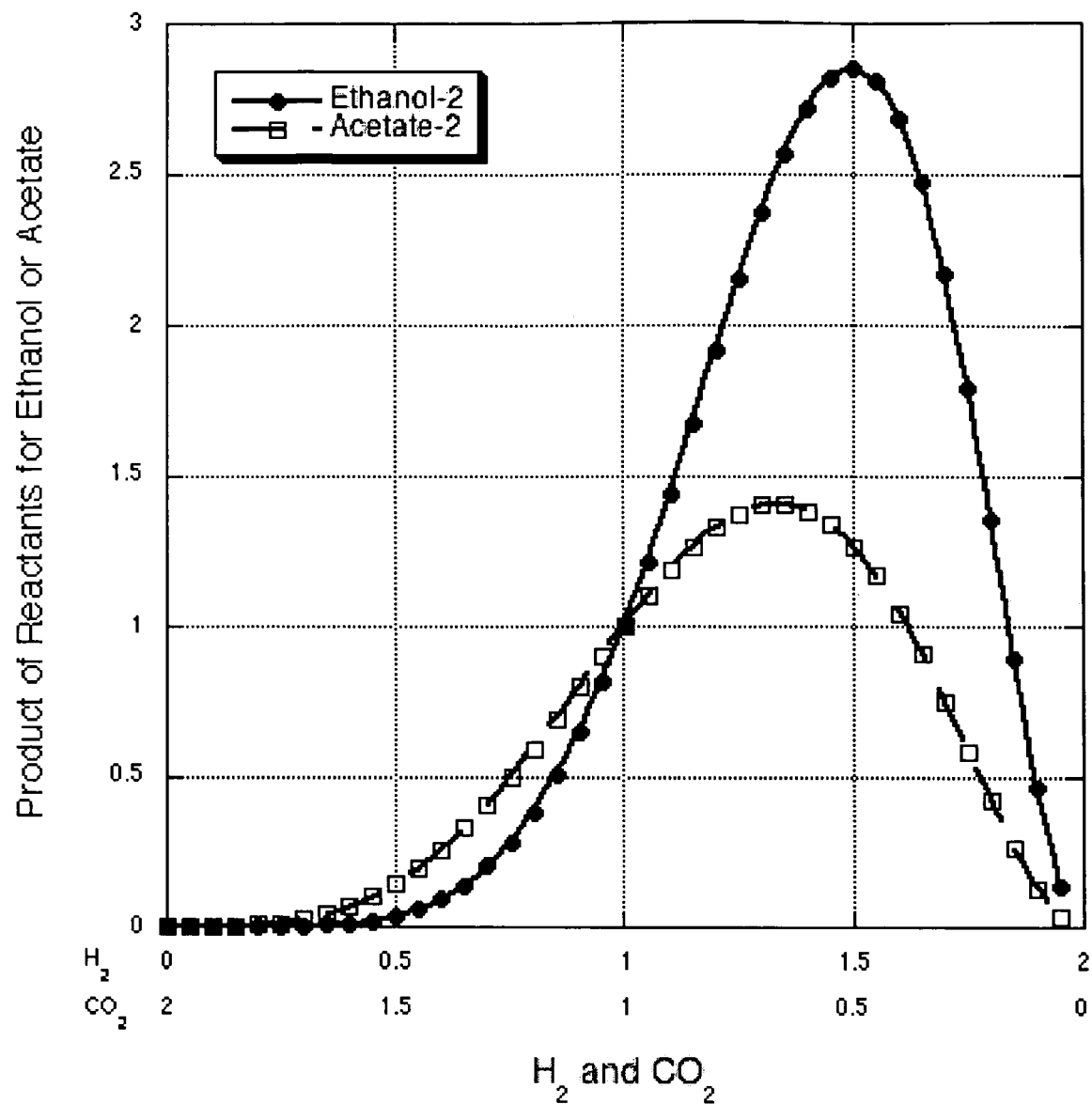
Figure 4. The product of reactant gas concentrations (atmospheres) for reactants to make ethanol or acetic acid where partial pressure of hydrogen ($H_2$) increases with constant total gas pressure of 2 atm comprising $H_2$ and carbon dioxide ($CO_2$) gas.

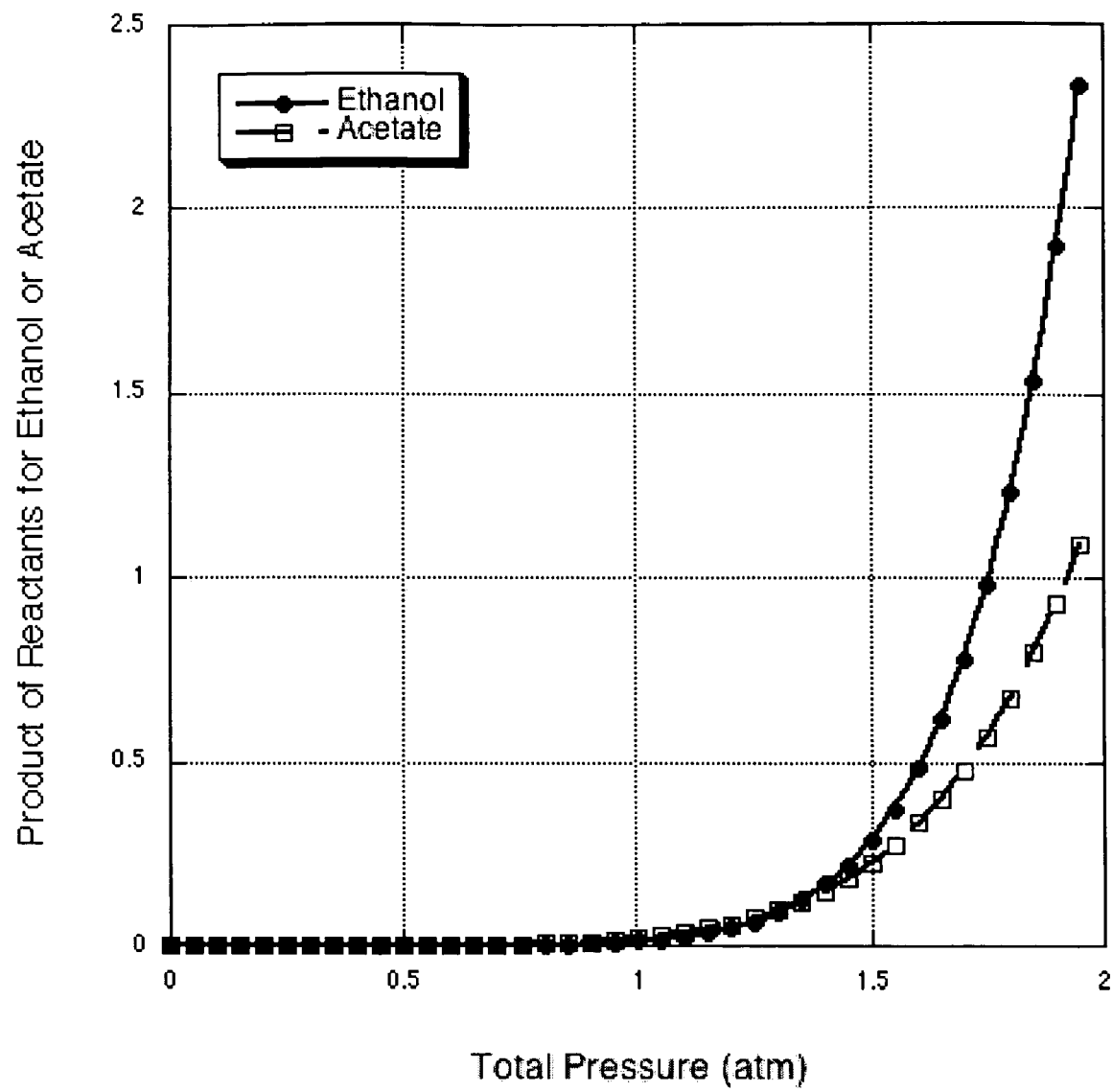
Figure 5. The product of reactant gas concentrations (atmospheres) for reactants to make ethanol or acetic acid where total pressure of all gases is increased and gases are comprised of a constant ratio of 75% $H_2$ and 25% carbon dioxide ($CO_2$).

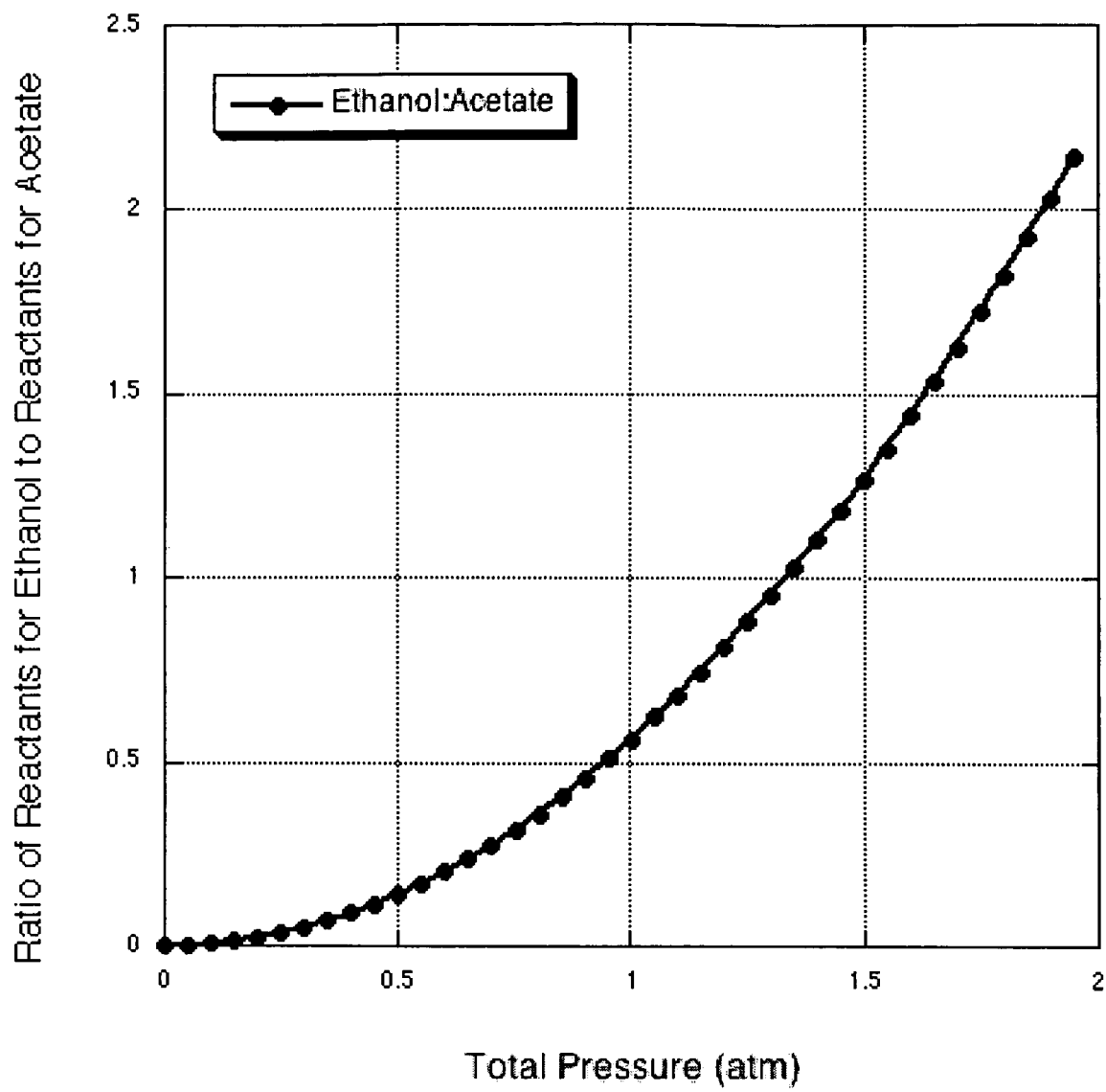
Figure 6. The ratio of the product of reactant gas concentrations (atmospheres) for reactants to make ethanol to the product of reactant gas concentrations to make acetic acid where total pressure of all gases is increased and gases are comprised of a constant ratio of 75% $H_2$ and 25% carbon dioxide ($CO_2$).

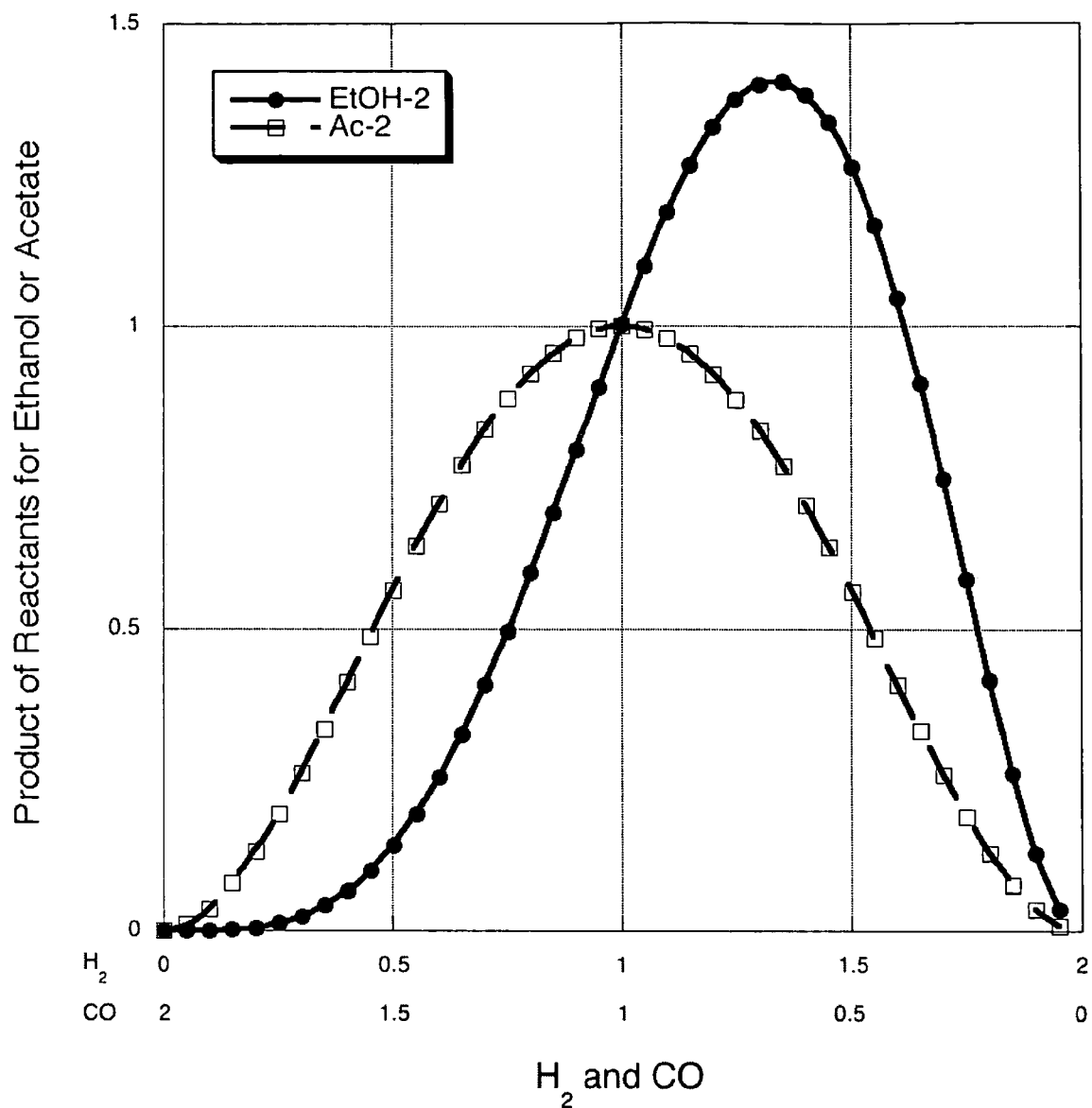
Figure 7. The product of reactant gas concentrations for reactants to make ethanol or acetic acid where partial pressure of hydrogen ($H_2$) increases with constant pressure of 1 atm comprising $H_2$ and carbon monoxide (CO) gas.

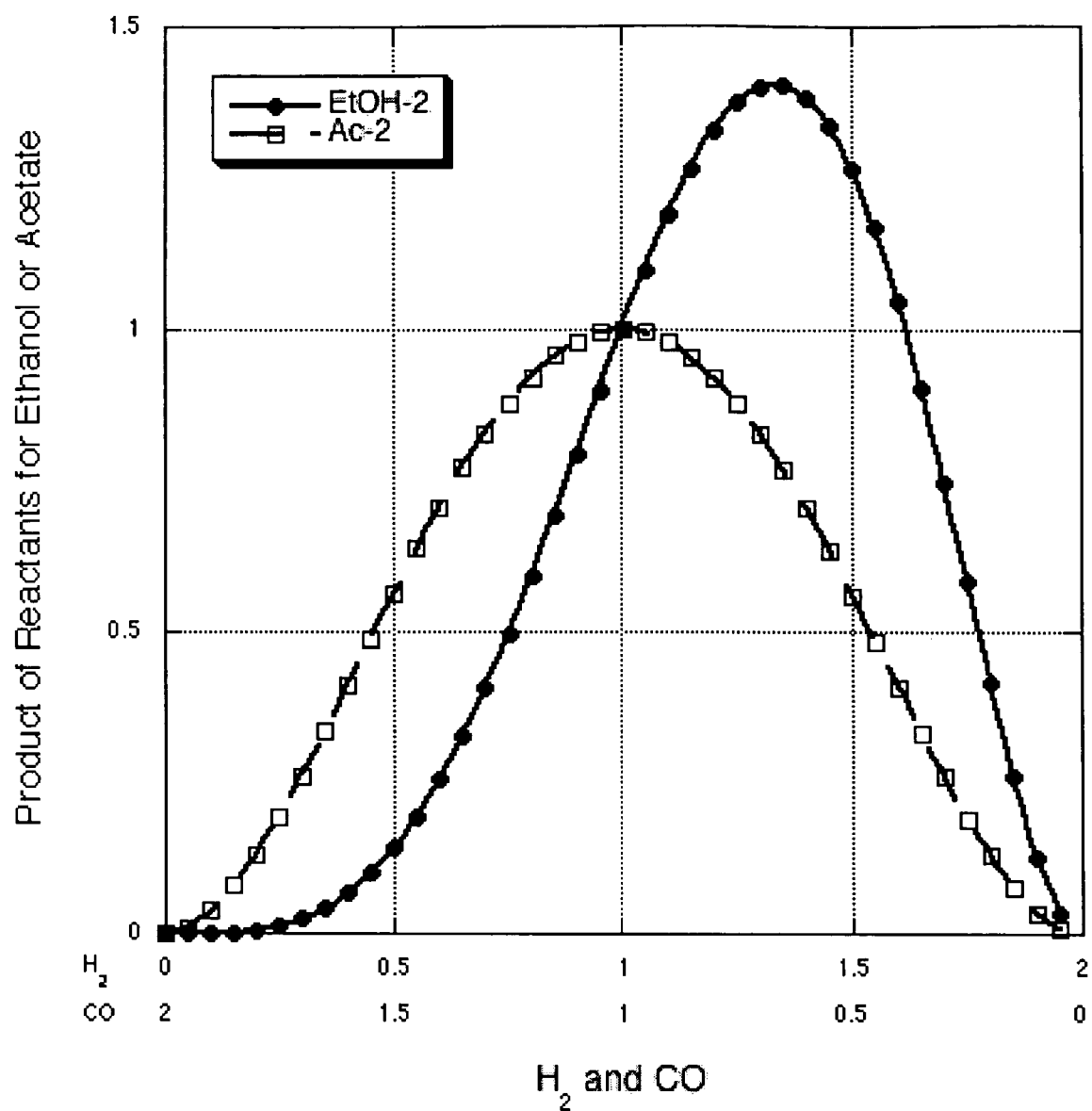
Figure 8. The product of reactant gas concentrations (atmospheres) for reactants to make ethanol or acetic acid where partial pressure of hydrogen ($H_2$) increases with constant total gas pressure of 1 atm comprising $H_2$ and carbon monoxide (CO) gas.

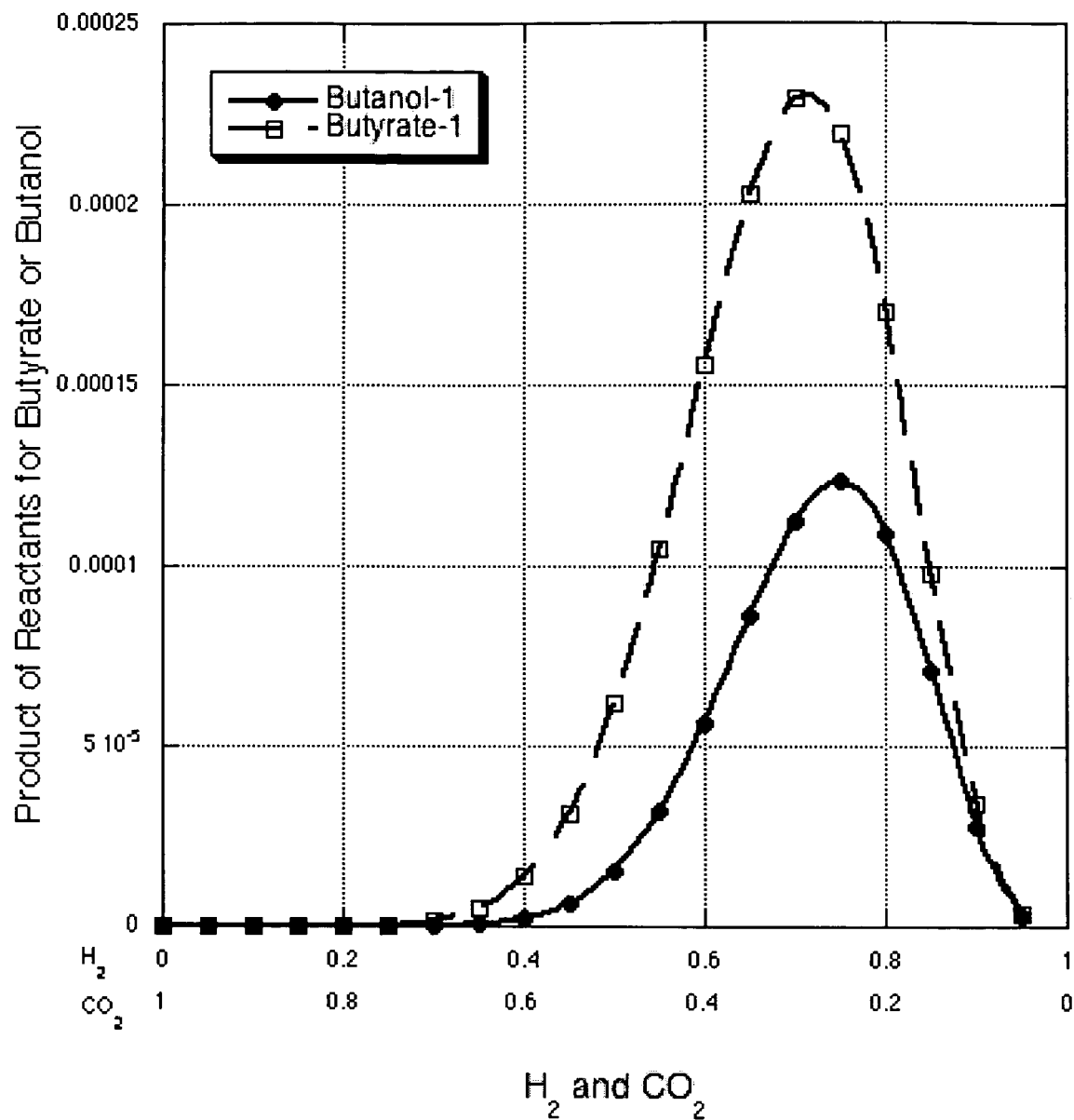
Figure 9. The product of reactant gas concentrations (atmospheres) for reactants to make butanol or butyrate where partial pressure of hydrogen ($H_2$) increases with constant total gas pressure of 1 atm comprising $H_2$ and carbon dioxide ($CO_2$) gas.

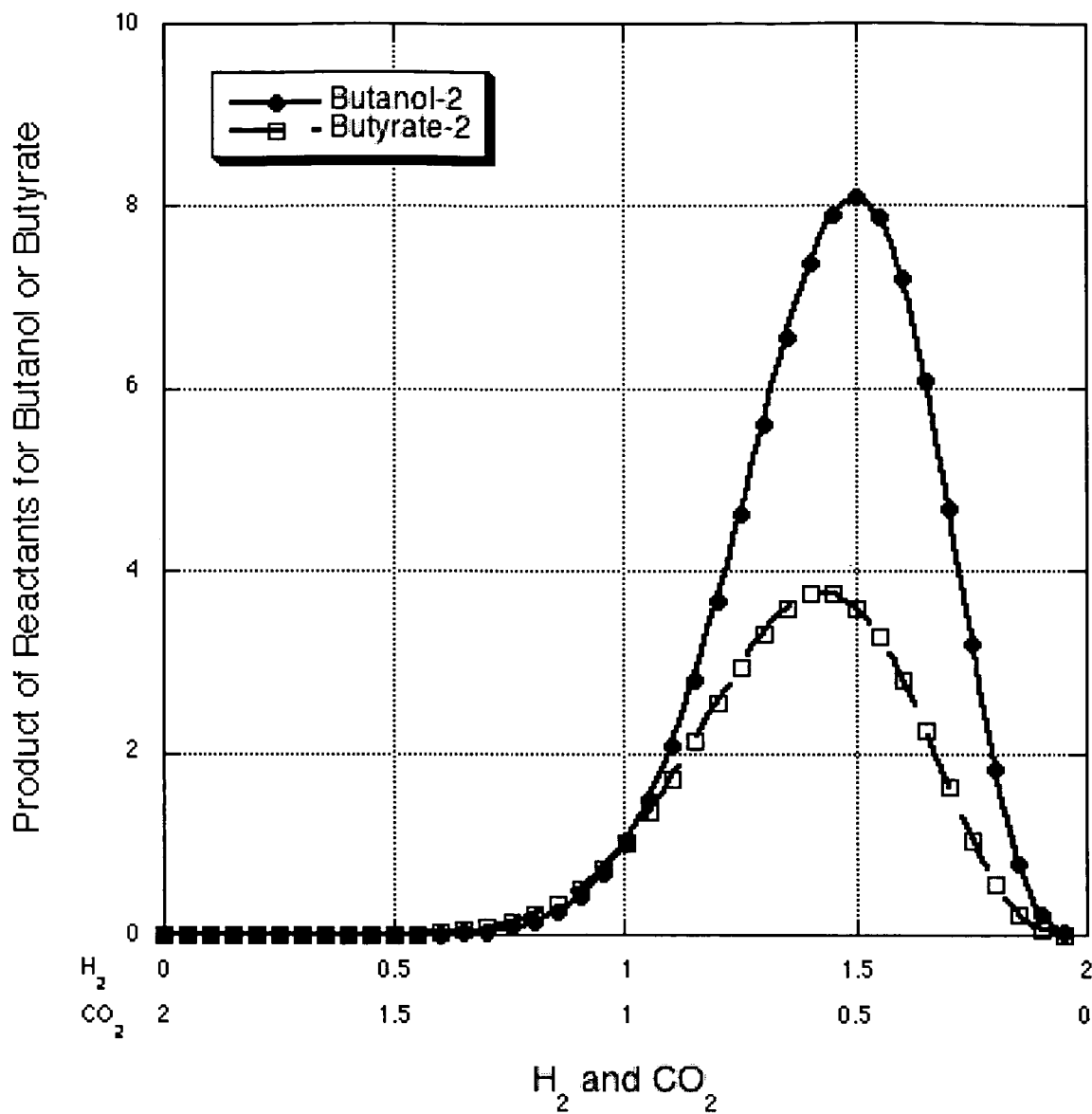
Figure 10. The product of reactant gas concentrations (atmospheres) for reactants to make butanol or butyrate where partial pressure of hydrogen ($H_2$) increases with constant total gas pressure of 2 atm comprising $H_2$ and carbon dioxide ($CO_2$) gas.

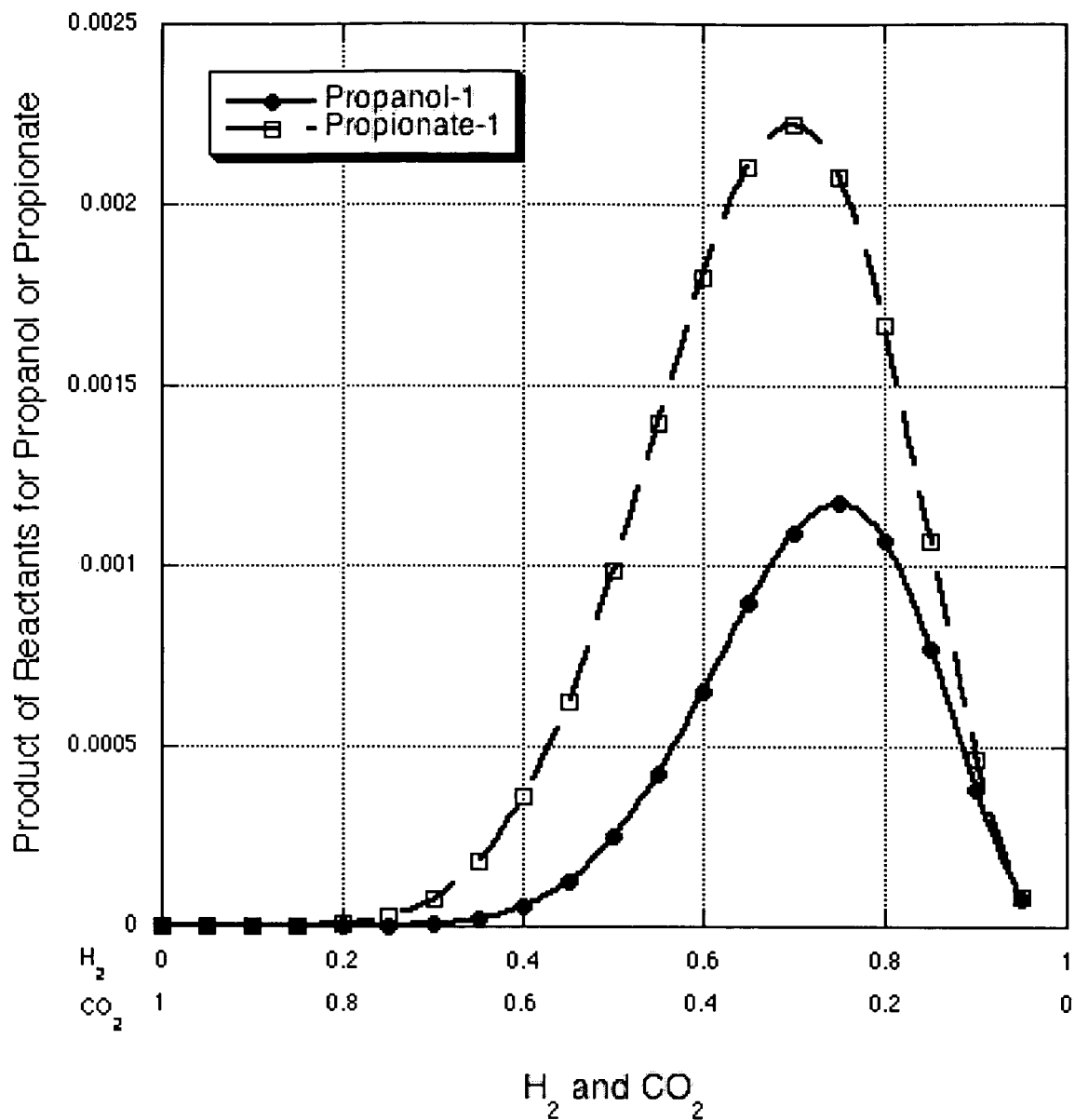
Figure 11. The product of reactant gas concentrations (atmospheres) for reactants to make propanol or propionate where partial pressure of hydrogen ($H_2$) increases with constant total gas pressure of 1 atm comprising $H_2$ and carbon dioxide ($CO_2$) gas.

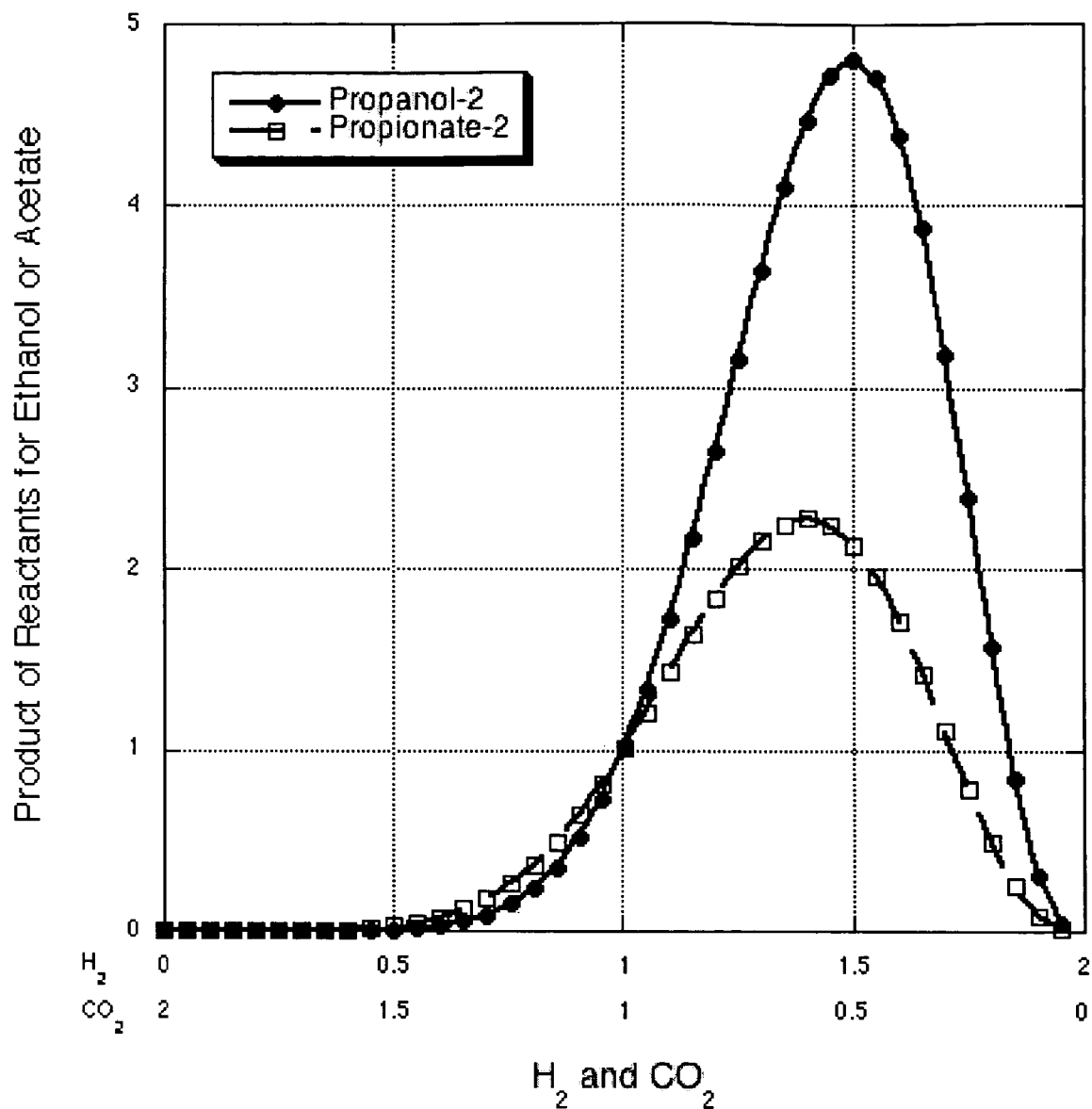
Figure 12. The product of reactant gas concentrations (atmospheres) for reactants to make propanol or propionate where partial pressure of hydrogen ($H_2$) increases with constant total gas pressure of 2 atm comprising $H_2$ and carbon dioxide ($CO_2$) gas.

PROCESS FOR PRODUCING LOWER ALKYL ALCOHOLS FROM CELLULOSIC BIOMASS USING MICROORGANISMS

CROSS-REFERENCE TO RELATED APPLICATIONS

This application is a division of U.S. patent application Ser. No. 12/385,215 filed on Apr. 1, 2009; and it claims priority to U.S. provisional application No. 61/113,337, filed on Nov. 11, 2008.

BACKGROUND OF THE INVENTION

Field of the Invention

The present invention relates to a process for producing lower alkyl alcohols, such as ethanol, from cellulosic biomass using primarily anaerobic microorganisms under thermodynamically favorable conditions therefor; and to anaerobic microorganisms that produce lower alkyl alcohols, such as ethanol, from cellulosic biomass and which microorganisms are tolerant to the lower alkyl alcohols produced.

Description of the Background

The U.S. patent application Ser. No. 12/000,856, filed on Dec. 18, 2007; and U.S. Provisional Application No. 60/870,441, filed on Dec. 18, 2006, are incorporated herein by reference in their entirety.

Currently most ethanol fuel produced in the U.S. is made from corn grain, a feed stuff. Further, even if all the corn grain produced in the U.S. were converted to ethanol, it would only supply about 15% of our current transportation fuel needs in replacing that amount of petroleum usage. Thus, there is a pressing need to produce fuel ethanol from cellulosic plant fiber instead. If ethanol could be inexpensively produced from sources other than corn grain, waste biomass like leaves; paper; manure; and wood or wood byproducts, for example, further inroads into replacing petroleum usage could be made. Cellulosic biomass can be grown on marginal land and in greater yields than grain crops and, thus, offers the promise of high yield based on input. Eventually, it is likely that the U.S. could use up to a billion tons of such biomass per year.

Presently, however, the available technologies for producing so-called cellulosic ethanol are prohibitively expensive and, thus, industrially unfeasible. Moreover, competition for available corn grain between use in ethanol fuel and in producing corn-based food stuffs has led to a large rise in the price of such food stuffs for consumers.

There are three processes generally available for the production of ethanol from plant fiber, also called plant cell wall, which contains cellulose, hemicelluloses, pectin, and lignin. One process is called physical conversion where biomass is heated to high temperatures, such as 650° F., in the absence of oxygen. The biomass is degraded to carbon monoxide (CO) and hydrogen ($H_2$), and subsequently these gases are converted to ethanol by a catalytic or microbial process. Unfortunately, this process involves substantial facility costs and is not considered cost effective for commercial use.

A second approach is biochemical conversion which entails boiling the biomass in caustic acids or other chemicals to unravel the cellulose and hemicelluloses. The residue is neutralized and conditioned and subjected to cellulolytic enzymes to release sugars. The glucose released is fermented by yeast to ethanol, and the 5-carbon sugars are separated and converted to ethanol by a different microorganism.

A third approach to producing cellulosic ethanol would be to use living microorganisms that could digest cellulose, hemicelluloses and pectins with conversion to ethanol. This approach might, in theory, be the least expensive approach because it would not require the use of harsh chemicals or high temperatures and would use fewer process steps with fermentation than would the two approaches described above. Although this approach has been considered for over twenty years, it has, unfortunately, not been used as it is only feasible if there is a microorganism or mixed culture of microorganisms that can readily digest cellulose and hemicellulose, and which, preferably, convert a significant part of the carbohydrate to ethanol. Further, the preferred microorganisms must also be tolerant to relatively high ethanol concentrations, i.e., at least about 3-4% by volume, and preferably in excess of 5% by volume, so that they may be used to digest considerable carbohydrate to produce ethanol at high enough concentration to decrease the cost of distillation.

Currently, microorganisms for effecting this process in a cost effective manner are unknown. Microorganisms are known which can readily digest cellulosic biomass to produce organic acids, but not ethanol. Further, although microorganisms are known which produce trace amounts of ethanol along with acetic acid, these microorganisms are intolerant to ethanol concentrations exceeding a small amount of media volume of ethanol which renders separation of ethanol from aqueous media cost prohibitive. Ethanol tolerant microorganisms not only grow in relatively high ethanol concentrations, however, it would be even more advantageous for such microorganisms to be able to grow from the energy they capture by producing more ethanol. Moreover, the preferred conditions for fiber digestion (e.g. neutral pH) differ from the preferred conditions for ethanol production (e.g. acidic pH) within existing microorganisms.

The conventional wisdom among scientists is that there is little reason to continue pursuing efforts at isolating naturally-occurring microorganisms for cellulosic ethanol production. In fact, the US Department of Energy (DOE) Roadmap for biofuel production (DOE, 2006) also emphasizes similar points and reinforces this conventional wisdom. The grant programs by the DOE and US Department of Agriculture (USDA) encourage modern metabolic engineering and discourage attempts to find and isolate suitable naturally-occurring microorganisms for the production of ethanol.

Thus, a need exists for a plausible method for producing ethanol, as well as other lower alkyl alcohols, from cellulosic biomass using microorganisms and fermentative digestion, thus avoiding the use of costly process steps to produce the ethanol or other lower alkyl alcohols. Yet, the possibility of finding naturally-occurring microorganisms for this task has been dismissed for the most part.

SUMMARY OF THE INVENTION

Accordingly, the present invention provides a method of producing lower alkyl alcohols, such as ethanol, from plant fiber and other biomass using naturally-occurring microorganisms.

It is, moreover, a further object of the present invention to provide naturally-occurring microorganisms for producing lower alkyl alcohols, such as ethanol, from plant fiber and other biomass.

It is also an object of the present invention to provide a method for screening for microorganisms that are capable of producing high yields of ethanol or other lower alkyl alcohols from fermentation of cellulosic biomass.

It is a further object of the present invention to provide a method for predominantly producing a single lower alkyl alcohol which entails digesting biomass with naturally-occurring microorganisms which produces the single lower alkyl alcohol; and effecting an enrichment stage in the presence of the single lower alkyl alcohol to promote and favor digestion by one or more naturally-occurring microorganisms that are tolerant to said lower alkyl alcohol.

It is, moreover, an object of the present invention to provide a method for favoring production of ethanol or other lower alkyl alcohols from digestion of biomass containing plant fiber, which comprises digesting sad biomass containing plant fiber under conditions which thermodynamically favor production of ethanol and other lower alkyl alcohols therefor.

Further, it is an object of the present invention to provide a method of digesting cellulosic biomass with one or more microorganisms to produce a lower alkyl alcohol under thermodynamically favorable conditions therefor.

The above objects and others are provided by a method for producing lower alkyl alcohols from biomass containing plant fiber, which entails anaerobically digesting the biomass containing plant fiber with one or more naturally-occurring microorganisms which directly digest the biomass containing plant fiber, and which microorganisms are tolerant to lower alkyl alcohols.

BRIEF DESCRIPTION OF THE DRAWINGS

FIG. 1 schematically illustrates optional pathways for digestion and conversion of complex carbohydrate, which can be controlled in accordance with the present invention.

FIG. 2 represents a material flow diagram for a process for producing ethanol from cellulosic biomass.

FIG. 3 illustrates the relationship between the product of reactant gas concentrations (atmospheres) for reactants to make ethanol or acetic acid for increasing partial pressure of hydrogen ($H_2$) with constant total gas pressure of 1 atm of hydrogen ($H_2$) and carbon dioxide ($CO_2$).

FIG. 4 illustrates the same as FIG. 3, except that the constant total gas pressure is 2 atm.

FIG. 5 illustrates the same as FIG. 3, except that the total pressure of both hydrogen ($H_2$) and carbon dioxide ($CO_2$) are increased, where a constant ratio of 75% $H_2$ and 25% $CO_2$ is used.

FIG. 6 illustrates the relationship of the ratio of the product of reactant gas concentrations (atmospheres) for reactants to make ethanol to the product of reactant gas concentrations to make acetic acid where the total pressure of all gases is increased and gases are at a constant ratio of 75% hydrogen ($H_2$) and 25% carbon dioxide ($CO_2$).

FIG. 7 illustrates the relationship of the product of reactant gas concentrations (atmospheres) for reactants to make ethanol or acetic acid where partial pressure of hydrogen ($H_2$) increases with constant total gas pressure of 1 atm of hydrogen ($H_2$) and carbon monoxide (CO).

FIG. 8 illustrates the relationship of the product of reactant gas concentrations (atmospheres) for reactants to make ethanol or acetic acid where partial pressure of hydrogen ($H_2$) increases with constant total gas pressure of 1 atm. of hydrogen ($H_2$) and carbon monoxide (CO).

FIG. 9 illustrates the product of reactant gas concentrations (atmospheres) for reactants to make butanol or butyrate where partial pressure of hydrogen ($H_2$) increases with constant total gas pressure of 1 atm containing hydrogen ($H_2$) and carbon dioxide ($CO_2$) gas.

FIG. 10 illustrates the product of reactant gas concentrations (atmospheres) for reactants to make butanol or butyrate where partial pressure of hydrogen ($H_2$) increases with constant total gas pressure of 2 atm comprising $H_2$ and carbon dioxide ($CO_2$) gas.

FIG. 11 illustrates the product of reactant gas concentrations (atmospheres) for reactants to make propanol or propionate where partial pressure of hydrogen ($H_2$) increases with constant total gas pressure of 1 atm comprising $H_2$ and carbon dioxide ($CO_2$) gas.

FIG. 12 illustrates the product of reactant gas concentrations (atmospheres) for reactants to make propanol or propionate where partial pressure of hydrogen ($H_2$) increases with constant total gas pressure of 2 atm comprising $H_2$ and carbon dioxide ($CO_2$) gas.

DETAILED DESCRIPTION OF THE PREFERRED EMBODIMENTS

The present invention is based in part, on the application of the second law of thermodynamics, i.e., second law, to biology, in general, and to fermentation, in particular. This law was originally formulated around 1850 by Clausius and Kelvin and, in general, determines when a reaction can proceed spontaneously in a forward direction, or may proceed in a reverse direction. For reactions in which there is a limited amount of reactant (substrate) and a large amount of product, conditions can occur in which the flow of the reaction from reactant to product requires the input of additional energy to overcome the further concentration of product. Occasionally, in biology the product and reactant concentrations are quantified and a determination is made that a reaction can or cannot proceed, and how much energy can be captured if it proceeds. These reactant concentrations are studied in vivo or in vitro.

The present invention applies the second law to a far greater, and, in fact, unprecedented, extent to determine which reaction pathway branches in a system are available, and to predict which products will be formed under a given set of conditions. Thereafter, the reaction system may be manipulated to produce a desired product, such as a lower alkyl alcohol. The reaction system is defined by a total of all of its possible pathways, and the flow in one pathway affects the concentrations and flows in all other pathways. Thus, the present inventors provide a thermodynamic model, by which to manipulate fermentation to favor production of a desired product. The present inventors have determined that in testing this model, in fact, thermodynamics may be used to control what products are made in fermentation. Thus, the present invention provides various methods of digesting cellulosic biomass with one or more microorganisms to produce lower alkyl alcohols under thermodynamically favorable conditions therefor.

One of the surprising aspects of the approach described herein in accordance with the present invention is how little information is needed to accurately model a fermentation system. For example, the rumen has been studied for decades, and those skilled in the art know that different metabolites can be passed from one microorganism to another. Thus, $H_2$ when produced may be exported by acetic acid producing microorganisms, and picked up by methanogens or propionic acid producing microorganisms. Yet, the thermodynamic model doesn't require such information, only the net result of the entire pathway. The present thermodynamic model shows that by increasing $H_2$, the equilibrium shifts toward greater ethanol production (as a sink for $H_2$) compared to acetate production (as faucet for $H_2$).

U.S. Ser. No. 12/000,856 discloses controlling fermentation or enriching for microorganisms by manipulating $H_2$ concentrations by adding, retaining, or recirculating it or by inhibiting its utilization. The effect is understood differently at the single microorganism level. For example, consider a microorganism that can produce acetic acid or ethanol. If the microorganism produces acetic acid, it will have additional $H_2$ available based on the stoichiometry. It may be in the form of NADH and it will need to unload it before it can make more acetic acid. Thus, membrane systems have evolved to transfer the $H_2$ outside of the cell. These systems are called hydrogenases whether they serve to export or import $H_2$ from the media. If there is a high concentration of $H_2$ in the media, the uphill gradient will cost the microorganism more energy to export the $H_2$, and it will be disadvantaged. Normally, the microorganism can only make 1 ATP per ethanol produced, but it can make 2 ATP per acetic acid, so it grows faster when acetic acid production is possible. However, when acetic acid production takes more ATP to export the $H_2$ produced, ethanol production would be favored. Thus, the microorganism itself may shift its metabolism toward higher ethanol production when $H_2$ is present. Many microorganisms may not efficiently control their metabolism that way, and they do not compete well against those that do. In fact, other microorganisms that simply make ethanol survive these high $H_2$ conditions.

These microorganisms may be able to survive normally by exporting ethanol to other microbes that convert it to acetic acid. The present thermodynamic model demonstrates that ethanol was not a normal end product of rumen fermentation because it is not a favored product under normal rumen fermentation conditions, however, it could be made to be favored by altering the end product gases. Thus, these conditions can be maintained to cause the mixed culture to make ethanol, or to allow for the enrichment and isolation of microorganisms from the mixed culture that can make ethanol. The method of selection may seem indirect. The objective is to select against acetic acid production, and the means is to inhibit hydrogenase. However, inhibiting the hydrogenase affects the thermodynamics in the cell, which inhibits acetic acid production.

Increasing $H_2$ in incubation favors microorganisms that use $H_2$ and it disfavors those that depend on releasing it. For example, propionate producers and methanogens or reductive acetogens can all be enriched by increasing $H_2$.

Generally, the present invention contemplates: 1) defining a system as a network of many different potential reactions, 2) thermodynamically analyzing each reaction in the system simultaneously, 3) including living reactions to the system such as genetic selection and mutation, 4) using this analysis to predict the impact of different manipulations and 5) identifying ways to shift the overall system toward desired pathways to produce a metabolite, to enrich for certain functional characteristics among microorganisms, or even to direct evolution of microbial strains.

Thus, the present inventors use thermodynamics to 1) find ways of shifting complex chemical systems, including living systems of which fermentation is an example, toward certain products (e.g. ethanol), 2) select for certain functional types of microbes within this type of complex living system, and 3) direct evolution, wherein evolution is well understood to mean a process involving selection pressure and mutation, which tends to eventually result in the development of microorganisms well suited for their natural environments. The presently disclosed methodologies, however, lead to the development of microorganisms that are particularly well suited for environments not found in nature. Moreover, the conditions used to develop such microorganisms favor rapid development thereof and production of products from the microorganisms in a manner not found in nature.

In simple chemical systems, the difference in Gibbs free energy contained in reactants and products ($\Delta G$) can be calculated based on temperature, concentrations and pressures, and this difference can be used to determine whether or not a reaction can proceed spontaneously in a certain direction. An approach used in an aspect of the present invention applies this analysis to complex chemical systems with multiple competing pathways, and to set up and solve multiple simultaneous equations with each equation representing a different possible pathway. Thus, the approach utilized by the present invention represents a significantly advantageous way of manipulating system pathways to obtain a desired product, in particular, lower alkyl alcohols, such as ethanol, propanol or butanol.

Furthermore, in accordance with the present invention, the complex chemical system may be a living system such as an organism, or in the example in this description, an ecosystem containing many organisms. Thus, using this approach described herein can enable the production of a desired product for a fermentation system, but further it can be used to enrich for or select microorganisms with desired characteristics. Furthermore, the application of the second law of thermodynamics for enrichment and selection effected as part of the present invention can be practiced over many generations, resulting in the creation, enrichment, and isolation of new forms of life. For example, if a microorganism divides once every 40 minutes, a population thereof would double 36 times in 24 hours, and thus, one individual microorganism would become $2^{36}$ or $6.9 \times 10^{10}$ individuals, any of which could be a beneficial mutant.

The theory of evolution is a well-established principle of biology, and is based on the observation that chance mutations of various types occur in the reproduction of living organisms, through various mechanisms, and that these mutations may be advantageous or disadvantageous for future generations of the progeny. If they are advantageous, the offspring have a greater probability of reproducing than do the offspring of non-mutants, and the genetic change is passed on and enriched in the ensuing population. The present invention applies both the second law of thermodynamics and theory of evolution, more precisely evolutionary development, to create new organisms by directing evolution.

The second law of thermodynamics is used in accordance with the present invention to determine conditions in which microorganisms with desired traits are more likely to survive. If certain microorganisms in the population are able to survive, they are enriched and may be selected therefrom. If mutations occur that make a certain microorganism more fit under those conditions, those mutants are enriched and selected. Mutations can be made more frequent by including chemical mutagens or ultraviolet light, or any well-known methodology for inducing mutations. Such methods of mutagenesis are commonly employed, but the current invention applies the second law of thermodynamics to determine the conditions to control mutagenesis and the results therefrom. Although thermodynamics always drives the evolutionary process, the specific application in the present invention is to apply conditions that do not occur in nature to force evolution to create organisms that do not occur in nature.

For example, the present inventors first determined that no rumen microorganisms could survive greater than 6% by volume ethanol concentration, but over many generations of growth in media with 6% by volume ethanol, organisms emerged and were found that could tolerate as much as 10% by volume ethanol concentration. Mutants that could survive high ethanol concentration under conditions favoring fiber digestion, were selected by growing them on cellobiose. Thus, highly ethanol-tolerant fiber-digesting microbes were developed. Such organisms do not occur in nature because ethanol does not accumulate under conditions where fiber digestion occurs.

These unnatural or (artificial or man-made) conditions favoring the development or evolution of ethanol-tolerant microorganisms include: high $H_2$ pressure or presence of hydrogenase inhibitors, together with low $CO_2$ pressure, high ethanol concentration, and a source of biomass like plant fiber. The high hydrogen production would inhibit acetic acid production, the low $CO_2$ would inhibit propionic and lactic acid, and, thus, ethanol would become thermodynamically favorable. In nature, an assortment of different organic acids are produced in fermentation because the production of one set of metabolites inhibits further production of those metabolites, and shifts metabolism toward another set of metabolites. In these natural systems, high concentrations of ethanol would not occur with either high $H_2$ or low $CO_2$, because $CO_2$ is produced with ethanol and $H_2$ is not. In addition, high $H_2$ pressure occurs because of oxidation of biomass releasing $H_2$ and $CO_2$, or these two gases are readily used together to produce methane. Thus, conditions do not exist in nature that would strongly favor ethanol production in the presence of high ethanol concentration.

Unlike ethanol production from sugar using yeast, the concentration of sugars available for conversion is much lower when plant fiber is the feedstock because digestion of cellulose is slow and may be inhibited by sugars or low pH. Therefore, the present invention encompasses alternative procedures to create thermodynamically favorable gas concentrations, even at neutral pH and low sugar concentration, so that digestion of fiber and ethanol production can both proceed. Another approach would be to find a way to digest plant fiber to create high sugar concentrations, or to digest fiber at low pH. Nonetheless, these unnatural gas pressures and metabolite concentrations were created by adding gases or reagents or using inhibitors. These unnatural or man-made conditions enable selection, and sometimes mutation and selection of new unnatural but useful microorganisms.

Another method of enrichment and isolation disclosed herein in accordance with the present invention is the use of hydrogenase inhibitors. Using hydrogenase inhibitors can affect the thermodynamics within a cell and favors microorganisms that neither need to import or export hydrogen. For example, ethanol production or lactic acid producers would be favored, but both acetate or propionate producers disfavored. Compounds like carbon monoxide (CO) or cyanide (CN) directly inhibit hydrogenases. Previously, $Na_2SO_3$ appeared to inhibit hydrogenase and may be effective as well as be less toxic and less expensive than other inhibitors. Any means to inhibit hydrogenase may be used. Thus, the present invention emphasizes that use of $H_2$ or $SO_3$ increases ethanol production, or enables enrichment and the selection of ethanol-producing microorganisms. However, $H_2$ and $SO_3$ are only two examples of hydrogenase inhibitors and any hydrogenase inhibitor may be used. There are many hydrogenase inhibitors, including CO and CN, for example, and many other molecules that bind tightly to hydrogenases (which are similar to hemoglobin). Known toxins that affect hemoglobin or myoglobin would be likely to affect hydrogenases as well and thus, may be used. Of course, $O_2$ is known to bind tightly to hemoglobin and its toxic effect on strict anaerobes might be related to its binding to hydrogenases.

Any means to directly inhibit the production of acetate would also select against acetate producers and favor other microorganisms such as ethanol producers. For example, acetate kinase, which is part of the acetic acid production pathway, is sensitive to low pH, and high concentrations of acetate and ethanol itself. Thus, the present invention specifically contemplates using any means to decrease the pH inside the cell or increase the concentration of reactants that inhibit undesired products. For example, ionophores inhibit some acetic acid producers by dissipating proton gradients across membranes. Use of inhibitors of proton pumps, such as N,N-dicyclohexylcarbodiimide (DCCD), could also affect the ability of a microbe to make acids or make the organisms that produce acid less fit.

The same approach may be used for isolation of butanol-producing microorganisms in which organisms are isolable and useable in the present invention to directly convert plant fiber or other products directly to butanol, and in which higher concentrations of butanol will be tolerated. Using the methodologies described herein, given the vast number of microorganisms available in the environment from which to choose, i.e., about $10^{15}$ microorganisms in a cow's rumen, and the potential to develop and select mutants from rapidly reproducing populations, relatively little effort must be expended in order to find preferred microorganisms from which to produce butanol in advantageous amounts. The pathway for butanol production from glucose has much in common with the pathway for butyrate, a major rumen VFA. When rumen fluid was incubated under conditions to produce high hydrogen concentrations, butanol was formed, thus confirming that enzymes for butanol production are present. Every butyrate produced from glucose also produces $2CO_2$ and $2H_2$. Thus, similar methods to inhibit hydrogenases as used for producing ethanol would make production of butanol thermodynamically favorable as well. Based on the stoichiometry of butanol production, no $H_2$ need be exported or imported to make butanol from glucose. Making butanol from butyrate may, thus, be favored by selecting microorganisms under high $H_2$ pressure, or other substance to inhibit hydrogenases. Several isolates were selected to make butanol.

In contrast, isolation of organisms to produce propanol require high $H_2$ conditions, but not the inhibition of uptake hydrogenases, because the stochiometry requires that $6H_2$ be consumed to convert glucose to two propanols. Again the pathway is similar to that for propionate production, which is a common organic acid, and when rumen fluid was incubated under high $H_2$ conditions propanol was formed. Thus, microorganisms may also be isolated from the rumen, or many other microbial environments, for biodegradation of organic matter to produce propanol. In fact, one isolate selected for ethanol production does in fact also make propanol.

These examples demonstrate how thermodynamic analysis and use of inhibitors are used in the control or isolation of microorganisms, and to determine pathways to inhibit, and metabolites that are inhibitory in accordance with the present invention. The example could be applied to other metabolites including other alcohols, aldehydes, ketones, or acids. Of course, other metabolites need to also be considered including other gases that can be products or reactants (e.g. $CO_2$, $CH_4$), and other metabolites.

The present invention is based, in part, upon the discovery of microorganisms that can be used in a digester-fermenter to produce ethanol from biomass. These microorganisms have specific characteristics which make them advantageous for use in a process for digesting plant fiber to produce ethanol. The microorganisms of the present invention digest plant fiber, especially cellulose and hemicelluloses, in a rapid manner; convert a large percentage of cellulosic biomass, i.e., at least 30%, preferably at least 40%, and most preferably 50% by weight, to ethanol; grow and reproduce under conditions of ethanol production; and continue to do so until ethanol concentrations exceed the requisite 5% of volume that makes it cost effective to remove the ethanol from aqueous-based media.

This digestion of plant fiber includes cellulose and hemicelluloses to produce ethanol. Furthermore, and just as importantly, the microorganisms of the present invention grow and reproduce under conditions of ethanol production. Moreover, they do so until the produced ethanol concentration exceeds the requisite 5% by volume of ethanol required for economically-feasible separation from a aqueous-based solution. Further, the present invention specifically contemplates the use of single microorganism cultures that preferably meet the above requirements or mixed microorganism cultures that do as well. It is preferred that whether the culture is a single (or mono) culture or mixed culture that the total culture exhibit the above-described characteristics.

Preferably, the present isolated microorganisms digest both cellulose and hemicelluloses and convert nearly all of the carbon in it to ethanol carbon and $CO_2$, and, more preferably still, are tolerant to at least about 10% by volume concentration of ethanol.

Further, the present invention also provides a digestion process which is favorable for the production of ethanol. The present invention also contemplates, for example, continuously supplying substrate as opposed to feeding a slug of feed at once. Further, maintaining strictly anaerobic conditions has been found to increase ethanol concentrations, and the use of sulfide-reducing agents also increases ethanol production. However, see the discussion below regarding aerobic microorganisms.

A process is also described to produce the type of microbial culture described above. The microbes in the culture may be derived from the rumen of a ruminant or other anaerobic ecosystem like feces, manure digester, insect gut, soil, or other. The process isolates microbes by incubating under conditions that yield ethanol while digesting fiber. These conditions can include high $H_2$ pressure, presence of substrate that is desired to be digested (e.g. cellulose, cellobiose), desired preferred temperatures for the desired culture (for example, 40° C. or 55° C.), presence of ethanol, and other conditions.

Further, a process is described to calculate the equilibrium concentrations of a mixture of fermentation products, and using those calculations to determine optimal conditions to increase the concentration of the desired product.

Moreover, a process is described to test microbial cultures for their utility in a process to produce ethanol from plant fiber, in which the microbes are incubated with biomass under about 1 atmosphere of hydrogen pressure.

Additionally, a process is described to digest plant biomass and produce ethanol using microorganisms. This process may include digesting the biomass with a mixed culture of microorganisms. The biomass may contain cellulose, hemicelluloses, starch, mono-saccharides, glycerol, protein or other organic matter. The process may occur at about 25 to 65° C., but preferably at about 40° C. With some microorganisms, however the process preferably occurs at a higher temperature, such as in excess of 60° F., and more particularly about 65° C.

The present invention also provides certain additional preferred process parameters generally for digesting plant biomass using an undefined mixed culture of microorganisms. Such preferred process parameters include, for example, adding the biomass continually to increase ethanol concentration compared to slug feeding; controlling the gas pressures to maintain enough $CO_2$ to prevent VFA and ethanol degradation in the presence of high $H_2$; using microbial isolates to enhance a type of microbial activity; using a thermodynamic model to calculate the optimal conditions.

Additionally, the present invention also provides a method for predominantly producing a single lower alkyl alcohol which entails digesting biomass with naturally-occurring microorganisms which produces the single lower alkyl alcohol; and effecting an enrichment stage of the naturally-occurring microorganism in the presence of the single lower alkyl alcohol to promote digestion by one or more naturally-occurring microorganisms that are tolerant to said lower alkyl alcohol.

Thereby, the methodologies of the present invention may be used to produce ethanol, propanol or butanol.

Term Definitions

About: as used in the present specification means±10%. Thus, about 40° F. means 40° F.±4° F. Similarly, about 5% by volume means 5±0.5% by volume.

Butanol-tolerant: means that microorganism is able to grow in the presence of n-butanol. Generally, this means an amount of n-butanol of at least 0.5 to 1% by volume, and preferably about 2% by volume, in a digesting medium unless otherwise indicated in the present specification.

Cellulosic biomass: means biomass containing cellulose, i.e., plant fiber, which may also contain hemicelluloses or pectin, or other materials, such as ruminant feces that contain undigested cellulosic biomass. Examples of plant cellulosic biomass include, for example, hay, grass and wood.

Consolidated bioprocessing (or CBP): refers to the process of using microorganisms to digest cellulosic materials to produce ethanol, which is considered to be the simplest and lowest cost process for producing cellulosic ethanol.

Conversion percentage by weight: means the percentage of cellulose weight converted to ethanol or other biofuel. This calculation does not include exogenous water or hydrogen that may also be incorporated into ethanol. For example, 50% conversion of cellulose by weight means that 1 g of cellulose is converted to 0.5 g of ethanol. Nearly as much $CO_2$ may be produced.

Defined cultures: Cultures of microorganisms that have been isolated and characterized to some extent, possibly identified as genus and species, and possibly characterized by sequencing the variable region of 16S rDNA, or by sequencing the complete genome.

Direct digestion: means that the microorganisms act directly on the cellulosic biomass in its natural form (e.g hay) with minimal pretreatment to digest the cellulosic or fibrous content thereof.

Direct evolution: means to direct the development of microorganisms that are well suited, preferably particularly well suited, for a given environment that is not found in nature.

As exemplified herein, this can mean, for example, the development of microorganisms that produce high concentrations of lower alkyl alcohols, such as ethanol, in digestion media, and which are tolerant thereto.

Ethanol-tolerant: means that a microorganism is able to grow in the presence of ethanol. Generally, this means an amount of ethanol of at least 0.5 to 1% by volume, and preferably about 2% by volume, in a digesting medium unless otherwise indicated in the present specification.

Favorable Free Energy for Synthesis: means the change in Gibbs Free Energy (G) is negative for the combination of reactions that comprise the system that converts a set of reactants to a set of products, and the system can therefore convert the reactants to products. The $\Delta G$ is calculated based on the change in Gibbs Free Energy under standard conditions ($\Delta G°$) temperature and the concentrations or partial pressures of reactants and products. The $\Delta G°$ is calculated as the difference in Gibbs Free Energy of Formation ($\Delta G°_f$) for the products and reactants. The ($\Delta G°_f$ is the $\Delta G°$ for formation of any material from the elements i.e. graphite, $H_2$ or $CO_2$, for example, under standard conditions. Standard conditions means standard temperature (298.15K unless otherwise indicated), 1 molar concentration of all reactants and products, and 1 atmosphere partial pressure of gases.

Fermentation or Fermentation System: refers to the use of microorganisms to produce a product, for example, by digestion of biomass containing plant fiber; where the system refers to the totality of all possible reactions which occur during digestion. Production of lower alkyl alcohols other than ethanol is also contemplated, such as propanol and butanol.

Isolated microorganisms: means one or more microorganisms that either have been isolated from a natural environment and grown in culture, or that have been developed using the methodologies of the present invention and grown in culture.

Lower alkyl alcohols: means $C_2$-$C_5$, preferably $C_2$-$C_4$ alcohols, i.e., ethanol, propanol and butanol.

Mixed cultures: More than one strain of microorganism cultured together, may be defined or undefined, pure or impure cultures.

Not Found in Nature: means that conditions utilized to control mutagenesis of microorganisms in either increasing yield therefrom of a desired product, such as ethanol, or to increase tolerance of the microorganism to the desired product, such as ethanol, are not found in nature. Such conditions may include, for example, a growth medium for microorganisms that contains a high percentage of ethanol, i.e., 6% by volume, using cellobiose as a material for digestion. Such conditions may also include, for example, high $H_2$ pressure, presence of hydrogenase inhibitors, and low $CO_2$ pressure. These are conditions not found in nature.

Plant fiber: Defined chemically as comprising cellulose, hemicellulose, pectin or lignin, or combination thereof, and found in plant cell wall and many forms of feedstock including whole plants, biofuel crops (e.g. switchgrass, algae), food byproducts, wood, wood byproducts, paper, waste, animal manure, human manure, and others.

Propanol-tolerant: means that a microorganism is able to grow in the presence of n-propanol. Generally, this means an amount of n-propanol of at least 0.5 to 1% by volume, and preferably about 2% by volume, in a digesting medium unless otherwise indicated in the present specification.

Pure cultures: Cultures of microorganisms that have been isolated or partially isolated to eliminate contaminant microorganisms. Cultures can be a single strain or multiple strains (mixed cultures).

Thermodynamically favorable conditions: means reaction conditions that render a reaction of interest to be thermodynamically favorable. Such reactions conditions might include pH, temperature, headspace vacuum, headspace perfusion gases or inclusion of reducing agents, for example.

Thermodynamically favorable reaction: the concentrations of reactants and products and other factors, such as temperature, headspace gas and the pressure thereof, for example, are such that the reaction is favored over other reactions occurring with competing reaction pathways, i.e., a reaction is thermodynamically favorable.

Thermodynamically feasible reaction: the multiplicative product of reaction product concentrations divided by the multiplicative product of reactant concentrations is low enough for the reaction to proceed spontaneously in the forward direction, i.e., a reaction is thermodynamically feasible.

Undefined cultures: cultures of microorganisms taken from a source without having isolated individual microbes or characterized individual organisms.

VFA: volatile fatty acids (e.g. acetic acid, propionic acid, butyric acid, lactic acid)

I. Microorganisms

One aspect of the present invention entails the provision of a microbial culture of isolated microorganisms that digests plant fiber, especially cellulose and hemicelluloses, in a rapid manner; converts a large percentage of plant biomass (e.g. >50%) to ethanol; grows and reproduces under these conditions of ethanol production; and continues to do so until ethanol concentrations exceed the requisite 5% of volume that makes it cost effective to remove the ethanol. In accordance with the present invention, isolated strains of microorganisms that fit this description may be used by themselves or in combination with other organisms to make a culture that fits this description. Of course, mixed cultures of microbial cultures may be obtained directly from a ruminant gut sample in order to screen and select for high producers of lower alkyl alcohols.

Microorganisms that have already been isolated and used for other processes, or even for ethanol production, may be used in accordance with the present invention if they satisfy the requirements set forth herein. However, few, if any, existing microbial cultures have been tested for ethanol production under the conditions of the fermentation needed to shift fermentation toward ethanol, as described herein, hence, it is not known how many known microbial cultures used for other purposes have these traits. In such a case, providing a microbial culture in accordance with the present invention only requires screening of the isolated microbial culture to determine if it satisfies the conditions described herein. Screening would make the culture "known" to have the required conditions, which would make the culture useful for the consolidated bioprocessing method of producing ethanol as well as other lower alkyl alcohols.

For example, a purified strain of *Ruminococcus albus* was obtained and tested under conditions required to produce ethanol, and it was tested also for its tolerance to ethanol.

Isolated Microorganisms

The present inventors have isolated microorganisms that meet all of the requirements for producing ethanol directly from cellulosic feedstock using a consolidated bioprocessing method. Several strains, isolated from the rumen of cows, were shown to readily digest cellulosic biomass, convert greater than 50% of carbon to ethanol, grow and continue to produce ethanol until concentrations of ethanol produced exceed 5% by volume. Some isolated microorganisms were found to digest both cellulose and hemicelluloses and convert nearly all of the carbon in it to ethanol and COz. Some microbial isolates are tolerant to ethanol concentrations of up to 10% ethanol by volume. Strains differ in the rate of digestion of different types of feedstock, and in the secondary products they produce (e.g. propionic acid vs. acetic acid). Several strains may also use other substrates besides cellulose and hemicelluloses. Strains differ in their optimal pH and temperature for growth. Thus, cellulosic ethanol production may be practiced in accordance with the present invention with one or more of the isolated strains in monoculture or mixed cultures, and with different conditions or with changing conditions, and on different types of substrate.

Pure defined cultures offer both advantages and disadvantages over undefined mixed cultures. Digestion and fermentation with defined cultures can remove some pathways of fermentation that are undesirable so that even more carbon is converted to ethanol, or so that it is converted more readily. The methods to control fermentation may be easier with pure cultures. Cultures may be used in aseptic conditions to completely eliminate other organisms, or in non-aseptic conditions where competition from other organisms is controlled by using inhibitors or metabolites, or they may be added to undefined cultures to increase a certain type of microbial activity.

Other isolated strains were selected for their ability to produce acetic acid rather than ethanol. These strains may be subjected to a separate process to produce ethanol or other products from the acetic acid. There are different pathways for acetic acid production. The microbes may convert one glucose equivalent to three acetic acid molecules directly. It would usually be just as satisfactory, however, to make two acetic acid molecules and, $2CO_2$, and $4H_2$ molecules. The gases could be converted by a different organism to make a third acetic acid, or the gases could be removed and used for a different process. Strains may also be selected to produce propionate, butyrate or other alcohols. Any acids could be converted to alcohols in a subsequent step. Lactic acid may also be produced from glucose equivalent. Or bacteria, such as *Streptococcus bovis*, can convert lactic acid directly to ethanol under the correct conditions. Thus, several microbial species could be isolated to produce ethanol or other alcohols by a number of different pathways.

Isolated microorganisms of interest include, for example, gram positive rods (apparent genus Clostridia), and weakly gram positive cocci which appear to derive from the genus *Ruminococclis*. Identified microorganisms also include members of the genera *Enterococcus, Pediococcus, Lactobacillus* and *Staphylococcus*.

Examples of Microorganisms and their Characterization

The present inventors established that one previously isolated microorganism, *Ruminococcus albus* strain 7, i.e., RA7, (ATCC #27210) for example, possesses three traits making it particularly useful to industrial ethanol production. First, it was shown to digest celluose and hemicellulose, and to ferment up to 41% of carbon from cellulose to ethanol when incubated with gases it produced in continuous culture. Second, it was also found that RA7 grows in media with up to 6% by volume ethanol concentration. Third, in fact, it produced more ethanol when grown with 6% by volume ethanol than without ethanol. Such characteristics render such a microorganism advantageous for consolidated bioprocessing. That is, naturally-occurring microorganisms that both convert a substantial amount of cellulosic biomass to ethanol and which are. ethanol tolerant are advantageously used in consolidated bioprocessing in accordance with the present invention.

The conditions required to make *R. albus* and other microorganisms produce ethanol, based on previous literature, thermodynamic calculations and confirmation with empirical studies by the present inventors, are as follows: high partial pressure of hydrogen, and low substrate availability such as would occur during continuous culture. The theoretical growth rates of microorganisms under these conditions are about half of the expected growth rates under acetic acid production conditions. Thus, slow turnover times in continuous culture or methods to maintain or return microbes to the digester-fermenter may be needed.

Further, the present inventors discovered other ethanol-producing microorganisms in the rumen of cattle that were developed to grow in the presence of ethanol of up to 10% by volume concentration, and digest cellulose (AVICEL® (microcrystalline cellulose)) or use 5-carbon sugars (xylose and arabinose, for example). The fact that rumen microbes produce ethanol is counterintuitive inasmuch as ethanol concentrations in the rumen are negligible. The fact that rumen microbes would be ethanol tolerant is unexpected inasmuch as ethanol concentrations are so low in the rumen. The reason for this adaptation is unknown. Further, microbes were isolated with maximal growth at different temperatures (e.g. 40° C. or 55° C.), for example. Ethanol-tolerant, ethanol-producing, cellulolytic microbes were isolated that were tolerant to sulfite ($SO_3$) in the media. Since growth of many other microbes could be inhibited with sulfite, this adaptation is useful for controlling metabolism by competing microorganisms. Several microorganisms produced no acid when incubated with hydrogen pressure. If microorganisms do not produce acid, all of the substrate can be converted to ethanol and pH or acidity will not inhibit further microbial growth and production.

Another exemplary microorganism was a weakly gram positive cocci isolated from rumen fluid. An experiment was conducted to test different methods to prevent growth or degradation of ethanol in vials while they were being analyzed. One treatment was addition of $NaSO_3$. Samples of rumen fluid were centrifuged (5000 g, 20 min). Supernatant was removed, and 0.5% ethanol and $NaSO_3$ were added. Sulfite was an unsuccessful inhibitor of microbial growth of rumen bacteria in the supernatant. A culture grew after 2 days at room temperature.

The culture was incubated on cellobiose with a roll tube. Colonies that grew were isolated and tested on 2% cellobiose in 6% by volume ethanol media under 1 atm $H_2$. One strain grew and appeared to convert all the cellobiose to ethanol. Final concentration averaged 9% by volume ethanol, which was an overestimate (more than 100% conversion to ethanol), but within the range of error of complete conversion. In some incubations, perfused $H_2$ disappeared with very high ethanol production, suggesting that produced $CO_2$ and perfused $H_2$ were assimilated into ethanol.

One unexpected discovery was that many of the isolated microorganisms produced ethanol nearly exclusively, and in pure culture no longer needed the addition of $H_2$ or inhibitors of acid production. By using these additives to create conditions favoring microbes that produced mostly ethanol, organisms were enriched and isolated that produced mostly ethanol even in the absence of those conditions. For example, when several isolates known to produce ethanol were incubated in the presence of 2 atm of CO, $H_2$ or $CO_2$, there was no effect of which gas was used. All samples produced high concentrations ethanol (up to 7.0% by volume), and converted up to about 50% of cellobiose to ethanol. The CO or $H_2$ was expected to inhibit hydrogenases that enable some microorganisms to release $H_2$ in association with acetic acid production. The organisms having been selected under those conditions, did not appear to have hydrogenases, and were unaffected.

Functional Characteristics of Microbial Cultures

Before isolating microorganisms for various purposes, it is necessary to determine the functional requirements of the microorganisms for the process in which they will be used, such as, for consolidated bioprocessing, and the variations in those requirements for that purpose. Once these requirements are determined, the conditions that favor those requirements can be created, for example, by considering the thermodynamics favoring the desired pathways. Several examples of microbial cultures (pure cultures or co-cultures) that have specific functional activities, their uses, and how they can be developed are given below.

In U.S. Ser. No. 12/000,856, it was demonstrated that the rumen microbial ecosystem, like many other microbial cultures, contained many microorganisms and pathways resulting in a broad array of activity. The end result of this activity is determined by the second law of thermodynamics, but the profile of products may be altered by adding metabolites or inhibiting certain pathways. Further, the end products could also be manipulated by the complete removal of certain pathways by isolating specific organisms, using inhibitors with isolates, or genetically modifying organisms. The microorganisms could be undefined cultures or isolated cultures used individually or in mixed cultures to produce the desired activity for biofuel production. Thus, although ethanol can be produced by rumen microorganisms, ethanol does not accumulate because the microorganisms favor production of acids rather than ethanol under natural conditions. Even if ethanol is produced, symbiotic organisms can obtain more energy by converting it to acid. With different conditions, ethanol can be thermodynamically favored, and the organisms that produce it can be enriched and selected for.

Using this concept to remove certain types of reaction pathways from the microbial ecosystem through the means described herein, the following functions could be orchestrated by microbial cultures obtained from a mixed culture such as would exist in the rumen of the cow or many other natural and diverse ecosystems. These are functions that may not occur naturally because of the need to limit some activity that would naturally be present. For example, many microbes can readily degrade various forms of biomass to mono-saccharides, but in a natural state these microbes would continue to degrade these mono-saccharides and incorporate them into cell organic matter or burn them for energy. The production of biofuels or other desired products from biomass, as opposed to the common products, is as much about limiting enzyme activity as it is about adding it. Isolation of microorganisms can often be used to limit the activity in the system because in nature the metabolites are passed from one organism to the others, thus not providing organisms to pick up the metabolite can enable a desired metabolite's accumulation. The present disclosure describes and illustrates how to effect the following activities using microbial cultures, as well as ways to develop the microbial cultures themselves:

a. Plant biomass digestion directly to alkyl alcohol, wherein the biomass is plant fiber (comprising: cellulose, hemicellulose, pectin, lignin), starch, sugars (comprising: monosaccharides, disaccharides, 5-carbon sugars, 6-carbon sugars), or others.

b. Plant biomass digestion to an intermediate like mono-saccharide or di-saccharide. The released sugars being available to be further converted to a biofuel like alcohol by another microorganism.

c. Plant biomass digestion to certain organic acids. For example, if acetic acid or butyric acid are desired, a pure culture of organisms that only produces these acids could be selected. These acids could then be used for another process like ethanol or butanol production.

d. Conversion of a mono-saccharide or di-saccharide to alcohol or other biofuel.

e. Conversion of organic acid to alkyl alcohol. For example, lactic acid conversion to ethanol, or butyric acid conversion to butanol.

f. Conversion of one organic acid to another. For example, acetic acid converted to propionic acid, or acetic acids converted to butyric acids, or further elongation of fatty acids, or shortening of fatty acids.

g. Conversion of insoluble organic matter (e.g. plant fiber) to methane.

h. Conversion of organic acids to methane.

i. Conversion of biomass to $H_2$ and acetic acid. If high $H_2$ concentration is desired, organisms that use $H_2$ would need to be excluded.

J. Conversion of biomass to $H_2$ and $CO_2$, which could also include acetic acid degrading organisms. These organisms would be used in combination with a way to make acetic acid degradation thermodynamically favorable such as purging of gases.

k. Conversion of $CO_2$ and $H_2$ to acetic acid. These organisms might be used to recover low concentrations of $H_2$ or $CO_2$, in which total gas pressures could be elevated. The acetic acid could be further converted to other VFA with other cultures.

l. Conversion of $CO_2$ and $H_2$ to ethanol. The conversion of $CO_2$ and $H_2$ to acetic acid, and the interconversion of acetic acid and ethanol, were shown in the previous patent application to be near equilibrium. Thus, these conversions would be a means to make ethanol from low concentrations of some gases.

More than one of functions a)-l) may be practiced together. For example, one organism may degrade biomass to mono-saccharide (function a) and another one convert the mono-saccharide to alcohol (function d). Another example is where one microorganism may produce ethanol, and $CO_2$ (function d), while another microorganism may use $CO_2$ and added $H_2$ to produce more ethanol (function l). This combination would result in very efficient ethanol production from biomass and is specifically contemplated by the present inventors.

Developing Microbial Cultures for these Functions

A natural anaerobic or aerobic ecosystem has enzymes to produce many different products or intermediates, but typically these systems are stable and produce the same profile of products. By selecting for certain enzyme activity and removing others, the desired products can be produced and concentrated. Many previous attempts to introduce alcohol production enzymes into organisms failed even when the full range of activity needed was present, because the absence of certain activity is also needed.

A flow diagram of the required steps for various end products is shown in FIG. 1 with steps identified as numbers. For each of the functions (a-l) described above, the needed available pathways and the needed exclusion of available pathways are indicated below. Letters in brackets preceding each item refer to the function described above and the microbial culture developed for that function. Numbers in brackets refer to the steps in FIG. 1, which are affected.

(a) In the first example, ethanol can be produced by digesting biomass (1), fermenting it (2), and producing ethanol (3) while limiting the production of acids (4-7), and limiting reduction of $CO_2$ (10) or $O_2$ (11). Thus, the important steps are: 1, 2 and 3, but it is also important not to include other options. Including step 8 can be a way to make the process more efficient and convert $CO_2$ and added $H_2$ to ethanol, but it would only work when $CO_2$ and $H_2$ concentrations are high enough, otherwise it could result in a loss of ethanol.

Obtaining a culture that degrades fiber requires that at some stage of the enrichment and isolation, the microorganisms are grown on a source of fiber as the substrate. Enriching and isolating microbes that produce ethanol can be achieved by growing the microbes under conditions where either production or degradation of ethanol is advantageous. For example, growing the microbes in the presence of ethanol under $CO_2$ pressure would result in ethanol degradation to VFA, and would select for microbes that can degrade ethanol to a VFA as well as for ethanol-tolerant species. These microorganisms would have the means to make both the VFA and ethanol, and further development might be needed if only ethanol is desired. In contrast, growing the microorganisms under conditions that favor ethanol production over VFA could select for microbes that only make ethanol. For example, under high hydrogen pressure or with use of hydrogenase inhibitors, acetate production is disfavored and organisms that produce only ethanol have an advantage. If $CO_2$ concentrations are low, propionate and lactate are also disfavored shifting equilibrium toward ethanol. This would explain why exclusive ethanol-producing bacteria were isolated under these conditions.

Another type of culture that is especially useful for ethanol production is an oxygen-utilizing ethanol-producing culture. When glucose is the feedstock, yeast utilizes this pathway. However, oxygen-using fiber-digesting bacteria can also be isolated from natural mixed cultures. The goal in this case is digestion of fiber (1) and fermentation to ethanol (2, 3) without pathways for VFA production. Also, ethanol tolerance is required. Fiber digestion and use of oxygen can result in degradation of lignin, and efficient microbial growth without the buildup of inhibitory products that might be difficult to remove. This aerobic phase may be followed by closing the environment to $O_2$ (12), adding more feedstock and actively digesting it to ethanol in an anaerobic phase. Under aerobic conditions, these microbes could completely digest ethanol to $CO_2$ and $H_2O$, but under anaerobic conditions, ethanol would be the end product.
The way to select these microbes is to grow them under aerobic conditions in the presence of high concentrations of ethanol as the only substrate. Then, the survivors of this enrichment are grown on plant fiber as the only substrate. These may be grown under anaerobic conditions, perhaps with inhibitors of hydrogenases (CO, $SO_3$), or $H_2$ to select against acid producers. Microorganisms were isolated that grew well in open air, and made ethanol under anaerobic conditions.

(b) A different way to produce an alkyl alcohol or other desired bioproduct would be to use microorganisms to digest plant biomass (1) but not to ferment it (2). Whereas microorganisms that digest biomass but don't utilize it are not fit, they would not be easy to isolate from a mixed culture. However, some organisms digest biomass by producing enzymes, and these enzymes may be active even after the microbes no-longer are. Some organisms might be added that can use very low concentrations of the sugars to effectively cross feed with microorganisms that do the digesting, and produce the desired product. It may be possible to inhibit the uptake or use of the sugars or disaccharides that are produced to increase what spills to other organisms that produce a favored product. The conditions could change in the fermentation due to production of products (e.g. pH decrease) to make the uptake unfavorable
over time. In particular, aerobic microorganisms can grow readily by converting biomass to $CO_2$ and $H_2O$, but may not survive anaerobic conditions. The enzymes degrade the cellulose or hemicellulose to mono- or disaccharides, and the organisms transport these sugars in aerobic conditions. This approach involves selecting for aerobic microorganisms that use enzymes for biomass digestion, where the enzyme activity continues in anaerobic conditions, but where the organisms do not take the sugars up. These organisms may be used to grow on substrate and produce enzymes. Additional substrate could be added and degraded under anaerobic conditions, and that degraded substrate used by other organisms to produce a desired product. For example, a yeast or bacterium that can produce a desired alkyl alcohol could be used in the second stage of the fermentation.

(c) A third way to produce an alkyl alcohol would be to produce a volatile fatty acid which can be converted to an alkyl alcohol. The fiber would be digested (1), and fermented (2), and a certain VFA or a mixture of VFA could be produced depending on the desired intermediate and product. A pure culture of microorganisms can produce one or two VFA, or be further controlled using gaseous end products. Mixed cultures of VFA can be controlled with gas pressures to shift fermentation toward the desired VFA. For example, acetic acid is a common VFA that can be readily produced from fiber digesting bacteria. In pure culture, it can be exclusively produced and later converted to ethanol.

(d) Microorganisms can be isolated that are particularly useful for conversion of mono- or disaccharide to alkyl alcohol (2, 3). The disaccharide may include cellobiose the 2-glucose unit disaccharide of cellulose, which isn't easily used by yeast. These microorganisms could also be advantageous over yeast because of the low concentration of sugar they may require. For example, *Streptococcus bovis* produces ethanol under reducing conditions (high hydrogen) and low glucose concentration. It can compete effectively with some microbial populations of (b) and use the liberated sugars to produce ethanol through cross feeding.

(e) There are two types of microbial populations that might be desired to produce $H_2$ as a fuel. Microorganisms can be isolated that can digest biomass (1) and convert it to acetate (2, 4).
These microorganisms release $H_2$. The $H_2$ concentration can be about 0.67 atm with the remainder of the gas $CO_2$. The acetate can be used in a subsequent process to make ethanol or $CH_4$. This microbial population should not contain methanogens (10), or propionic acid bacteria (5), or reductive acetogens (9) or ethanologens (8).

(f) Where it is cost effective to remove low concentrations of $H_2$, organisms that convert acetic acid to $CO_2$ and $H_2$ may be used with the organisms of (i) to make two thirds more $H_2$ than could be made with microbial culture (i). These populations should not include methanogens (10), or propionic acid bacteria (5), but even a natural mixed culture could be used if the $H_2$ is removed at very low concentrations, or its uptake inhibited.

(g) An efficient way to make acetic acid from waste gases is to maintain a population of reductive acetogens with high enough pressures of $CO_2$ and $H_2$. Others have proposed adding reductive acetogens to increase acetic acid production in the rumen and decrease methane losses. However, this method would not work in the cow's rumen because the acetogens are already there, and the rumen is near equilibrium. On the other hand, a digester can increase its total pressure, or the partial pressure of either or both gases to promote the reaction. A culture that does not contain methanogens would naturally make it possible to maintain higher $H_2$ and $CO_2$ pressure than one that contains methanogens, and therefore promote greater acetate synthesis. Acetic acid can be subsequently removed and used, converted chemically to other product, or converted to other acid or alcohol through other pathways made available to the fermentation (e.g. ethanol, propanol or butanol).

(i) Because the rumen has the microorganisms to assimilate $CO_2$ and $H_2$ into acetic acid, and acetic acid is in equilibrium with ethanol, the pathways are present to convert $CO_2$ and $H_2$ to ethanol. Such a conversion might produce both ethanol and acetic acid, unless pathway 8 is possible without pathway 9. Selecting for an organism that can convert $CO_2$ and $H_2$ directly to ethanol, and not have the ability to produce acetic acid, is possible because the pathway does not go though acetic acid. One way to enrich for such organisms is to grow mixed cultures with optimal $CO_2$ and $H_2$ for ethanol production. Another way would be to first favor the degradation of ethanol by growing mixed cultures in the presence of ethanol and low $CO_2$ and/or $H_2$, and then reverse the conditions. Air would select for oxygen-utilizing organisms, but inert gas like $N_2$ would select for non-oxygen utilizing microorganisms. High $CO_2$ and high $H_2$ conditions could be used subsequently to enrich or select from this population for organisms that synthesize ethanol directly. Inhibitors of hydrogenases or acid production may be included to prevent acetogens from being selected.

There are several reasons to include oxygen-utilizing microorganisms in anaerobic fermentations, and to select for such organisms. Oxygen-using microorganisms can be used to scavenge $O_2$ and make the fermentation more hospitable to strict anaerobes, and to shift fermentation toward more reduced products. Whereas reduction of oxygen may be a major means for organisms to obtain energy, organisms that depend on it would not need, and therefore would not have as many pathways for anaerobic fermentation. In the case where they cannot grow at all in the absence of oxygen, it may be easy to prevent them from carrying out unwanted pathways fermentations once their job (removing oxygen or digesting feed to sugars) is done. In other cases, the oxygen-utilizing organisms can be grown under in open air, and once adequate cell numbers are established to enable rapid digestion and conversion of remaining or added substrate, anaerobic fermentation to desired products can be achieved. Lignin cannot be readily digested by anaerobes, but it can be digested by aerobes. However, it is difficult to make it into ethanol aerobically. One way to use the lignified residues after digestion would be to grow aerobes on it, and these aerobes may be subsequently used with additional feedstock, or may be digested themselves, to produce ethanol.

Reference will now be made to certain examples which are provided solely for illustrative purposes and which are not intended to limit the present invention.

Example I

Thermodynamic analysis was used to determine concentrations of metabolites to select for ethanol production in an undefined mixed population of microorganisms to simultaneously enrich for desired natural organisms and direct developmental evolution of those microorganisms. In this case, the organisms that develop are unique because the original culture had no microorganisms that could grow in 10% ethanol. The present inventors also directed the evolution of microorganisms after they were isolated in pure culture. Again thermodynamic analysis was used to determine and establish conditions to select for desired mutants.

One strain of bacteria was isolated that readily converted different forms of biomass to ethanol and made no other measured products (e.g. no volatile fatty acids or other alcohols). The organism grew readily and could digest different feedstock including pure cellulose (AVICEL® (microcrystalline cellulose)), and use five-carbon sugars as well as glucose and cellobiose. However, this organism was not ethanol tolerant beyond about 2% concentration. After several runs incubating the organism with increasing amounts of ethanol (starting with 2% and increasing to 4%), the organism's ethanol tolerance increased. In these incubations, the produced $CO_2$ was removed during the fermentation by purging intermittently with other gases (e.g. $N_2$, $H_2$). This combination of supply of cellulose, removal of $CO_2$, and increasing concentrations of ethanol made it thermodynamically feasible for the organism to survive while converting the biomass to ethanol and $CO_2$. Because the original strain was also preserved, and a pure monoculture was improved, the DNA sequence from each organism can be compared to determine which genes were altered, and consequently determine which genes may be important to the improvements.

A second example of directing evolution by establishing thermodynamic conditions favoring ethanol was provided using the same organism. The organism's ability to digest more complex forms of plant fiber and convert them to ethanol were improved by using these same conditions favoring ethanol production with grass hay as the substrate. Organisms could be developed this way to digest various forms of feedstock.

In the previous cases, organisms were created with greater ability to tolerate high ethanol, or to produce ethanol under high ethanol concentrations. However, the present inventors also directed evolution of organisms to convert a higher percentage of the plant fiber to ethanol rather than other products. Examples of these improvements pertain to both pure cultures and mixed cultures. In this case, however, for examples from undefined cultures, it is impossible to differentiate enrichment of desired organisms from pre-existing mutants and creation of new mutant microorganisms.

The conditions for the enrichment described include growing the microorganisms on a source of biomass using high $H_2$, CO, $SO_3$ or other agents to shift equilibrium against acetic acid or propionic acid producers, and low concentrations of $CO_2$, with removal of $CO_2$ during digestion. These conditions make it thermodynamically favorable for ethanol production. Organisms that produce ethanol exclusively are favored and enriched, while those that continue to produce acids are not. Even producing small amounts of acid is a disadvantage compared with organisms that only produce ethanol, especially when acids are plentiful in the media. Thus, enrichments under high $H_2$ led to isolation of several mutants that did not produce acids at all. This result may have occurred because of the enrichment and selection of existing microorganisms or the creation of new microorganisms.

Some isolated ethanol-producing fiber-digesting microorganisms produced both ethanol and organic acids from cellulosic biomass. However, they produce ethanol when ethanol is thermodynamically favored, and other products when those products are favored. For example, R. albus strain 7 obtained from a deposit (ATCC #27210) originally produced ethanol when incubated with H$_2$, but not when incubated with CO$_2$ or N$_2$. However, after growing R. albus strain 7 on H$_2$ and subculturing, the organism produced ethanol under H$_2$, CO$_2$ or N$_2$ gas headspace. Similar results were observed with other isolates, in some cases completely eliminating the effect of N$_2$ vs. H$_2$ on the amount of ethanol produced. Growing isolates under the conditions that make ethanol the most thermodynamically favored product shifts that fermentation immediately toward ethanol, but also directs developments or evolution of microorganisms to convert greater amounts of biomass to ethanol. Thus, microorganisms can be created by applying the second law of thermodynamics to directing evolution of microorganisms, in this case shifting fermentation to increase ethanol production.

Non-functional genes could theoretically mutate back to the original, but this remote possibility is easily managed. The return to the original form could occur in nature, or through applying thermodynamic conditions favoring the original form. For example, incubating mutants that do not produce acetic acid in the presence of low concentrations of H$_2$ that favor acetic acid production could result in the reverse mutants being selected, especially if ethanol production becomes thermodynamically infeasible as products build up. However, the possibility of reverse mutations would be easily managed in digesters to produce ethanol using the microorganisms. First, if conditions are maintained in digesters to keep ethanol production thermodynamically feasible, the desired organisms will grow along with the reverse mutants. A few reverse mutants might survive and grow, but would be out numbered by the desired microorganisms. Second, any of thousands of mutations can result in the loss of enzyme activity, but reverse mutation requires specific mutations, and may require large segments of DNA to be re-developed. Thus, it is much easier to make genes non-functional than to make them functional, and providing thermodynamically favorable conditions can easily make undesired genes nonfunctional. In general, for any product produced by microorganisms developed this way, digesters must maintain conditions so that the desired activity is thermodynamically feasible, but these conditions no longer need to be thermodynamically favorable to a certain product over other products once the pathways to develop the other products are removed.

Rapid evolution of microorganisms can work against desired purposes. When maintaining a desired enzyme activity is required, it is necessary to maintain conditions in the digester or stock culture to continually re-select for the desired organisms by keeping the desired reactions thermodynamically feasible, and by maintaining conditions that make it advantageous to use the desired activity. For example, ethanol-producing cultures are maintained and grown under conditions making ethanol production thermodynamically feasible, and different diverse substrates are used to maintain their ability to digest them.

Example 2

One way to increase ethanol concentration produced is to eliminate methanogens so the CO$_2$ pressure doesn't become low enough to degrade ethanol. Another way to increase ethanol concentration produced is to include methanogens to drive down the CO$_2$ pressure and make ethanol production from glucose more thermodynamically favorable, but in this case eliminate the ethanol degraders. In essence, the natural system has three simultaneous reactions:

$$\text{Glucose} \leftrightarrow 2\text{ ethanol} + 2\text{CO}_2 \qquad 1)$$

$$\text{CO}_2 + 4\text{H}_2 \leftrightarrow \text{CH}_4 + 2\text{H}_2\text{O} \qquad 2)$$

$$\text{ethanol} + 3\text{H}_2\text{O} \leftrightarrow 2\text{CO}_2 + 6\text{H}_2 \qquad 3)$$

In accordance with the present invention, the following steps, as numbered above, produce the results indicated:
a) 1 and 2 and added H$_2$ makes for high concentration of ethanol and methane;
b) 1 and 3 and added H$_2$ (and especially pressure) make for ethanol production from two directions; and
c) 1, 2 and 3 and added H$_2$ just makes methane (this is the natural system in which biomass degraded quickly, just like removing H$_2$)

All three are useful combinations for different purposes.

Example 3

A butanol-tolerant microorganism was isolated that grew on cellobiose. It was isolated on cellobiose after enriching on 4% butanol under CO$_2$. The microorganism isolated produced butanol, and was tolerant to 6% butanol, and thrived on 10% ethanol.

This demonstrates that the same methodologies described above for ethanol are also effective for butanol, and by analogy, for propanol.

II. Microbial Isolation Methods

A description of how microorganisms were and may be isolated is presented herein. The isolation process is another aspect of the present invention. Although the present invention includes microbial cultures that can be used for the process that is described to make lower alkyl alcohols such as ethanol, propanol or butanol, the methods of isolation also afford additional microbial cultures that are best suited to a particular process of interest. For example, microorganisms may be selected for high tolerance to high ethanol concentrations, rapid digestion of a particular feedstock, or *facile* management in a particular system. Exemplary methods of isolation are described below.

Exemplary Methods of Isolation

The organisms were isolated from the rumen of a non-lactating Holstein cow fed a diet of grass hay. The cow had a cannula into her rumen from which rumen contents could be taken. Although the cow's rumen is a known source for such microbes, other similar anaerobic environments are also likely to harbor some of the same or similar organisms. These environments include animal feces, manure digesters, insect gut (especially termite or carpenter ant). Other environments might also harbor unique strains with special attributes desired for a process to make ethanol.

Contents were processed in strict anaerobic conditions in some cases, maintaining them under oxygen-free CO$_2$. Contents were ground 1 minute in a blender (under CO$_2$), and filtered through four layers of cheese cloth and glass wool. Initially all procedures maintained conditions for strict anaerobic bacteria, although it is not known if this was necessary. In fact, later, other organisms were enriched and isolated in open, aerobic conditions.

In some cases, enrichment of the microorganisms in the rumen fluid preceded the isolation of individual strains. When enriched, contents were incubated on substrate (e.g. AVICEL® (microcrystalline cellulose), grass hay, arabinose and xylose) in media with phosphate buffer, salts, macrominerals and microminerals according to the procedure of Goering and Van Soest (1970). The substrate used for enrichment was selected to obtain organisms capable of degrading a certain type of substrate. Other substrates could be used (e.g. paper, leaves, saw dust) to optimize degradation of other feedstocks. If microorganisms were desired to degrade algae, the substrate might have been algae. Additions to the media were made to enrich for microorganisms with specific capabilities. For example, some enrichments included different levels of ethanol (0, 4, 8, 10, 12% by volume). Some enrichments in 4% or 8% by volume ethanol were transferred to 8% or 12% by volume ethanol supplementation, and subcultured to induce greater ethanol tolerance (mutagenomics). Others had different amounts of VFA. The headspace gases also varied, sometimes using $CO_2$, $N_2$ or $H_2$. The pH of the media and the temperature of fermentation were also varied. Usually, pH 6.8 was preferred for maximal fiber digestion, and 40° C. is the temperature of the rumen, but higher (e.g. 55° C.) and lower (25° C.) temperatures as well as others were also used. Sulfite was also included to select for sulfite-tolerant fiber digesters. The present inventors previously showed that ethanol concentrations were much higher in the presence of sulfite, but fiber digestion was decreased.

All these variations were used and additional variations may also be used, and different microorganisms may be selected this way. Many of the attempts of enrichment provided organisms that met the criteria for the proposed ethanol production process. For isolating ethanol tolerant organisms, high ethanol concentration is preferred. However, ethanol degrading organisms can grow under $CO_2$ pressure without the ability to digest the intended substrate (e.g. cellulose). Alternatively, organisms were enriched with ethanol and plant fiber and $H_2$ gas. In these cases, ethanol degradation was made less favorable. Enrichment involved growing the undefined mixed culture for 24 h under the defined conditions, then transferring 10% of the culture to new media with similar starting composition as the original media. This process was repeated for four days.

Microorganisms were isolated using Hungate roll tubes. Later a glove-box (anaerobic chamber) was purchased that enabled use of agar plates under strict anaerobic conditions, but roll tubes were still used for high hydrogen conditions. Enriched inocula was diluted serially up to $10^{13}$ strength and 1-ml sample was added to warm agar, and then added to a tube containing cellobiose, arabinose and/or xylose. and maintained under desired gas pressures. Media usually contained a carbohydrate source (AVICEL® (microcrystalline cellulose), cellobiose, arabinose and xylose), and nitrogen source ($NH_4$, tryptic digest of casein). Usually media also contained yeast extract or autoclaved rumen fluid, as well as macrominerals (e.g. Ca, Mg, Na) and microminerals (e.g. Fe, Mn).

Sodium sulfide and cysteine were used as reducing agents, and resazurin was added to monitor reducing conditions. Tubes were maintained under $CO_2$ pressure or other gas ($H_2$ and $N_2$). Tubes were incubated at 40° C. for 1 to 4 days and individual colonies were sampled to fresh sterile broth and incubated until they grew. Conditions for incubation reflected the conditions for their eventual use to produce ethanol or other alkyl-alcohol. Indifferent runs, these conditions included varying the use of substrates (e.g. AVICEL® (microcrystalline cellulose), cellobiose, xylose, arabinose), varying the gas composition ($CO_2$, $N_2$, $H_2$), inclusion of sulfite or ethanol at different concentrations. The selection of conditions matched the enrichment when microorganisms were isolated from enriched samples.

In some cases, oxygen-utilizing microorganisms may be desired and can be enriched and isolated by a variation of the method. For microorganisms that do not grow in the absence of oxygen, all phases of enrichment and isolation would be conducted in open containers with air or oxygen bubbled in or in a shaking bath. Isolated colonies can be selected from agar plates rather than roll tubes. Some additives, such as $Na_2SO_3$, prevent fermentation and can be used to select against acid producers. It may be desirable to isolate an oxygen-utilizing microorganism to produce a certain fermentation product under anaerobic conditions. For example, an oxygen-using microbe might produce an alkyl alcohol under anaerobic conditions (e.g. yeast). The microorganism could be grown easily in air on the substrate it uses, but caused to make the product by enclosing the environment from air. Enrichment and isolation of such a microorganism would be initiated by enrichment in an aerobic phase. The microorganism would be grown on the substrate that one desires to degrade (e.g. cellulose, complex plant cell wall, lignin), and from these organisms further enrichment of those organisms that can grow on the product desired (e.g. ethanol, propanol, butanol). At this time, microorganisms remaining have the machinery to use the product and convert it to $CO_2$ and $H_2O$, and to completely degrade the feedstock, and grow under these aerobic conditions. Finally, organisms would be isolated under anaerobic conditions by growing them on the feedstock that one wishes to degrade. The conditions would be determined to be thermodynamically favorable to produce the desired product. The survivors would be microorganisms that degrade the substrate to the product, and survive anaerobic conditions. This method was used to isolate fiber-digesting, ethanol-tolerant ethanol-producing microorganisms in one example, but can be used for many other feedstocks (e.g. lignin, pectin, starch) and products (e.g. other alcohols, VFA, aldehydes, ketones). The requirement of the product is that it results from partial degradation and metabolism of the feedstock, the microorganism having been able to grow from the energy it derives from orchestrating that conversion.

The key principle behind this process is that all enzymes catalyze reactions in both forward and reverse directions but the reaction flows spontaneously in the direction dictated by thermodynamics. Therefore, the ability to degrade a feedstock to $CO_2$ and $H_2O$, or to degrade a product (e.g. alcohol) to $CO_2$ and $H_2O$, indicates a joining of the metabolic pathways that can be exploited by changing the concentrations of products and reactants to influence the underlying thermodynamics. The ability of a microorganism to capture energy and grow using these pathways may be easily calculated for different conditions and advantageously used in accordance with the present invention.

Isolation of microorganisms is the preferred method of producing the culture of microorganisms to digest plant biomass to ethanol as described in accordance with the present invention. Generally, the isolated culture is tested or screened by digesting and fermenting feedstock under the conditions described (including high $H_2$) which increase the portion of biomass carbon converted to ethanol carbon.

Although the present invention is based upon the selection and use of naturally-occurring microorganisms, it is also specifically contemplated that these microorganisms may also be further improved using classical microbiological methods such as mutagenesis, or modem molecular techniques such as knock outs, knock downs of genes encoding for enzymes necessary to produce undesired products (i.e. acetate kinase), or to increase ethanol or other alkyl alcohol production.

Example

Enrichment and Isolation of Ethanol-Producing Microorganisms

Anaerobic Microorganisms to Produce Ethanol from Plant Fiber

Several anaerobic microorganisms were isolated that degrade various forms of plant fiber to produce ethanol directly. The desired characteristics for these organisms were the following:

1. Ethanol tolerant to at least 5% ethanol concentration, and preferably to 8% or 10% ethanol concentration as unit weight per volume of fluid. Higher tolerance to ethanol allows the microorganism to produce ethanol to a high enough concentration that the resultant liquid can be distilled at low cost to recover the ethanol.
2. Ability to produce ethanol when ethanol concentration exceeds 5% of liquid, or preferably, 8 to 10% of liquid or greater.
3. Ability to convert a significant portion of the digested biomass to ethanol. For example, they should convert at least 30%, and preferable at least 50% by weight, of the digested biomass to ethanol, or greater. This ability requires the enzymes for ethanol production, but also requires the means to prevent other enzymes from degrading the metabolites to other products. For example, organic acids may be produced instead of ethanol unless these pathways are inhibited or missing from the microbial culture.
4. Ability to digest various forms of biomass comprising cellulose, hemicellulose, and pectin. Alternatively, they may digest starch and be used for a different process, or the microbial culture may be able to digest both plant fiber and starch and be used for a non-homogenous feedstock. This ability would require the production of enzymes for the digestion process, and the regulation of the genes encoding those enzymes to favorably digest the substrate.
5. The ability to grow while producing ethanol in high ethanol concentration. The thermodynamic calculations show that only about half as much energy can be produced by anaerobic organisms making ethanol as one making acetic acid, so growth rate may often be an issue, and be addressed by using organisms with survival strategies against high dilution rates, and engineering principles to maintain slow-growing organisms.

In addition to these primary traits, additional and preferred traits include the following:

6. Ability of the organism to attach to cellulosic substrate. During digestion, attached organisms producing $CO_2$ cause the digesting biomass to float. These organisms can digest biomass readily because of their close proximity to it, and they do not wash out of the digester with the fluid phase.
7. Motility could also be advantageous as a means to allow organisms to populate new substrate, and having motile microorganisms might decrease the need for mechanical mixing.
8. Catalase and peroxidase enzymes can make microorganisms tolerant to oxygen which can be advantageous because it would be easier to handle the microorganisms.
9. Ability to utilize oxygen to grow may be advantageous. Oxygen-utilizing microorganisms can be used to decrease the oxygen content of the media and make the environment more favorable to strict anaerobes, which might also be used. Open air conditions might be used to grow oxygen-utilizing organisms in a separate phase of the digestion, and the greater number of these organisms may make further digestion and fermentation possible under subsequent anaerobic conditions.

The enrichment and isolation (roll tube) conditions for the first 243 isolates of organisms to produce cellulosic ethanol are shown in Table 1 below.

Media for enrichment, isolation, screening and initial experiments was as described for in vitro digestion by Goering and Van Soest, 1970, except carbonate and bicarbonate salts (e.g. $NaHCO_3$, $NH_4HCO_3$) were replaced with equimolar phosphate salts (e.g. $NaH_2PO_4$, $NH_4H_2PO_4$) adjusted to pH 6.8. Macro minerals, microminerals, tryptic digest of casein, ammonia, sulfide and cysteine reducing agents, and resazurin were used according to Goering and Van Soest, 1970. Media was boiled under 1 atm $CO_2$ or $N_2$ (for $H_2$ preparations) gas. The same media formula was used for initial enrichment, agar roll tubes, broths, slant tubes, and agar plates.

However, roll tubes, slant tubes and agar plates also contained 2% agar gel (BactoAgar). Media used for pure cultures (everything but the initial enrichment) was combined with 20% autoclaved rumen fluid to provide potential unknown growth factors.

Enrichment.

Media usually contained 2% of a pure form of cellulose, AVICEL® (microcrystalline cellulose), for enrichment, and sometimes contained arabinose and xylose as indicated in Table 1. Media (45 ml) was transferred to each 140 ml bottle under perfusion of oxygen-free gas, i.e., $CO_2$ or $H_2$. Rumen fluid from the cow's rumen was initially prepared by blending for 1 minute and straining though cheese cloth followed by glass wool. Carbon dioxide, run through a copper column to remove $O_2$, was perfused over rumen contents and into containers to maintain anaerobic conditions.

Rumen inocula (5 ml) was added to each flask. Flasks were sealed with butyl rubber stoppers and incubated in a shaking water bath for 48 hours. New flasks were prepared with 45 ml of media with cellulose, and 5 ml of subculture was added from the previous fermentation. These flasks were again incubated for 48 h, and again subsampled. Each enrichment process included at least three cycles of subculturing and growth.

For each enrichment and roll tube, the temperature of incubation was 39° C. unless indicated otherwise. Organisms were also selected at 55° C. and other temperatures could have been used. Initially, various concentrations of ethanol were used with cellulose (AVICEL® (microcrystalline cellulose)) as substrate and $CO_2$ as headspace gas. These conditions select for organisms that can utilize ethanol, and which therefore also have the enzymes to make ethanol. Later $H_2$ was used as headspace gas with different concentrations of acetic acid. These conditions select for acetic acid tolerant microbes, but conditions favor microorganisms that make ethanol rather than acids. In one case (112-117), sulfite ($SO_3$) and air were used in the enrichment with 1% ethanol as the only substrate (no tryptic digest of casein). These conditions select for organisms that use oxygen, and can make or degrade ethanol. Sulfite appears to inhibit organisms with hydrogenases (e.g. acid producers). Initially when rumen fluid was incubated with 0, 4, 6, 8, 10 or 12% ethanol and 2% cellulose, microbial growth was inhibited at greater than 6% concentration. However, after three enrichments in 6% concentration, these cultures were transferred to 10% ethanol, in which they grew, and were enriched for three more cycles (numbers: 15-22, 71-82).

Isolation.

Roll tubes used the same media as for enrichment, but it also contained, 0.8% cellobiose, 2% agar and 20% strained rumen fluid. Some tubes contained 5-carbon sugars. The prepared media (5 ml) was transferred to sterile test tubes while still hot from boiling. Tubes were cooled to 55° C., and inoculated. Subcultures from the last enrichment were diluted serially in media to obtain cultures from 1 to $10^{-14}$ viable cells per 0.5-ml inocula. Roll tubes were prepared for each level of dilution, but concentrating on the $10^{-10}$ to $10^{-14}$ dilutions. Once inoculated, tubes were perfused with gas, stoppered, and rolled on ice to make the gel harden. Tubes were incubated for 24 to 48 h at 39° C. and independent colonies selected from these. Only organisms that can grow on cellobiose were selected in the roll tubes, in the present case, and indicators in the roll tube agar were used to identify acid-producing and non-acid-producing strains. Whereas, only fiber digesting microbes can use cellobiose, these isolates represented fiber digesters.

Maintenance.

Colonies were selected from among the colonies in roll tubes and transferred to broth for short-term maintenance. The broth was of the same composition as media for other purposes, but did not contain agar, and contained 0.8% cellobiose and 0.4% of each xylose and arabinose. Broth cultures are maintained at 39° C. until they become cloudy. Broth cultures (5% final concentration, vol/vol) are transferred to new media three times per week. After two to three cultures, 0.1 ml culture is transferred to a slant culture (2% agar media with 0.8% cellobiose in a 25-ml tube with 10 ml media on a slant to increase surface area). The inocula is added on top the agar which is maintained under $CO_2$, $N_2$ or $H_2$. These are initially incubated at 39° C. until colonies form (16 h), and then stored at 25° C. or 4° C. for up to a month. Cloudy broth cultures are also stored by adding 30% glycerol (final volume) and freezing in liquid nitrogen; once frozen, these colonies are stored at −80° C.

Screening. Screening of microorganisms addresses whether they can digest a certain substrate and convert it to ethanol. For ease of use, soluble cellobiose or AVICEL® (microcrystalline cellulose) are frequently used. Cellobiose is a two-glucose unit of cellulose, which is generally not utilized by non-fiber degrading microorganisms. The 243 isolates derived as described were screened by transferring 0.5 ml broth to 9.5 ml media (as described, no agar) with final concentration of 0.8% cellobiose and 0.4% of each arabinose and xylose (5-C sugars). Samples were also screened using 2% cellobiose, 6% cellobiose, 2% AVICEL® (microcrystalline cellulose), and 0.8% cellobiose with no 5-C sugars or digest of casein, and 0.4% of each 5-C sugar but no digest of casein. Samples were also incubated with and without initially including 6% ethanol in the media. The cell growth was determined by turbidity, and ethanol was measured by gas chromatography (GC) at time=0, and other time points (e.g. 6 h, 1 d, 3 d, and 5 d). Results showed that many strains could produce ethanol from cellobiose or cellulose. Several strains increased ethanol concentration significantly above the 6% initially inoculated.

TABLE 1

Conditions to enrich and isolate ethanol-producing fiber-digesters.

| | Enrichment | | | Roll Tube | |
| --- | --- | --- | --- | --- | --- |
| Isolates | Ethanol Addition | Substrate | Other | Substrate | Indicator (Bromcresol purple) |
| 1 to 14 | 6% | Cellulose | 1 atm $CO_2$ | Cellobiose | |
| 15 to 22 | 10% | Cellulose | 1 atm $CO_2$ | Cellobiose | |
| 23 to 36 | 0% | Cellulose | 1 atm $CO_2$ | Cellobiose | |
| 37 to 59 | No enrichment | Cellulose | 1 atm $CO_2$ | Cellobiose + 5C | |
| 60 to 70 | 0% | Cellulose | 1 atm $CO_2$ | | |
| 71 to 82 | 10% | Cellulose + 5C | 1 atm $CO_2$ | | |
| 83 to 111 | 6% | | 55° C. | | |
| 112 to 118 | 1% | Cellulose | Air, $Na_2SO_3$ | | |
| 119 to 152 | 0% | Cellulose | 2 atm $H_2$ | | |
| 153 to 177 | 0% | Cellulose | 100 mM acetic acid, pH 6.8, 2 atm $H_2$ | | |
| 178 to 184 | 0% | Cellulose | 2 atm $H_2$ | | |
| 185 to 215 | 0% | Cellulose | 2 atm $H_2$ | | |
| 216 to 218 | 0% | Cellulose | 100 mM acetic acid, pH 6.8, 2 atm $H_2$ | | |
| 219 to 222 | 0% | Cellulose | 100 mM acetic acid, pH 6.8, 2 atm $H_2$ | | |
| 223 to 228 | 0% | Cellulose | 100 mM acetic acid, pH 6.8, 2 atm $H_2$ | | |

TABLE 1-continued

Conditions to enrich and isolate ethanol-producing fiber-digesters.

| Isolates | Enrichment | | | Roll Tube | |
|---|---|---|---|---|---|
| | Ethanol Addition | Substrate | Other | Substrate | Indicator (Bromcresol purple) |
| 229 to 243 | 0% | Cellulose | 100 mM acetic acid, pH 6.8, 2 atm $H_2$ | | |

5C = 5-carbon sugars (xylose and arabinose, 1% each for enrichment, or 0.4% each for roll tubes).
Cellulose = 2% AVICEL ® (microcrystalline cellulose).
Cellobiose = 0.8%.
Bromcresol indicator shows acid production (yellow) or not (purple).

Example

Enrichment and Isolation of Butanol-Producing Microorganisms

As a proof of the concept that the methods of isolation also work for other alcohols besides ethanol, rumen microbes were enriched for butanol tolerance by growing them on 2% AVICEL® (microcrystalline cellulose) in 4% or 5% butanol by volume. In this case, each growth phase was 3 days instead of 2 days before subculturing and repeating, and 10 cycles of enrichment were used instead of only a few. In other respects the enrichment was similar to that used for ethanol producers. In this first case, $CO_2$ gas was used in the headspace, but other gases may be preferred when selecting for butanol producers. As previously with ethanol, one way to select for alcohol producers is to provide conditions for alcohol degradation, and then reverse the conditions to cause them to produce alcohol. Hungate roll tubes used similar conditions to isolate individual colonies.

Seven isolates from this procedure grew in media with as much as 6% butanol by volume and produced butanol from cellobiose. These microorganisms and this process for butanol production from cellulosic biomass is an improvement to available microorganisms and processes because cellulosic biomass can be converted directly to butanol, and the organisms tolerate greater concentrations of butanol than existing methods which use microorganisms to convert glucose to butanol. Interestingly, these organisms were also tolerant to as much as 10% ethanol, and media with butanol in it was subsequently used as a means to select for ethanol tolerant microorganisms. Only one of the organisms isolated to produce butanol (instead of ethanol) was identified genetically. It was identified as a member of the genus *Pediococcus* and its 16S rDNA base pair sequence was more than 99% identical to *P. acidilactici* or *P. pentosaceus*.

The thermodynamic analysis demonstrated that butanol and propanol production in the presence of high concentrations of those respective alcohols is typically not thermodynamically feasible or favorable. By manipulating those conditions in mixed rumen cultures, alkyl alcohol concentrations increased, and microorganisms that carry out those reactions were isolated. Thus, the similar procedures described for ethanol can also be used to select for microorganisms that produce high concentrations of butanol or propanol. With more time, the same procedures as used for ethanol production will develop microorganisms with tolerance to even higher butanol or propanol concentrations, the ability to produce these alcohols in the presence of higher alcohol concentrations, and the ability to convert a greater percentage of biomass to butanols or propanols.

Most of the isolates produced ethanol when incubated with 2% or 6% cellobiose or 2% AVICEL® (microcrystalline cellulose) under $H_2$ pressure (1 to 2 atm). Microorganisms isolated under $H_2$ pressure or air and sulfite did not respond to use of $H_2$ in the headspace. That is, they produced ethanol to a similar extent whether or not $H_2$ was present. Microorganisms that have hydrogenases may be shifted to produce ethanol by adding $H_2$, CO, $SO_3$ or other inhibitors of hydrogenases, but these are not needed for isolates that are selected under these inhibitors because such selection obtains microorganisms that do not have this option of metabolism.

Clearly, microorganisms that produce ethanol from plant fiber are abundant in nature; many of these organisms are ethanol tolerant, and many produce ethanol as a major product. In natural cultures, ethanol is converted to lower energy end products (e.g. acetic acid), but in pure culture or in the presence of methane inhibitors or other means to inhibit $H_2$ production or utilization, such organisms produce ethanol. Moreover, in using the screening or testing methodologies described herein, one skilled in the art may readily obtain microorganisms suitable for use in accordance with the present invention.

Testing of Microorganisms

Once isolated, microorganisms were maintained and tested for their ability to grow on cellulose (AVICEL® (microcrystalline cellulose)), cellobiose, or arabinose and xylose. Similar medium as used for the Hungate roll tubes was used. Organisms were tested first in batch culture with 1-2% carbohydrate or 10% carbohydrate. They were incubated with or without added ethanol.

Candidate species were also incubated in continuous culture or continuous feeding using 1-2% AVICEL® (microcrystalline cellulose). Alternatively, organisms can be tested by incubating with the feedstock that one wishes to degrade (e.g hay, algae, manure). Gases are sometimes collected in mylar bags, and VFA and alcohols and gases were analyzed by gas chromotography.

Potential Production and Distribution of Microorganisms

The microbial isolates are stored at low temperature (e.g. −80° F. or in liquid $N_2$) and are maintained in broth and agar media. The most useful microorganisms isolated for the ethanol production process are produced using large-scale fermenters. A different fermenter for each strain is not the most cost-effective model for production. Experiments based on thermodynamic analysis will determine which microorganisms are likely to be used in mixed culture and the means to maintain all of them in the same culture. For example, two microorganisms using different substrates, may be maintained in co-culture by supplying both substrates. The microorganisms may be freeze-dried before distribution.

Thermodynamic Calculations

Calculation of the thermodynamic feasibility of making ethanol has been reported previously, but the process used as an aspect of this invention advances the thermodynamic analysis in many ways. Firstly, multiple thermodynamic equations were solved simultaneously to enable prediction of which pathway branches are available, and to integrate the effects of each reaction on each other. Secondly, microorganisms that can produce high concentrations of ethanol from plant fiber were used for the first time with thermodynamic conditions (e.g. concentrations, pressures, temperature) that enable production of ethanol at high concentration. For this reason, microorganisms for cellulosic ethanol production were discovered for the first time although they are common in nature. One aspect of maintaining these thermodynamic conditions is limiting certain pathways in the fermentation to maintain control of metabolite concentrations. Thirdly, the thermodynamics for conversion of cellulosic biomass to ethanol was calculated, and it is vastly different from fermentation of sugars by yeast. Yeast fermentation is driven by very high concentrations of glucose, but free glucose concentration does not need to be very high in the process to convert cellulose to ethanol, digestion of cellulose being a rate-limiting step. In nature, even low concentrations of glucose are converted to acids or other products so glucose does not accumulate. Higher concentrations may inhibit digestion. As long as these low concentrations can be used, by removing products of the fermentation, the process can be made to go forward. Fourthly, once a reaction may appear feasible (possible), it may still not be favorable relative to other reactions. For example, it may appear that ethanol can be made from a certain intermediate like glucose, but acetic acid may be more feasible. Then both reactants can be made, or organisms that make acetic acid may even thrive and out compete with those that make ethanol. Fifthly, thermodynamics can be applied to the fitness of organisms that carry out a given reaction relative to other organisms. If the $\Delta G$ for glucose to acetate is much more negative than for glucose to ethanol for a certain set of concentrations, organisms that make acetate will grow faster than those that make ethanol. To encourage ethanol production within an organism, or to encourage organisms that make ethanol to out compete with acetic acid producers, the concentrations must be manipulated to favor the ethanol producers and production of ethanol. Under these conditions, ethanol producers can be enriched, selected, mutated and manipulated.

Thus, the second law of thermodynamics is applied in a new way as an aspect of the present invention to better determine conditions for shifting fermentation toward desired products, to enrich and isolate desired microorganisms, and to thereafter genetically alter microorganisms to increase production of desired products.

The present inventors further disclose herein a mathematical model that enables users to establish the thermodynamic equilibrium for different microbial cultures, and identify control points. Established methods were used to determine the standard free energy change (60°) for important fermentation reactions. These reactions include conversion of glucose to: acetic acid, propionic acid, butyric acid, lactic acid, ethanol, propanol, butanol, methane, hydrogen, $CO_2$ and $H_2$.

The moles of ATP generated for each reaction were set to values described in the research literature (e.g. 2 ATP per VFA other than lactic acid, 1 ATP per ethanol or lactic acid). Based on research previously disclosed in U.S. Ser. No. 12/000,856, the model assumed equilibrium could be approached for production of $CH_4$ from $CO_2$ and $4H_2$ and for the degradation or synthesis of acetic acid to or from $2CO_2$ and $4H_2$. The interconversion of VFA and alcohols was also assumed to approach equilibrium. The model was solved for equilibrium concentrations of $CH_4$, $CO_2$, $H_2$, VFA, and alcohols using simultaneous equations in a spreadsheet. Equilibrium concentrations indicate what is thermodynamically feasible for set conditions. For example, this model calculates the concentration of ethanol relative to acetic acid that can be produced in the presence of 0.9 atm. $H_2$ pressure and 0.1 atm $CO_2$ pressure. Further, it enables users to calculate concentrations of other intermediates necessary to obtain a certain concentration of ethanol. Therefore, the model provided herein allows one to define the conditions that favor ethanol production; for example, 1 atm. $H_2$ may be required or only 0.01 atm. $H_2$ may be required depending on other metabolites in the reaction. Results of this model are described herein, and the approach thereof may be applied to many other uses, including other anaerobic or aerobic fermentations, or other aspects of metabolism.

III. Equilibrium Concentration of Ethanol, Propanol and Butanol Concentration Given Different Conditions in Mixed Culture, and Equilibrium for Methanogenesis and Acetogenesis Examplen Calculations from the Thermodynamic Model.

Although a model encoded with software provides much greater flexibility for exploring the potential to control a fermentation system, example calculations are presented in Tables 2 and 3. The change in free energy ($\Delta G$) under typical fermentation conditions is presented in Table 2. Note that more negative values indicate more thermodynamically favorable reactions. In Table 2, only the $CO_2$ and $H_2$ pressures were varied, but in the model, many other variables can also be changed including partial pressure of methane, pH, temperature, and concentrations of available glucose and other metabolites.

The accuracy of the model depends on how well the fermentation is defined in terms of what reactions are available in the system (what enzymes are present), the amount of ATP generated per reaction, the free energy of formation of each reactant and product, and the stoichiometry of the reactions. The free energy of formation is easily and readily obtained from standard text books. The stoichiometry of reactions, in some cases, may not be clear. For example, a glucose molecule and water molecule may yield 2 molecules of acetic acid and $4H_2$, and $2CO_2$ or a glucose molecule could yield 3 molecules of acetic acid, or both possibilities may exist depending on the organisms or the conditions. The number of ATP per reaction also varies and the fermentation system could enable more than one option for ATP production. Despite these uncertainties, the relative differences in the way each metabolite is affected by these conditions are clearly established.

In Table 2, under low $CO_2$ and low $H_2$, acetic acid is the favored metabolite. Note, also that degradation of acetic acid is also feasible, so if the fermentation contains acetate-degrading microorganisms, acetic acid would not necessarily accumulate. This degradation would need to be prevented to make acetic acid the main product. Alcohols are generally not favored, but the effect of $CO_2$ and $H_2$ on butanol production is relevant, and it is clear that low $CO_2$ shifts fermentation toward ethanol and butanol, and high $H_2$, shifts it away from acetic acid. Both butanol and ethanol have the most negative ΔG with low $CO_2$ and high $H_2$ conditions. However, propionate and methane synthesis would also be favored, and may need to be inhibited if that activity is present. The high $H_2$ conditions favor propanol. Thus, the thermodynamic analysis shows the means to shift metabolism toward alcohols and away from acids, and it shows which reactions compete for the substrates. In the fermentation system, only acetic acid may be produced until the $H_2$ and $CO_2$ pressures increase, which would result in a readjustment of the metabolism in favor of other metabolites. Increasing $CO_2$ pressure, would make acetic acid or ethanol less favored but does not effect lactic acid or propionic acid. Increasing $H_2$ pressure decreases favorability of acetic acid, but makes propionic acid more favorable.

A driving variable in some cases is the concentration of available glucose. The actual available glucose concentration is likely to be low when derived from cellulosic biomass because as soon as glucose is released to the solution, several microorganisms would take. it up and utilize it. If those microorganisms are able to catalyze a reaction that is most favored (most negative ΔG), they will be able to utilize very minute amounts of glucose. The organisms that catalyze less thermodynamically favorable reactions would need a higher concentration of glucose to obtain energy.

Given the large number of possible reactions in natural ecosystems, it is now clear why it is difficult to shift metabolism toward a single metabolite. However, an understanding of thermodynamics makes it possible to design conditions to favor a set of desired microorganisms, and by combining use of inhibitors and these conditions, greater control is made possible. Further, different sets of thermodynamically favorable conditions can be applied in series to eliminate one set of competing microorganisms at a time. affected. Thus, various combinations can be used to shift the fermentation from one metabolite to another.

The model as shown here can be used to calculate the conditions in which production of a desired metabolite will be favored. For example, many microorganisms produce both ethanol and acetic acid or lactic acid. Even though ethanol does not consume $H_2$ in the production from glucose, higher $H_2$ concentrations favor ethanol over acetic acid. On the other hand, there is no effect of $H_2$ on the ratio of ethanol to lactic acid, but low $CO_2$ pressure favors ethanol in this case. The exact quantity of either gas needed to produce ethanol at a desired concentration depends on the concentrations of other metabolites and temperature, as this model can calculate.

The present inventors have realized that others have not produced alkyl alcohols in high concentration from cellulosic biomass because the proper thermodynamic conditions have not been applied to microorganisms that can produce lower alkyl alcohol. These conditions must consider that concentration of released sugars may be low, so for ethanol or butanol $CO_2$ pressures must be low, and other pressures, i.e. $H_2$ may be high to inhibit other reactions. For propanol, high $H_2$ pressures are needed. An important aspect of the present invention pertains to applying concentrations of metabolites and gases that make it thermodynamically feasible or thermodynamically favorable to produce a desired alkyl alcohol even when the available sugars are low in concentration. The only way to convert a low concentration of sugar to a high concentration of lower alkyl alcohol is to make the reaction thermodynamically feasible, if not favorable. Such conditions are also needed to isolate desired microorganisms for such a process, and to direct evolution of new microorganisms. Thus, one aspect of the invention is to control the pressure of $H_2$ or $CO_2$ to shift fermentation metabolism, but another aspect is to control concentrations

TABLE 2

Gibbs free energy change (ΔG, kJ) for fermentation reactions under different partial pressures of $CO_2$ and $H_2$ at 39° C. More thermodynamically favorable reactions are identified by more negative ΔG.

| | | $CO_2$ = 0.01 atm | | | $CO_2$ = 1.0 atm | | |
| | | $H_2$ (atm.) | | | | | |
| Reaction | ATP | .0001 | .001 | .01 | .0001 | .001 | .01 |
|---|---|---|---|---|---|---|---|
| Glc + 2$H_2$O → 2Ac + 2$CO_2$ + 4$H_2$ | 4 | −200 | −176 | −152 | −176 | −152 | −128 |
| Glc + 2$H_2$ → 2Prp + 2$H_2$O | 4 | −155 | −167 | −179 | −155 | −167 | −179 |
| Glc + 2$H_2$ → 1Btr + 2$CO_2$ + 2$H_2$ | 4 | −179 | −167 | −155 | −155 | −143 | −131 |
| Glc → 2Lac | 2 | −103 | −103 | −103 | −103 | −103 | −103 |
| Glc → 2EtOH + 2$CO_2$ | 2 | −160 | −160 | −160 | −136 | −136 | −136 |
| Glc + 6$H_2$ → 2 PrOH + 2$H_2$O | 2 | −110 | −147 | −183 | −110 | −147 | −183 |
| Glc → 2BtOH + 2$CO_2$ | 3 | −156 | −156 | −156 | −133 | −133 | −133 |
| $CO_2$ + 4$H_2$ → $CH_4$ + 2$H_2$O | 1 | +18 | −6 | −30 | +6 | −18 | −42 |
| 2$CO_2$ + 4$H_2$ → Ac + 2$H_2$O | 0.2 | +50 | +26 | 2 | +26 | +2 | −22 |
| Ac + $CO_2$ + 3$H_2$ → Prp + 2$H_2$O | 0 | +22 | +4 | −14 | +10 | −8 | −26 |
| 2$CO_2$ + 6$H_2$ → EtOH + 3$H_2$O | 0.2 | +105 | +70 | +34 | +81 | +46 | +10 |
| Ac + 2$H_2$O → 2$CO_2$ + 4$H_2$ | 0.2 | −32 | −8 | +16 | −8 | +16 | +39 |

Metabolites and their assumed concentrations: Glc = glucose, 1 mM; Ac = acetic acid, 50 mM; Prp = propionic acid, 20 mM; Btr = butyric acid, 15 mM; Lac = lactic acid, 50 mM; EtOH = ethyl alcohol, 50 mM; PrOH = propyl alcohol, 50 mM,; BtOH = butyl alcohol, 50 mM; $CH_4$ = methane, 0.5 atm, $H_2$O = 50M, pH = 6.5, Temperature = 39° C.

The equilibrium concentrations predicted by the model are shown in Table 3. This model assumes that each possible reaction is in equilibrium. Of course, these would not be the actual concentrations in most fermentations, but rather the ratios indicate the direction the metabolites would flow in. Again, only $CO_2$ and $H_2$ pressures were varied, and there are many other variables in the actual model. However, some ratios are unaffected by either gas, and others are strongly of metabolites, including gases, relative to each other and relative to temperature to create conditions which are thermodynamically favorable. The effect of $H_2$ or $CO_2$ pressure on metabolism has appeared inconsistent in the past, but the application of thermodynamics in accordance with the invention enables a predictable and consistent response.

When attempting to produce an alkyl alcohol from a very diverse mixed population of bacteria such as represented by all the equations of Table 3, conditions to produce alkyl alcohol exclusively are difficult to achieve. Low $CO_2$ and high $H_2$ appears to be the best option for ethanol or butanol production, but note that acetate degradation, and hence ethanol and butanol degradation would also occur. Thus, alkyl alcohols may not appear even if they are produced transiently. These conditions would be appropriate for isolation of ethanol and butanol producers, or for fermentation using cultures that do not contain acetate- or ethanol-degraders.

Ethanol synthesis from gases is possible with high $CO_2$ and high $H_2$, but so too are other reactions that use these gases such as methane production. Thus, the high $CO_2$ and high $H_2$ partial pressures would be optimal to enrich or isolate organisms for de novo ethanol synthesis, especially when inhibiting methanogens. The model thus quantifies the competition between alkyl alcohol production and methane synthesis or acetic acid degradation.

high that it results in increased VFA degradation. The preferred $H_2$ concentration also depends on the $CO_2$ and $CH_4$ concentrations because they affect the equilibrium.

These preferred gas pressures may be provided in a number of different ways. For example, the fermentation may be continuously perfused with the desired gas concentrations, and in an industrial process, the gas composition may be adjusted by removing certain gases, and other gases could be recycled. The amount of added $H_2$ needed to maintain the desired composition can be calculated and added at that rate and adjusted as needed. The fermentation may occur in the presence of high $CH_4$ concentrations in order to decrease $CH_4$ production. The thermodynamic model described herein has demonstrated that about 10-25%, preferably about 20% by volume of $H_2$ and about 70-85%, preferably about 80% by volume of $CH_4$, is the most advantageous for ethanol production. Experimental

TABLE 3

Equilibrium ratios (mol/mol) predicted by the thermodynamic model for different partial pressures of $CO_2$ and $H_2$.

| | $CO_2$ = 0.01 atm | | | $CO_2$ = 1.0 atm | | |
| | $H_2$ (atm.) | | | | | |
| Ratio | .0001 | .001 | .01 | .0001 | .001 | .01 |
|---|---|---|---|---|---|---|
| Methane, atm | $5 \times 10^{-4}$ | $5 \times 10^{0}$ | $5 \times 10^{4}$ | $5 \times 10^{-2}$ | $5 \times 10^{2}$ | $5 \times 10^{6}$ |
| Prp:Ac | $7 \times 10^{-5}$ | $7 \times 10^{-2}$ | $7 \times 10^{1}$ | $7 \times 10^{-3}$ | $7 \times 10^{0}$ | $7 \times 10^{3}$ |
| But:Ac$^2$ | $2 \times 10^{-3}$ | $2 \times 10^{-1}$ | $2 \times 10^{1}$ | $2 \times 10^{-3}$ | $2 \times 10^{-1}$ | $2 \times 10^{1}$ |
| Lac:Ac | $8 \times 10^{-9}$ | $8 \times 10^{-7}$ | $8 \times 10^{-5}$ | $8 \times 10^{-7}$ | $8 \times 10^{-5}$ | $8 \times 10^{-3}$ |
| Lac:Prp | $1 \times 10^{-4}$ | $1 \times 10^{-5}$ | $1 \times 10^{-6}$ | $1 \times 10^{-4}$ | $1 \times 10^{-5}$ | $1 \times 10^{-6}$ |
| EtOH:Ac | $5 \times 10^{-4}$ | $5 \times 10^{-2}$ | $5 \times 10^{0}$ | $5 \times 10^{-4}$ | $5 \times 10^{-2}$ | $5 \times 10^{0}$ |
| EtOH:Prp | $6 \times 10^{0}$ | $6 \times 10^{-1}$ | $6 \times 10^{-2}$ | $6 \times 10^{-2}$ | $6 \times 10^{-3}$ | $6 \times 10^{-4}$ |
| EtOH:Lac | $6 \times 10^{4}$ | $6 \times 10^{4}$ | $6 \times 10^{4}$ | $6 \times 10^{2}$ | $6 \times 10^{2}$ | $6 \times 10^{2}$ |
| PrOH:Ac | $4 \times 10^{-8}$ | $4 \times 10^{-3}$ | $4 \times 10^{2}$ | $4 \times 10^{-6}$ | $4 \times 10^{-1}$ | $4 \times 10^{4}$ |
| PrOH:Prp | $5 \times 10^{-4}$ | $5 \times 10^{-2}$ | $5 \times 10^{0}$ | $5 \times 10^{-4}$ | $5 \times 10^{-2}$ | $5 \times 10^{0}$ |
| PrOH:Lac | $4 \times 10^{0}$ | $4 \times 10^{3}$ | $4 \times 10^{6}$ | $4 \times 10^{0}$ | $4 \times 10^{3}$ | $4 \times 10^{6}$ |
| BtOH:But | $5 \times 10^{-4}$ | $5 \times 10^{-2}$ | $5 \times 10^{0}$ | $1 \times 10^{4}$ | $1 \times 10^{6}$ | $1 \times 10^{8}$ |
| BtOH:Prp | $8 \times 10^{-11}$ | $8 \times 10^{-6}$ | $8 \times 10^{-1}$ | $8 \times 10^{-9}$ | $8 \times 10^{-4}$ | $8 \times 10^{1}$ |
| BtOH:Lac | $3 \times 10^{-14}$ | $3 \times 10^{-8}$ | $3 \times 10^{-2}$ | $7 \times 10^{-5}$ | $7 \times 10^{1}$ | $7 \times 10^{7}$ |
| PrOH:EtOH | $7 \times 10^{-5}$ | $7 \times 10^{-2}$ | $7 \times 10^{1}$ | $7 \times 10^{-3}$ | $7 \times 10^{0}$ | $7 \times 10^{3}$ |
| BtOH:EtOH$^2$ | $4 \times 10^{0}$ | $4 \times 10^{0}$ | $4 \times 10^{0}$ | $4 \times 10^{0}$ | $4 \times 10^{0}$ | $4 \times 10^{0}$ |
| Ac Syn if less: | $2 \times 10^{-10}$ | $2 \times 10^{-6}$ | $2 \times 10^{-2}$ | $2 \times 10^{-6}$ | $2 \times 10^{-2}$ | $2 \times 10^{2}$ |
| EtOH Syn if less: | $1 \times 10^{-13}$ | $1 \times 10^{-7}$ | $1 \times 10^{-1}$ | $1 \times 10^{-9}$ | $1 \times 10^{-3}$ | $1 \times 10^{3}$ |
| Ac degr if greater: | $2 \times 10^{-7}$ | $2 \times 10^{-3}$ | $2 \times 10^{1}$ | $2 \times 10^{-3}$ | $2 \times 10^{1}$ | $2 \times 10^{5}$ |

Ac = acetic acid, Prp = propionic acid, Btr = butyric acid, Lac = lactic acid, etOH = ethyl alcohol, PrOH = n-propyl alcohol, BtOH = n-butyl alcohol, syn = synthesis from $CO_2$ and $H_2$ when product is less than molar concentration indicated, degr = degradation to $CO_2$ and $H_2$ when reactant is greater than molar concentration indicated.

Approaches to shifting the fermentation toward ethanol include using methanogen inhibitors (as described in U.S. Ser. No. 12/000,856), or shorter fermentation or faster dilution rates to select against methanogens, or culturing with defined cultures of microorganisms that exclude either methanogens or acetate degraders or both (exclusion of either would be sufficient). Thus, the present inventors isolated several biomass digesting microorganisms from the rumen that can be used to digest and ferment feeds to efficiently make ethanol without making methane or degrading acetic acid.

The present inventors also adapted the process for biomass degradation to ethanol to maintain just the right amount of $H_2$ and $CO_2$. The thermodynamic model shows that there is an optimal concentration of $H_2$ and $CO_2$ where ethanol production is favored over volatile fatty acids, but where acetate degradation would not occur at the acetate concentrations in the media. For example, the $H_2$ concentration should be higher than would occur when the fermentation maintains the naturally-produced gases, but not so results showed the greatest ethanol production at these ratios, compared to 100% $CH_4$, 100% $H_2$ or a 50:50 mix of $CH_4$ and $H_2$.

The observation that high $H_2$ pressure increases degradation of VFA may also be used in digesters to make methane. The methane may be made from $CO_2$ and $H_2$ produced in the degradation of glucose equivalent to acetic acid, and from the degradation of acetic acid to $CO_2$ and $CH_4$. An important disclosure of U.S. Ser. No. 60/871,441 and U.S. Ser. No. 12/000,856 was that removing $H_2$ was a way to accelerate digestion of substrate including VFA, so the fact that adding $H_2$ has the same effect is surprising.

The inventors contemplate adding a source of $H_2$ to accelerate degradation of biomass to produce methane, as well as removing $H_2$ to increase degradation of biomass to produce more $H_2$. Both approaches have potential added costs and benefits. In the first case (adding $H_2$), the faster fermentation to $CH_4$ and decreased need for $CO_2$ removal (less $CO_2$ would be produced) would have to outweigh the cost of $H_2$ to produce $CH_4$, a less valuable gas per unit of converted energy. In the latter case (removing $H_2$), the faster fermentation and production of more valuable fuel ($H_2$) at greater efficiency (less heat is produced) must outweigh the cost of separating low concentrations of $H_2$. The model predicts the conditions for both processes, and enables quantification of impacts from adding or removing different amounts of $H_2$, and the impact of removing some types of activity like production of methane or acetate from $CO_2$ and $H_2$.

Additional equilibrium concentrations were calculated to represent addition or removal of $H_2$ or increased total pressure of the fermentation (Table 4). These values may vary from observed values because of uncertainties of efficiencies, however the trends in concentrations relative to other metabolite concentrations depend on known stoichiometry, and thus are more certain. The predictions show, for example, the impact of adding or removing $H_2$ to establish new $H_2$ concentrations on methane production and acetate degradation or production. For example, removing $H_2$, as described in U.S. Ser. No. 12/000,856 and 60/871,441 is represented in the far left column and shows the greater degradation of acetic acid and capture of more energy as removed $H_2$ rather than $CH_4$ or other VFA. Increasing $H_2$ increases $CH_4$ production. The amount (moles) of $H_2$ removed or added can also be calculated from stoichiometry using the model. Although the effects on $CH_4$ production are opposite for increasing or decreasing $H_2$, acetic acid degradation increases for both effects.

ethanol. Propanol would be driven forward by provision of $H_2$ because $H_2$ is a co-substrate for propanol. An example of calculations for determining thermodynamically feasible conditions for microorganisms that produce alcohols and grow on low concentrations of available sugars is provided below.

The present inventors calculated the $CO_2$ or $H_2$ concentrations needed to make conversion of cellulosic biomass to ethanol, butanol or propanol thermodynamically feasible. Two parameters are needed which are not readily obtained: the available glucose concentration and the inefficiency (i.e. the threshold $\Delta G$ value at which the system can no longer carry out the reaction). These calculations assume a $\Delta G$ of $-125$ kJ per mole of glucose converted to account for inefficiency of microbial maintenance and growth and 1 mM glucose would be unconverted. The inefficiency was estimated from similar fermentation systems based on observed product and reactant concentrations at equilibrium. Different efficiencies may be determined for different systems, and these differences would shift the results but the same principles would apply. Empirical results obtained by the present inventors have confirmed that greater ethanol can be produced when $CO_2$ is continually removed.

For the reactions:

Glc→2EtOH+2$CO_2$ $G°312$=−208 kJ, 2 ATP

Glc→2BtOH+2$CO_2$ $G°312$=−266 kJ, 3 ATP

TABLE 4

Selected equilibrium pressures and concentrations when partial pressures of gases are manipulated.

| Item | Total pressure = 1 atm. | | | | Total pressure = 2 atm | | | |
|---|---|---|---|---|---|---|---|---|
| $CO_2$, atm. | 0.95 | 0.75 | 0.50 | 0.25 | 0.05 | 1.90 | 1.0 | 0.10 |
| $CH_4$, atm. | 0.05 | 0.25 | 0.50 | 0.75 | .95 | 0.10 | 1.0 | 1.90 |
| $H_2$, atm | $1.0 \times 10^{-4}$ | $1.6 \times 10^{-4}$ | $2.2 \times 10^{-4}$ | $2.8 \times 10^{-4}$ | $4.5 \times 10^{-4}$ | $1.0 \times 10^{-4}$ | $2.2 \times 10^{-4}$ | $3.8 \times 10^{-4}$ |
| Ac deg if greater: | $2 \times 10^{-3}$ | $8 \times 10^{-3}$ | $1 \times 10^{-2}$ | $8 \times 10^{-3}$ | $2 \times 10^{-3}$ | $8 \times 10^{-3}$ | $4 \times 10^{-2}$ | $4 \times 10^{-3}$ |
| Ac syn if less: | $2 \times 10^{-6}$ | $9 \times 10^{-6}$ | $1 \times 10^{-5}$ | $9 \times 10^{-6}$ | $2 \times 10^{-6}$ | $9 \times 10^{-6}$ | $5 \times 10^{-5}$ | $4 \times 10^{-6}$ |

Model assumes pH = 6.5, temperature = 39° C.

The far right columns show the effect of increasing the total gas pressures. The higher total pressure does not affect the pressure of $H_2$, but $H_2$ becomes a lower percentage of the total gas. This of course is the opposite effect of decreasing pressure using application of vacuum (U.S. Ser. No. 12/000,856 and 60/871,441). The equilibrium concentrations of acetic acid increase with higher total pressure. Thus, increasing pressures shifts the fermentation toward greater acetic acid production (either from $CO_2$ and $H_2$, or by decreasing degradation) rather than production of methane and $H_2$. If acetate or ethanol are synthesized from $CO_2$ and $H_2$, or CO and $H_2$, higher total gas pressure to increase the partial pressure of synthesis gases would also shift metabolism toward greater concentration of acetic acid or ethanol.

Calculating Thermodynamically Feasible Conditions for Producing Lower Alkyl Alcohols The present inventors discovered that previous attempts to make alcohols from plant fiber using microorganisms did not use conditions within the digester to make alcohol production thermodynamically feasible. The inventors observed that they needed to remove headspace gases during digestion to make ethanol production proceed. Removal of one of the products, $CO_2$, shifts fermentation toward making more ethanol. The same would apply to butanol as $CO_2$ is a co-product of butanol fermentation as well and the thermodynamic analysis shows it is limited in the same way as where $G°312$ is the change in free energy under standard conditions (1 M concentration of solutes, and 1 atm. pressure of gases, and temperature 312 K). The pressure of $CO_2$ is determined by solving the following equation:

$$\Delta G = \Delta G° + \ln RT ([\text{Products}]/[\text{Reactants}])$$

where R is the gas constant, T is temperature in degrees Kelvin, and brackets [ ] indicate molar concentrations or partial pressures in atmospheres of the product of all products and product of all reactants, $\Delta G$ is set to −125 kJ for maintenance and growth of microorganisms (inefficiency), and 44 kJ is added per ATP molecule produced. The equation is solved using glucose and alkyl alcohol concentrations to determine partial pressure of $CO_2$.

The equilibrium ratio of the products to reactants is therefore constant as defined by Gibbs free energy, and having thus defined the adjustment in free energy due to inefficiency (125 kJ), and having set the concentrations of glucose (1 mM) and alcohols (4%), the concentration of $CO_2$ required in the fermentation to reach these conditions can be determined to be 1.1 atm. for butanol, and 0.5 atm for ethanol. To achieve 6% concentration, the $CO_2$ pressure would need to be 0.9 atm for butanol, and 0.3 atm. for ethanol. Thus, $CO_2$ needs to be removed from the fermentation to concentrate ethanol or butanol production relative to available glucose with similar efficiencies.

If there are several pathways for glucose utilization, the glucose concentration may become very low, and alcohol can only be produced if they can compete with those low concentrations. If these other pathways are eliminated, there may be no need for conversion to glucose at low concentration, but high available glucose might inhibit further fiber digestion.

Where the glucose equivalent concentration is permitted to build up using defined cultures, the removal of $CO_2$ is not as important, but removing $CO_2$ is one way to increase alcohol concentration with low concentrations of glucose. Previous attempts to produce alcohols from plant fiber did not remove enough $CO_2$ to make it thermodynamically feasible to produce ethanol or butanol if those organisms need to be maintained and grow. Isolating organisms that produce less ATP or require that less energy be captured for maintenance and growth during ethanol production would enable concentration of alcohols at lower partial pressures of $CO_2$, but it would still be more feasible to produce ethanol or butanol with lower $CO_2$ pressure. For the reaction:

$$Glc + 6H_2 \rightarrow 2PrOH + 2H_2O \quad \Delta G°_{312} = -386 \text{ kJ}, 2 \text{ ATP}$$

High hydrogen pressure can drive propanol production. Using the same approach as for ethanol and butanol equilibrium concentrations, $H_2$ partial pressure would need to be 0.001 atm. for propanol accumulation to 4% from glucose equivalent of 1 mM.

The inventors have therefore provided examples of the conditions where alcohols can be produced in high concentration from biomass without producing high concentrations of available sugars. When alternate pathways are available to use available glucose, the glucose concentration could be lower than in these examples, and much lower $CO_2$ or higher $H_2$ concentrations may be needed to produce alcohols. The examples also vary depending on the efficiency of conversion by the organisms (threshold $\Delta G$ where process stops), but any fermentation system can be defined with respect to efficiency and glucose tolerance based on empirical observation.

Thermodynamic Conditions for De Novo Synthesis of Alcohols or Acids

As shown in FIG. 1, the inventors specifically contemplate isolation and use of microorganisms that synthesize alkyl alcohols, such as ethanol, from $CO_2$ and $H_2$ or CO and $H_2$. The inventors demonstrated that not only is de novo synthesis a possibility, but also that degradation of acetic acid and ethanol can be carried out by the same microorganisms and the same enzymes. Whether ethanol or acetic acid are created from $CO_2$ and $H_2$ or degraded to $CO_2$ and $H_2$ depends on thermodynamics, and concentrations of reactants or products. If the partial pressure of gases is high relative to the concentration of ethanol or acetic acid, the equilibrium will be shifted toward synthesis of ethanol or acetic acid rather than degradation.

There are two ways in which the thermodynamic analysis shows it is possible to shift metabolism toward synthesis of a desired alcohol or acid. The first way is the change the pressure of all gases, for example to increase total gas pressures, so that the partial pressure of $CO_2$ and $H_2$ are affected. Increasing the partial pressure of all gases this way increases the concentration to which alcohols or acids can be synthesized from gases. Decreasing the partial pressure of all product gases increases the degradation of acetic acid or ethanol. The second way to increase synthesis of alcohols or acids is to adjust the ratio of synthesis gases to an optimal ratio.

The second law of thermodynamics enables calculation of which direction a pathway flows and whether energy is required or can be captured by carrying out the reaction. The relationship is determined by the sign and magnitude of the change in free energy ($\Delta G$) from the following equation: $\Delta G = G° + RT \ln \{[Products]/[Reactants]\}$ where [Products] or [Reactants] represents the multiplicative product of the concentrations or partial pressures of solutes or gases. A simplified set of equations can be derived from the equations representing change in Gibbs free energy. According to the second law of thermodynamics, the direction of reactions depends on the concentration (e.g. atmospheres of gases or molarity of solutes), and other factors that can be considered constants for the present situation with a known reaction at a constant temperature, e.g. temperature (T), gas constant (R), $\Delta G°$.

For the following reactions:

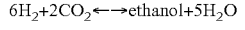

$$6H_2 + 2CO_2 \leftrightarrow \text{ethanol} + 5H_2O$$

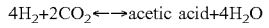

$$4H_2 + 2CO_2 \leftrightarrow \text{acetic acid} + 4H_2O$$

The ratio of $H_2$ to $CO_2$ used is 3:1 for ethanol or 2:1 for acetic acid.

The relative change in favorability of ethanol or acetic acid synthesis relative to degradation at a constant total pressure is represented as the product of partial pressures of reactant gases. For example, for ethanol this product is $[H_2]^6 \times [CO_2]^2$ and for acetic acid this product is $[H_2]^4 \times [CO_2]^2$. If the total gas pressure is maintained at 1 atm, as the $H_2$ pressure increases from 0 atm to 1 atm the $CO_2$ partial pressure would decrease from 1 atm to 0 atm. The product of reactant gases for synthesis would initially increase and then decrease for both ethanol and acetic acid, with this product peaking at 0.667 atm $H_2$ for acetic acid, and at 0.75 atm for ethanol (FIG. 3). This result is relatively simple to find using algebra and calculus, or by simulation for different pressures of $H_2$ and $CO_2$.

Although temperature and total pressure affects the extent to which ethanol or acetic acid can be concentrated, the optimal ratio of gases to maximize the concentrations of ethanol or acetic acid under any given set of conditions is constant. This finding shows that if one desires to promote de novo synthesis of ethanol from $CO_2$ and $H_2$, the optimal ratio would be 3 moles of $H_2$ per mole of $CO_2$, and if one favors synthesis of acetic acid, the optimal ration would be 2 moles of $H_2$ per mole of $CO_2$. One way to increase ethanol synthesis from gases, is therefore to add or retain either $CO_2$ or $H_2$, or remove or utilize $CO_2$ or $H_2$ to leave gases in this optimal ratio. A way to increase degradation of ethanol or acetic acid is to manipulate $CO_2$ or $H_2$ away from these optimal ratios by either increasing or decreasing $CO_2$ or $H_2$.

Thermodynamics also shows that increasing total gas pressure is a means to increase both $CO_2$ and $H_2$ partial pressures, thereby increasing synthesis over degradation of ethanol or acetic acid. Concentrations of both ethanol and acetic acid that can be synthesized increase exponentially as the total gas pressures increase at a constant ratio of $H_2$ to $CO_2$ (FIGS. 4 and 5). However, exponent is 8 for ethanol and 6 for acetic acid corresponding to the stoichiometry of ethanol and acetic acid synthesis, which requires 8 or 6 moles of gas respectively to produce ethanol or acetic acid. Thus, the effect of pressure is exponentially greater for ethanol synthesis than for acetic acid synthesis (FIG. 6), where the exponent is 2. In other words, increasing total gas pressure when the gases are comprised of a similar concentration of $CO_2$ and $H_2$, shifts metabolism toward synthesis of both ethanol and acetic acid, but also shifts metabolism toward ethanol relative to acetic acid.

This theoretical principle can be applied to increase the efficiency of ethanol production from $CO_2$ and $H_2$, by using high total pressures to increase the ethanol concentration that can be derived from gases. It can also be used to enrich or select for microorganisms that synthesize ethanol rather than acetic acid, or to control microbial cultures that have access to both pathways. The inventors found empirically that when incubating with two atmospheres $H_2$ pressure, organisms were isolated that decreased total gas pressure while they fermented cellulosic substrate. These organisms synthesized additional ethanol from the added $H_2$ and the $CO_2$ released from degradation of cellulosic biomass to ethanol.

The same principles can be applied to mixtures of $H_2$ and carbon monoxide (CO). Similar calculations based on stoichiometry quantify that the optimal ratio of $H_2$ to CO is 2:1 for ethanol or 1:1 for acetic acid (FIG. 7). The effect of increasing pressure is the same as for synthesis of ethanol or acetic acid from $H_2$ and $CO_2$ (FIG. 8). Thus, adjusting gas formulations and increasing pressures would also shift metabolism toward greater ethanol synthesis or acetic acid synthesis when using CO and $H_2$ as well, or when selecting for microorganisms that can use these gases.

These principles were also applied to determine the optimal ratios for butanol or butyrate synthesis versus degradation, or de novo butanol synthesis versus butyrate synthesis. Butanol and butyrate can be produced from acetic acid by known microorganisms, so a microbial culture that assimilates gases into acetic acid could subsequently produce butanol or butyrate, or for that matter propanol or propionate. The optimal ratio of $H_2$ to $CO_2$ is 3:1 for butanol production or 5:2 for butyrate production (FIG. 9). Increasing total pressure at a constant ratio of gases increases butanol and butyrate synthesis concentration versus degradation concentration, and butanol concentration relative to butyrate (FIG. 10). The optimal ratio of $H_2$ to CO for butanol synthesis was 2:1, and the optimal ratio of $H_2$ to CO was 3:2 for butyrate synthesis. The effect of pressure was similar for $H_2$ and CO as for $H_2$ and $CO_2$.

These principles also apply to synthesis of propanol and propionate from gases (FIG. 11). The optimal ratio of $H_2$ to $CO_2$ is 3:1 for propanol synthesis or 7:3 for propionate synthesis. Increasing total pressure at a constant ratio of gases increases concentration where propanol and propionate synthesis occur and increases concentration where degradation occurs, and increases possible propanol concentration relative to propionate (FIG. 12). The optimal ratio of $H_2$ to CO for propanol synthesis was 2:1, and the optimal ratio of $H_2$ to CO was 4:3 for propionate production. The effect of pressure was similar for $H_2$ and CO as for $H_2$ and $CO_2$.

Multiplying the product of reactants shown in FIGS. 3 to 12 by a constant for each reaction gives the equilibrium concentration of the desired product (e.g. acetate or ethanol). This constant equals $e^{(-\Delta G° + \Delta G ATP)/RT} \times [H_2O]^n$ where n is the moles of water produced per mole of desired product. The constants vary among reactions depending on the amount of ATP produced by the process, but they are typically large numbers (e.g. $>10^5$), so the thermodynamically feasible concentrations are high for both alcohols and acids near the optimum for either acids or alcohols. In other words, under conditions near the middle of the graphs (FIGS. 3 to 12) either acid or alcohol production from gases is feasible.

Nonetheless, for many situations, the partial pressures relating to dissolved gases that are available to the fermentative organisms are near the extreme ends of the x-axes in the FIGS. 3 to 12. For example, in a natural anaerobic ecosystem, the $H_2$ concentration is very low, e.g. about 0.05% because it is readily used. If $H_2$ is perfused into the system, the dissolved $H_2$ reduces $CO_2$ so that dissolved $CO_2$ becomes very low. Thus, most fermentation systems move toward the ends of these figures where the concentrations of desired products can be limited by thermodynamics. When $CO_2$ pressure is high and $H_2$ is low, acids are favored over alcohols. When $H_2$ pressure is high and $CO_2$ pressure is low, alcohols are favored over the acids.

Therefore, perfusing high concentrations of $H_2$ into the fermentation favors alcohol synthesis over acid synthesis and may be a way to increase alcohol production and select for alcohol-producing microorganisms. If excessive $H_2$ is perfused, however, the $CO_2$ concentration will eventually decrease until neither acids nor alcohols can be synthesized.

When a ratio of $H_2$ to $CO_2$ is perfused into the incubation that is not optimal for the desired end product, one of two events must occur: 1) the metabolism will shift in order to use the excess gas, or 2) the accumulation of the desired product will stop because the gas mixture will shift toward a greater concentration of the excess gas as the limiting gas is used up. The first case occurs when an alternative pathway is available, and it will result in production of undesired product rather than the desired product. The second case would be especially limiting for microbial cultures with limited options for to shift to different end products. These organisms would appear to be intolerant to high concentrations of the product they produce. In fact, they would be limited thermodynamically at one end or the other of the previous graphs 3 to 12 (i.e. low $CO_2$ or low $H_2$). One means to select for organisms to produce a desired product from synthesis gases is to maintain the optimal ratio of gases for the desired product.

The described theory explains some empirical results obtained by the inventors. When incubating pure cultures with high $H_2$ pressures and cellulosic biomass, some microorganisms decreased gas volume and produced more ethanol than expected even with complete conversion of cellulosic biomass to ethanol and $CO_2$. Some also decreased acetic acid content. In these cases, ethanol was likely produced from the produced $CO_2$ and added $H_2$. Most produced $CO_2$ would be converted to ethanol, leaving the ratio of $H_2$ to $CO_2$ high and making degradation of acetic acid possible. This degradation would provide more $CO_2$ that could be converted to ethanol.

In every case, increasing gas pressures shifted metabolism toward higher synthesis concentrations, and away from degradation, and toward greater alcohol compared to the analogous volatile fatty acid concentration. The actual calculated concentrations are the optimal mixes for gases for each of these synthesis reactions, and one aspect of the invention is the use of thermodynamics and stoichiometry to calculate optimal ratios of gases for synthesis of desired products. Another aspect is the application of total gas pressures, such as greater than 1 atm or more, to increase the concentrations that alcohols or acids when produced from gases. This concept can be applied to any fermentation reaction in which a greater number of moles of reactant gases are used to produce a lower number of moles of product gases, and the reaction, like many fermentation reactions, is near equilibrium.

Continual Supply of Feedstock

Under some conditions, more than one end product is thermodynamically feasible, and one way to narrow the profile of obtained products is to decrease the reactant concentration so that only one product is feasible or merely preferred. For example, in the cow's rumen lactic acid is occasionally produced. It is toxic to the animal so it is not desired. One occasion where lactic acid builds up is when an animal consumes a slug of readily digestible starch. The rumen microorganism *Streptococcus bovis* was shown to shift its fermentation from acetic acid to lactic acid when subjected to high amounts of starch. Interestingly, lactic acid is not a thermodynamically favorable end product in the normal rumen. When glucose concentration is low, lactic acid cannot be produced because production of acetic acid is more favorable. Acetic acid can be produced with lower glucose concentrations than needed to produce lactic acid. However, when there is an abundance of glucose for both reactions, neither is limited by thermodynamics and both are produced, or lactic acid is produced because it proceeds faster, i.e., is kinetically favored.

A similar principle applies to the production of ethanol. Under conditions where both ethanol and acetic acid are feasible (e.g. high glucose concentrations) both can be produced. Or acetic acid may be produced because it provides more ATP. However, if glucose concentration is low, only the most favored pathway is available. Therefore, limiting substrate availability is another means to shift fermentation toward ethanol. Therefore, we are more likely to see fermentation at the end of a batch culture or when dilution rate or supply of substrate is slow in a continuous culture. Continuous feeding may be advantageous because the substrate can be added slowly without removing the microorganisms. It is thought by some that microorganisms do not produce ethanol during growth phase because they do not obtain enough energy for growth. This is probably a false conclusion based upon the observation that when microorganisms have an abundance of energy available, they grow fast and produce acids. The thermodynamic analysis shows that there is energy for at least 1 ATP per ethanol, which would promote growth at less than half the rate of acetic acid producers. As long as the conditions (e.g. $H_2$ pressure) are such that acetic acid is not feasible while producing 2 ATP, the microorganisms that can produce ethanol will out compete. The present inventors have disclosed that microorganisms can grow while producing mostly ethanol when under $H_2$ pressure. For some microorganisms, supplying the substrate continuously is necessary to maximize ethanol production. If substrate is supplied continuously, the microorganisms reproduce until they compete with each other enough to decrease the substrate available. Therefore, the continuous supply of substrate limits the carbohydrate available and shifts fermentation toward the most thermodynamically feasible pathway. Nonetheless, some microorganisms convert a fairly high percentage of biomass to ethanol even in batch cultures.

A microorganism such as *Streptococcus bovis*, for example, can also be manipulated to produce ethanol instead of acetic acid. In this case, high $H_2$ pressure and low $CO_2$ pressure would select against acetic acid and lactic acid, respectively. These conditions may be used to control the fermentation using *S. bovis*. Although *S. bovis* is a starch- or glucose-fermenting microorganism, if used in combination with fiber digesters, it can scavenge the available glucose and maintain conditions of low glucose concentration to shift fermentation toward ethanol. Cross feeding of various other microorganisms may also be used to increase ethanol production by both decreasing glucose concentration and directly producing ethanol.

Ethanol from Acetic Acid

The present inventors have also calculated the thermodynamic equilibrium for the pathways for ethanol production which indicated that there is no facile reaction path for acetic acid conversion to ethanol. Not including the free energy required or released from ATP utilization or generation, several atmospheres of $H_2$ pressure are needed to convert equimolar concentrations of acetic acid to ethanol. Under these extreme conditions, some microorganisms can do this, and can, in effect, turn vinegar back into wine. However, the microorganisms would be unlikely to obtain energy from doing so, and, therefore, their growth would depend on another process. At moderate $H_2$ pressures, microorganisms may use ATP to convert acetic acid to ethanol as a means to survive the $H_2$ pressures. Surprisingly, some isolated microorganisms that produced ethanol from cellobiose also decreased acetic acid from the initial concentrations in the media, and did not produce any other VFA measured. Thus, some of the microorganisms isolated for ethanol production can orchestrate this conversion.

If the pathway from acetic acid to ethanol is thermodynamically unfeasible with one atmosphere of $H_2$ pressure, why does digesting and fermenting biomass under one atmosphere $H_2$ pressure cause ethanol to be produced? The answer is based upon microbial ATP production and growth. The production of acetic acid produces an additional ATP compared with production of ethanol. Microorganisms in environments that have thermodynamic conditions enabling them to produce acids will produce acids because they can grow faster that way. Microorganisms that produce ethanol instead of acids only produce half as much energy per glucose equivalent. With only moderately high $H_2$ pressure, it becomes unfeasible to produce acetic acid and its extra ATP, thus ethanol is produced instead. This theory led the present inventors to discover further additional improvements to the process for producing ethanol and other lower alkyl alcohols from plant biomass. Clearly, it would be futile to select for a microorganism that can obtain energy for growth by converting acetic acid to ethanol. On the other hand, microorganisms that can make both ethanol and acetic acid would only be able to obtain energy by producing ethanol when grown under hydrogen pressure. Therefore, selecting for such microorganisms would be quite facile bearing the above in mind. Alternatively, based on subsequent experiments, acetic acid may have been converted to ethanol by microorganisms that grow on other biomass and make ethanol.

The present inventors disclosed in U.S. Ser. No. 12/000,856, an experiment which showed that ethanol was not produced from acetic acid. However, the amount of ethanol produced from glucose increased between 24 and 48 hours in batch culture. Since the glucose would have been fermented quickly, the conversion had to be from an intermediate metabolite and not directly from glucose. The present inventors argued that plant biomass could be readily degraded to this intermediate and then converted to ethanol. The intermediate was most likely lactic acid. Thermodynamic calculations indicate that it is thermodynamically feasible to convert lactic acid to ethanol under high $H_2$ and low $CO_2$. Lactic acid was not measured, but pH increased between 24 and 48 hours. Lactic acid has a low pKa and a greater effect on pH at the low pH values of that experiment. *Streptococcus bovis*, a rumen starch degrader, can produce both ethanol and lactic acid, and is ideal to orchestrate this conversion.

IV. Additional Improvements

The present inventors have also discovered other aspects of the digestion process which are disclosed herein. In mixed culture or in pure cultures, care should be taken to maintain anaerobic conditions. Even small amounts of oxygen that perfuse through tubing will decrease the portion of biomass converted to ethanol. In mixed culture, allowing air into the media for 20 minutes before the start of the digestion resulted in ethanol being degraded even when perfusing with $H_2$ during fermentation, while perfusing media with $H_2$ for 20 minutes increased ethanol production, each compared to perfusing with oxygen-free $N_2$ for 20 min. In all cases, the flasks were perfused with 1 atm $H_2$ during digestion, but the perfusion before digestion was still affected by residual oxygen. When $N_2$ or $CO_2$ are perfused into the cultures, they should be deoxygenated by passing them through a copper column before perfusing them through the
culture. Resazurin or other indicator of redox potential should be used to insure that the media is free of oxygen. Use of reducing agents such as $Na_2S$ and cysteine is also disclosed herein as preventing oxidation of cultures, for single cultures but a mixed culture was found not improved by using $Na_2S$ compared to a control.

Generally, headspace gases are used at pressures of about 0.02 to 2 atmospheres of pressure.

Preferred Process for Ethanol Production from Plant Biomass

The process described below incorporates information and results obtained as disclosed in U.S. Ser. No. 12/000,856, and the present application for production of ethanol from plant biomass once the microbial culture is obtained. This description does not include redundant details of the process for using the present invention that have already been described in both U.S. Ser. No. 12/000,856, which is incorporated by reference, and elsewhere in the present specification.

Type of Feedstock

The microorganisms in the rumen can digest most plant cell components including sugar, protein, starch, cellulose, hemicellulose and pectin. Decreasing the rate of passage of solid material in an artificial system allows for greater digestion than occurs in the cow. For example, solids remain in the rumen for an average of about 24 h (turnover time) for a high-producing dairy cow, and about 50-60% of grass hay fiber is digested in that period of time. When we incubate grass hay with rumen microbes for 4 days, about 80% of the organic matter is digested. Thus, a longer incubation time than observed in cattle is more advantageous for fuel production. We can readily test feedstock in vitro to determine its rate of digestion, and determine the preferred retention time based on this rate and value of energy to be captured.

The rumen microbial digestion system will not readily digest lignin and some macromolecules bound to lignin. If feedstock containing protein and carbohydrate is heated above 60° C. during storage, some protein and carbohydrate becomes bound together and becomes less digestible. Some plants contain tannins that may inhibit digestion. Other than these limited exceptions, the microbial population can digest most sources of biomass without pretreatment, and with pretreatments these exceptions may be digested as well.

The present invention may use any biomass source, but certain sources are particularly advantageous. This microbial population quickly degrades any source of cellulosic biomass that can be fed to cattle (grass, wheat straw, corn stover). In addition, some sources that would not be fed to cattle can also be used. Less digestible grasses (e.g. mature switch grass) can be digested over longer periods of time than the ruminant's gut allows. Biomass sources that the animal will not eat (e.g. paper), and sources that cannot be fed to animals because of toxins may also be used. Moreover, since wet feedstock may also be used (<1% dry mass), algae, manure or sewage is also excellent feedstock. Algae have very low lignin and would be nearly completely digested in less than one day, i.e., less than 24 hours. Wood byproducts may be used after de-lignification thereof. Because the approach provided by the present invention is cost effective even at a small scale, transportation and drying costs can be greatly decreased, and biomass sources in isolated areas may be used.

Examples of feedstock that can be digested directly with minimal processing include but are not limited to: cool season (C3) grasses (e.g. timothy, orchard grass), legumes (e.g. alfalfa, lucaena), warm season (C4) grasses (e.g. corn, switchgrass, burmudagrass, miscanthus, sugar cane), crop residues (e.g. soybean plants, corn stover, wheat straw, cane bagasse), cover crops (e.g. small grain crops like oats or vetch to protect soils) algae or seaweed, tree leaves, food waste (e.g. cafeteria waste, processing wastes like potatoes), paper or cardboard, paper byproducts, animal or human manures. In addition, protein byproducts can also be readily digested and converted to ethanol or used as a co-substrate. These include animal mortality (e.g. carcasses), as well as the protein in the previously mentioned sources. Microorganisms themselves may be used as feedstock. With greater preprocessing, such as treatment with acids or bases or enzymes, materials with more lignin can be more readily degraded such as wood byproducts, and tree crops (e.g. pine, poplar).

Various methods of preprocessing may increase the rate of digestion, and therefore the amount of material that can be processed, or the type of material that can be used efficiently. Any preprocessing method used for enzymatic digestion of biomass such as for other biochemical methods of cellulosic ethanol production can be used. In addition, any method of treating biomass to increase digestibility of animal feeds, particularly cattle feeds, would also increase the digestibility for this process. These methods include: boiling in acid or base, treatment with peroxide, pretreatment with enzymes, steam treatment, grinding, milling, tearing or shredding, among others. Materials can be stored prior to use by ensiling or drying to hay, or partially drying. Appropriate storage may prevent decreases in digestibility and respiration losses.

The advantages of one feedstock over another include: where it can be grown in an environmentally sound manner considering soils, climate and other factors (e.g. cool season grasses vs. sugar cane); yield per acre (e.g miscanthus or switchgrass have high yields per acre); consistency of production; ease and cost of production (e.g. perennial grasses do not need to be replanted); how quickly it can be digested (e.g. many feedstock have been studied for cattle diets and factors like plant species, maturity, and type that affect rate of digestion apply here); how much pretreatment it requires; how much residue is left; ability to use residues of digestion; ability to use other co-products of feedstock production or digestion; and the need to handle, process, decontaminate, or reduce a waste stream (e.g. sewage).

Selection of Microorganisms

The first step in digestion and fermentation to ethanol is selection of the microbial culture. It is acceptable to use either an undefined mixed culture such as rumen fluid taken directly from a cow, or a pure culture of one or more microorganisms. Pure cultures also may be more advantageous as they use organisms that have been isolated and developed and convert most of the biomass to ethanol without the need to manipulate conditions to inhibit production of acids or other products.

Some of the factors which are considered in determining whether to use single cultures or mixed cultures are as follows. Individual microorganisms have different characteristics enabling them to perform better in different situations. One option is to make a mixed culture of several useful organisms. Generally, mixed cultures digest biomass faster than pure cultures. As long as methanogens or acetate degraders are kept out of the fermentation, much of the biomass can be converted to ethanol. The mixed cultures may also contain specialist microorganism that digest cellulose, hemicellulose, pectin, and/or starch. They may differ in pH optimum and temperature optimum. Some microorganisms produce ethanol under high ethanol concentration and others under low ethanol concentration. As the fermentation proceeds, pH may decrease, temperature might increase, and the form of substrate may vary. The microbial population will adjust with specialists succeeding and reproducing when they are most needed.

V. Laboratory Scale Digestion and Fermentation

In order to provide a preferred system to digest and ferment biomass to ethanol, preferred microorganisms must be matched to the preferred industrial-scale process. Determining the most advantageous conditions for this process requires an understanding of the most preferred conditions of the microorganisms that are available for use, and an understanding of how the organisms interact with the feedstock and process conditions. Microorganisms may be evaluated in mono-culture first to determine where they fit into the digestion and fermentation scheme, but ultimately, the final mix of microorganisms to be used must be evaluated.

Further, the mix of microorganisms to be used must be evaluated on the feedstock that will be used. Several mixes can be compared, and several other factors can be used simultaneously. The feedstock must be digested to ethanol in vitro to determine the preferred conditions. Specifically, the required nutrients and factors for the desired outcome must be determined at laboratory scale. Many microorganisms were isolated with several growth factors included so the factors that are actually needed for preferred results may be determined by routine experimentation, and determining this information will decrease the cost of the digestion at the larger scale. The conditions needed for preferred biomass conversion to ethanol are determined by bench-scale fermentation using conditions similar to the enrichment or isolation. These conditions include gas head space treatment, temperature, buffering, ethanol concentration, and VFA concentration, for example. The rate of cell growth and rate of digestion is determined before planning the large-scale digester. The advantages and disadvantages of batch culture or continuous culture for a particular product are assessed in vitro. Most feedstock must be ground for in vitro studies to insure uniform sampling, but an experiment may be needed to determine the optimal grinding size. Each of these variables is determined by altering them one at a time or several at a time, after making observations based on evaluation on other feedstock, thermodynamics, and similar microbial species. One hundred or more samples may be compared in a single run with runs replicated a few times to verify accuracy and reproducibility of the observed results.

VI. Industrial Scale Digestion and Fermentation

One or more of the isolated microorganisms or mixed cultures taken from an anaerobic environment can be used in a consolidated bioprocessing method as described below. In this process, certain conditions are maintained to result in preferred ethanol or other lower alkyl alcohol production.

1. Optional pretreatment of biomass to remove oxygen and kill microorganisms from the feedstock or environment.
2. Slowly adding the biomass to the digester-fermenter to increase the portion of biomass converted to the desired product (e.g. ethanol) vs. other potential products.
3. Maintaining an appropriate partial pressure of hydrogen gas or other hydrogenase inhibitor to shift fermentation toward ethanol from acetic acid, if necessary.
4. Removing digested biomass but leaving or returning microorganisms
5. Removing ethanol and other products from the digester-fermenter
6. Separating or further treating removed liquids and solids.
7. Maintaining low partial pressures of $CO_2$ to shift fermentation toward ethanol or butanol production.

A more detailed description of industrial scale digestion may be made with reference to FIG. 2.

The biomass is ground or chopped to accelerate digestion. FIG. 2 depicts a storage module or component prior to chopping. The preferred extent of grinding will depend on the type of biomass and its handling. However, in the laboratory biomass is ground through a 1-mm screen of a Wiley mill. This is done to make the substrate more uniform, but indeed microorganisms like those in the rumen can break down the particle size of many feeds on their own. Some have argued that the rapid rate of rumen digestion compared to biofuel digesters is due to the mastication of the feed. However, the present inventors have demonstrated that rumen microbes are capable of degrading the particle size of feeds like timothy (grass) hay or alfalfa without mechanical methods, and thus one aspect of the present invention resides in the discovery that degradation of particle size for many natural feeds can be effected without mechanical particle size reduction.

The biomass then undergoes a mild pretreatment to sterilize the biomass and remove oxygen. This is depicted in FIG. 2 as "Pretreatment." The process conditions for pretreatment are both anaerobic and aseptic. Water is added to the biomass if necessary to facilitate uniform heating and fermentation. In a pretreatment reactor, water or recycled fluid from the fermenter is added to enable even heating of the biomass. The slurry is heated to kill microorganisms in the biomass, and oxygen would be removed by displacing air with oxygen-free nitrogen gas by purge, for example. Additional sterile oxygen-free water or recycled fluid from the fermenter is added to obtain about 5-20% by weight, preferably about 10% by weight, organic matter final concentration in the fermenter. Organic matter concentration in the pretreatment vessel depends on the organic matter concentration removed from the fermenter. Alternatively, non-sterile liquid may be added before heating and deoxygenating. If undefined cultures are used, the sterilization is completely unnecessary.

The slurry is cooled to a preferred temperature for fermentation. This temperature, of course, depends on the preferred conditions for the microorganisms being used for digestion. For many isolates currently available, this temperature is about 30° C. to 45° C., preferably about 40° C., but some isolates were isolated at higher temperatures, i.e., from about 50° C. to 60° C., preferably about 55° C. Once inoculated, the conditions of the fermenter (or digester) are maintained strictly anaerobic unless some microorganisms turn out to be facultative anaerobes. The slurry is continuously added to the top of the fermenter. The rate of entry of the biomass is important to control the profile of products produced. Slower continuous entry of biomass decreases carbohydrate or intermediates (e.g. cellobiose, glucose, pyruvate) available to microorganisms and makes certain metabolic pathways infeasible. For example, if high concentrations of carbohydrate are available, under conditions of high hydrogen pressure, both acetic acid and ethanol production are feasible. Microorganisms will preferentially make acetic acid because it yields more ATP for microbial growth. However, if the carbohydrate intermediate is limited, acetic acid production becomes thermodynamically unfeasible at the same hydrogen pressure, and ethanol predominates.

The fermenter is maintained at the optimal temperature for the population of microorganisms to produce ethanol, i.e., about 40° C. to 55° C. The fermenter headspace is maintained with an adequate partial pressure of hydrogen gas to shift fermentation toward ethanol production. For different microorganisms this concentration ranges from about 0.02 atmospheres to 2.0 atmospheres. The source of the hydrogen may be the fermentation by the microorganisms themselves with co-production of acetic acid, or hydrogen may be added to prevent acetic acid production. Some level of carbon dioxide may be allowed depending on the microbial strains. Hydrogen or any other additive to inhibit hydrogenases would not be needed
at all with microorganisms that do not have hydrogenases or the ability of make other products. Actual conditions will be determined from in vitro experiments and thermodynamic analysis. Different strains of microorganisms may be included as the concentration of ethanol increases.

Maintaining microorganisms in the fermenter while removing waste and products is desirable. If carbon dioxide presence is not incompatible with ethanol production for the microbial organisms used, carbon dioxide in the headspace will be allowed. For many isolated organisms, some amount of carbon dioxide is tolerable, but removing $CO_2$ shifts metabolism toward greater ethanol production when it is thermodynamically limited. When carbon dioxide is in the headspace, the actively digesting biomass floats. The digested biomass sinks to the bottom of the fermenter. Therefore, digested biomass can be removed from the bottom of the fermenter continuously if needed to increase space for added biomass. Most active microbes are
attached to the floating biomass; therefore they are not removed from the bottom of the vessel. If the biomass is nearly completely digestible, it will not need to be removed. Liquids can be removed from the bottom of the fermenter and may be screened or filtered to leave undigested biomass and attached microbes. Another way to maintain microorganisms in the digester is to distill ethanol using vacuum pressure distillation, gas stripping, or membranes during the fermentation. Microbes can be separated from removed liquids with centrifugation or filtering and returned to the digester-fermenter.

Some byproducts will be produced, especially VFA. Using a mixed culture of microorganisms, these byproducts can be converted to other products or fuels or removed for a subsequent process. These products might be catalyzed to ethanol, other alcohols, alkanes (methane, ethane, propane, butane) using a chemical process. Other aspects of this invention can be used to readily degrade the byproducts to $H_2$ and $CO_2$ or $CH_4$.

Other co-products include undigested feedstock, which can serve as a soil amendment because it largely represents biomass which would degrade slowly in soil, and therefore remain for a long time, and it contains nutrients like nitrogen and phosphorus needed by plants. This undigested residue may be used directly, dried or pelleted. It can also be used as a carbon sequestration product and stored where it will not readily degrade such as under anaerobic conditions. Potential carbon or nitrogen trading credits might also be a co-product of the fermentation because the process decreases the release of greenhouse gases compared to use of fossil fuel and it could use crops which sequester nutrients or otherwise have a beneficial environmental effect. Microbial protein produced in the process may be used in animal feeds or as a soil amendment.

One unique aspect of this approach is the organisms produce high concentrations of ethanol, such as greater than 5%, and preferably greater than 8% or 10%. However, the digestion never needs to be exposed to 5% or 8% monosaccharide. The monosaccharide is used as it is produced. One reason many previous attempts to develop a process like this have failed is the investigators were seeking a microorganism like yeast that could tolerate high sugar concentrations. While such organisms are possible, they are not necessary.

Alternative Processes

Using all the described steps above would accelerate digestion, shift fermentation toward desired products, and maintain high concentrations of activity even in solutions with high ethanol concentrations. However many of the steps are optional for adequate production of ethanol. It may be more cost effective not to use some of the steps. There are many variations on the process for producing alcohols and which variation is optimal depends on matching the process to the feedstock, microbial culture and other conditions.

The previous process described a continuous culture digester-fermenter to produce ethanol. Relatively high concentrations were also obtained in batch culture, or continuous batch cultures in which feedstock is added intermittently. With improvement of the microorganisms, a batch culture may be more advantageous.

Alternatively, a process using a non-aseptic mixed culture of microorganisms taken from an anaerobic environment can be used. In this case, the presence of other metabolic pathways makes the control by adding microbial inhibitors or controlling removal or addition of metabolites more important. For example, if an individual organism produces acetic acid or
ethanol, the most important control mechanisms are to maintain high levels of microbial activity (low dilution rate), high hydrogen concentrations, and low concentrations of substrate (gradual feeding). These conditions decrease the reactants (e.g. glucose or cellobiose), and increase the products for acetic acid fermentation (e.g. $H_2$). As the acetic acid concentration builds up, it becomes infeasible to generate ATP by acetate kinase step, and NADH builds up, only to be released by ethanol production. If an organism or mixture of microorganisms also can convert glucose to 3-carbon sugars, propionic acid or lactic acid, an additional condition of the fermentation would be to decrease the $CO_2$ concentration. With low $CO_2$ concentration, the 2-carbon acetic acid and ethanol become favored.

Provisional patent application Ser. No. 60/871,441, and U.S. Ser. No. 12/000,856, describe an alternative process for production of lower alkyl alcohols, compared with direct fermentation to the alcohols. Organic acids can be produced using various cultures of microorganisms, and these acids converted subsequently to alcohols. In some cases, the alcohols can be converted by microorganisms or a chemical process can be employed. It is well known that many different microorganisms produce various organic acids which can serve as intermediates: lactic acid, acetic acid, propionic acid, butyric acid, and longer chain acids. If a certain organic acid is desired for a certain end product, the changes in gas composition, use of inhibitors such as methane inhibitors, changes in gas pressures, addition or retention of certain gases such as hydrogen, are all ways to manipulate the rate of digestion to VFA and the rate of VFA production. Further, specific VFA can be obtained using pure cultures of microorganisms that only produce the desired VFA or a limited number of products, which can be further controlled by controlling the concentrations of gases and solutes.

Reductive acetogens are known to make acetate from carbon dioxide and hydrogen, and adding hydrogen can increase the length of the VFA as described in U.S. Ser. No. 12/000,856. If carbon efficiency is desired, a combination of organisms that degrade biomass and organisms that synthesize acetate from $CO_2$ and $H_2$ or CO and $H_2$ (syngas) can be used. These can be isolated organisms. Where acetate degradation is desired, or shortening of the length of VFA, low pressures, particularly low $CO_2$ or $H_2$ pressures can be applied. Conversely, where greater incorporation of $CO_2$ or $H_2$, greater acetate production from $CO_2$ and $H_2$, greater assimilation of ethanol from $CO_2$ and $H_2$, or longer chain VFA are desired, the partial pressure of $CO_2$ and $H_2$ can be increased simply by increasing the total gas pressure. In general, a way to use low concentrations of $H_2$ in a mix of gases is to incubate the gases containing $H_2$ and $CO_2$ with methanogens or acetogens that use even very low concentrations of $H_2$ to make methane or acetate. The methane or acetate can be used or separated more easily than the low concentrations of $H_2$ or $CO_2$. The acetate can be used for production of ethanol. Alternatively, the low concentrations of $H_2$ or $CO_2$ can be recovered by increasing the length of VFA produced, thus storing more energy as VFA for subsequent conversion to a different product, or recovered and used as is.

Specifically, we describe a process for making alcohol which includes prospecting and isolating microorganisms that are incubated under certain conditions that make digestion of feedstock more stable, faster, take fermentation farther (to higher concentrations), or produce more of the product desired. The present inventors isolated over 200 such isolates which can be compared for their favorable traits. The rumen microorganisms, having evolved to directly digest many forms of feedstock without pretreatments in acids or high temperatures, can digest many forms of feedstock readily without pretreatment. For example, grasses, leaves, grains, paper, cardboard, and many waste products have been shown to be readily degraded to organic acids, and could be degraded directly to alcohols under the conditions demonstrated, or to organic acids which can be converted to alcohols. Thus, an advantage of the invention is that many feedstocks would require no pre-processing. These organisms could be adapted to other forms of biomass and could have a special advantage for wet biomass (e.g. algae, manure).

Additionally, the organic acids or the alcohols can be produced from waste gases as well as waste organic matter. The application described producing acetic acid from $CO_2$ and $H_2$ and the subsequent elongation of VFA by these gases. Alternatively, CO and $H_2$ (syngas) could be used. Again, adding higher partial pressures of these gases will increase their use for VFA production. Increasing total pressure is one simple way of increasing partial pressures. By maintaining gases produced by the digestion of biomass and fermentation, especially under greater than 1 atm of pressure, these gases can be converted to VFA and all of the carbon in the biomass that is released in digestion could be used to produce the desired acids, instead of methane or $CO_2$ when it is not needed. Acids produced in this way can be converted to alcohols. For example, acetic acid produced from both degradation of feed and synthesis by reductive acetogens can be converted chemically to ethanol or butanol. The organisms to carry out these synthesis reactions were shown to occur in the rumen, and could be readily isolated using the pressures or other conditions that allow their growth.

VII. Production of Lower Alkyl Alcohols Other than Ethanol

As noted above, the present invention also specifically contemplates the production of lower alkyl alcohols other than ethanol, including propanol and butanol.

In order to produce propanol or butanol the same procedures would be used to screen and isolate microorganisms of interest in producing propanol or butanol, and either propanol or ethanol would be used in the enrichment phase depending on the desired product, i.e., using propanol or butanol in the enrichment phase to favor the production of each alcohol, respectively.

Thus, different microorganisms are selected for production of propanol or butanol.

For example, see U.S. Pat. No. 4,443,542, which describes the use of naturally-occurring *Clostridium* sp. to produce butanol. This patent is incorporated herein in the entirety by reference. *Clostridium* sp. may be used in accordance with the methodologies disclosed herein.

Thus, $H_2$ must be supplied either as headspace or also sparge in addition thereto, to produce propanol, but hydrogenase could be inhibited to produce ethanol or butanol. The particular considerations also provided by the present invention are for digestion, for example: 1) for ethanol or butanol, removal of $CO_2$ (vacuum, perfusion gases), 2) adding the feedstock over time rather than all at once, 3) using the feedstock without pretreatment (no acid predigestion, minimal grinding).

The advantages of the present invention are that celluolosic biomass may be used to produce butanol directly rather than using more expensive substrates like free glucose, and microorganisms isolated so far tolerate as much as 6% butanol. Thus, relatively high concentrations of butanol can be produced directly from biomass, including cellulosic biomass, when controlling partial pressures of gases and other metabolite concentrations.

Furthermore, butanol or propanol, in addition to ethanol, can be produced from synthesis gases like $CO_2$, CO and $H_2$. For example, a microorganism tolerant to as much as 6% butanol, as isolated, could be used to assimilate acetic acid derived from $CO_2$ and $H_2$, into butanol. This high concentration of butanol obtained from synthesis gases would be possible by optimizing the profile of gases, pressurizing the system, and/or selecting from microbes with the desired pathways, and no undesired pathways using these conditions. With optimal gas concentrations, such reactions are thermodynamically feasible, and organisms such as those in the rumen are readily able to synthesize acetic acid, and convert acetic acid to butyric acid or butanol.

Alternative Products

In addition to alcohols and alkanes, alternative products can include the organic acids themselves, or products that can be made from the organic acids such as polymers (e.g. polyvinyl acetate). All of the means to shift fermentation by adjusting end products or use of inhibitors can help in the production and control of production of such alternative products. The organic acids can serve as intermediates for production of alkanes as well as alcohols.

Control of Other Fermentations

Conditions for incubating pure cultures of microorganisms to produce ethanol have been established. Further, conditions for incubating undefined mixed cultures of anaerobic microorganisms to shift the fermentation products toward ethanol are also calculated, and were shown to cause predicted shifts toward ethanol or butanol from other volatile fatty acids. When high concentrations of hydrogen were used in mixed culture, volatile fatty acids were degraded to methane and carbon dioxide. Thermodynamic calculations showed that this shift could occur because methanogens decreased the $CO_2$ concentration so much that degradation of VFA to $CO_2$ and $CH_4$ or $H_2$ becomes thermodynamically favored. Under such conditions, ethanol degradation is also favored. However, incubating with lower concentrations of $H_2$, such as a mix of 80% $CH_4$ and 20% $H_2$ increased ethanol and butanol concentrations substantially. There are two applications from this thermodynamic and empirical observation. One application is a means to produce ethanol using a moderately high (not too high) concentration of $H_2$ to shift a mixed undefined culture fermentation toward ethanol when acetate degradation i.s an alternative available pathway. A second application is the means to increase VFA degradation rate to biogas ($CH_4$, $H_2$ and $CO_2$). A third application is the alternative approach to produce ethanol using microorganisms, by excluding organisms that degrade VFA (e.g. by using cultures that don't contain them) or inhibiting VFA degradation with reagents or conditions.

In accordance with the present invention; any conventional digester or fermenter may be used with adjustments required to meet the above-described thermodynamically favorable conditions, such as provision for $H_2$ or removal of $CO_2$ from the headspace, for example, in accordance with the present invention.

For example, digesters as disclosed in each of U.S. Pat. Nos. 6,299,774; 6,342,378; 5,525,229; and 6,673,243, may be used with any desired adjustments in accordance with the present invention. Each and all of the U.S. patents are incorporated herein by reference in the entirety.

The digesters may be used, as noted herein, to digest purely cellulosic biomass or may also be used to digest animal manure which may contain some cellulosic biomass. Further, the digesters may be used in large scale to furnish large volumes of lower alkyl alcohols, such as ethanol, propanol or butanol, or they may be used in small scale on individual farms where manure digestion is used for both manure management in addition to ethanol production.

One specific type of digester that may be mentioned is an induced blanket reactor (IBR) digester. See U.S. Pat. No. 6,911,149, which is incorporated herein in the entirety.

Further Utilizations of the Second Law of Thermodynamics

The present specification clearly demonstrates the application of the second law of thermodynamics to the control and/or manipulation of complex chemical systems, including living systems in general, and a microbial ecosystem, in particular. The second law is, thus, applied to predict and control fermentation or digestion based on existing enzyme activity at a point in time, and to control the evolution of new microbial activity going forward in time.

The same approach may be applied to similar microbial ecosystems to effect a shift toward production of desired products, which may be minor metabolites under typical fermentation conditions. For example, production of longer chain fatty acids, alcohols, or alkanes may be promoted by shifting equilibrium in their favor. Other products might be selected such as ketones or aldehydes. Thus, the present invention broadly provides an application of the second law of thermodynamics using a solution of simultaneous equations, to establish conditions to control fermentation, direct the evolution of species in single cultures or mixed cultures, and to select for microorganisms that can be used in subsequent fermentations.

Directed Enhancement of Microorganisms

The present invention generally provides a method of directing enhancement of microorganisms to produce a product by fermentative digestion of cellulosic biomass, which entails the step of digesting cellulosic biomass with a first set of microorganisms, and enriching the digesting with an amount of the product to thereby favor growth of a second set of microorganisms that produce a greater yield of the product, and which are more tolerant to the product than the first set of microorganisms. Alternatively, or in addition, concentrations of other metabolites or gas pressures can be maintained to thermodynamically favor microorganisms that use a certain substrate or produce a desired product. Using these artificial, i.e., unnatural, conditions, unique microorganisms can be selected or developed in accordance with the present invention.

Generally, the first set of microorganisms may be isolated in culture before use, or may be used "as is" from a naturally-occurring source, such as soil or animal manure. During enrichment in the presence of an amount of the desired product that exceeds that found in nature, the digestion will, by selection and, perhaps, by mutation, favor the development of a second set of microorganisms that are particularly suited for conditions existing in and around, i.e., including headspace, the digesting medium. By allowing this cycle to continue sequentially, it is possible to encourage the growth of microorganisms that exceed the abilities or capacities of previous generations of microorganisms in producing the desired product. As used herein, the "first set of microorganism" is the starter set of microorganisms with which digestion commences. By "second set of microorganisms" is meant a subsequent or Nth generation or progeny of the first set of microorganisms. The second set of microorganisms is generally at least 10 and preferably at least $10^3$ generations or more after the first set.

For example, if it is desired to produce an $N^{th}$ generation, where N may be an integer from generally 10 to at least $10^3$ and preferably at least $10^4$ generations. However, N may be an integral value in excess of $10^5$.

VIII. Exemplary Microorganisms, Including Aerobic Microorganisms

Some of the microbial isolates were found to be strict anaerobes, and others grew readily in the open air. Strict anaerobic microorganisms do not grow in the presence of $O_2$. Facultative anaerobes have enzymes such as catylase and superoxide dismutase for disposing of $O_2$ metabolites, and therefore these microorganisms tolerate but do not use $O_2$. Aerobic microorganisms have complex enzyme systems for passing electrons from one intermediate to another while capturing energy and eventually reducing $O_2$ to $H_2O$. Each of these different types of organisms may be distantly related. The inventors discovered some strict anaerobic microorganisms (e.g. *Ruminococcus albus*) and some $O_2$-tolerant or aerobic microorganisms (e.g. #115) that convert a high percentage of biomass to ethanol under 6% or greater ethanol concentration by volume. Thus, the methods of isolating the desired activity to enable conversion of most cellulosic biomass to ethanol and the methods to apply conditions to concentrate ethanol are generally effective for organisms of many types. The ability to tolerate $O_2$, or to use it, provide specific advantages discussed previously. Oxygen-tolerant organisms may be easier to handle, and $O_2$-using organisms may be grown under controlled conditions separately from fermentation to ethanol. Thus, the present specification specifically contemplates use of aerobic microorganisms for lower alkyl alcohol production.

Furthermore, it is clear that for both aerobic and anaerobic microorganisms' intolerance to lower alky alcohols such as ethanol may be overcome by $CO_2$ removal from the headspace of the digestion. This provided empirical evidence to support the theory that a microorganism's intolerance to lower alkyl alcohols, particularly ethanol, is determined by extraneous chemical equilibrium. That is, often a microorganism's intolerance to alkyl alcohol, such as intolerance to ethanol, is caused by concentrations of reactants and products that disfavor production of lower alkyl alcohols because the microorganism cannot obtain energy for growth by making more alkyl alcohol due to thermodynamic constraints. Removing these constraints by altering concentrations of available reactants and products (e.g. $CO_2$) enables production of alkyl alcohol even while alkyl alcohol concentration remains high for many different types of microorganism, whether anaerobic or aerobic.

Both the analysis of thermodynamics and empirical evidence supports this idea. For example, microbe 213 was enriched and selected under high $H_2$ pressure. These are conditions that select for ethanol producers because making ethanol is one of the few pathways for microorganisms to obtain energy under these conditions. The high $H_2$ pressure shifts equilibrium against acetic acid, and the low $CO_2$ pressure shifts it away from propionic acid, for example. Thermodynamic analysis shows that little energy may be obtained under these conditions from production of either acid from a low concentration of glucose, and thus, available glucose is used to make ethanol, which keeps the concentration of available glucose low.

The microorganism 213, isolated under these conditions exclusively makes ethanol and $CO_2$ even at low ethanol concentration. Many other microorganisms make different products when ethanol concentration is low and shift to ethanol at high ethanol concentration as ethanol concentration inhibits the alternate pathways as discussed. Although this microorganism could readily produce ethanol, it was only tolerant to about 2% ethanol concentration when grown under 1 atm. $CO_2$ gas pressure. It seems that the low tolerance to ethanol might have had something to do with the fact that the microorganism didn't have many options for metabolism other than to make ethanol, which suggests thermodynamics is limiting.

Ethanol tolerance was improved for this organism by slowly increasing the ethanol concentration in fermentations under $CO_2$. Eventually, this microbe could tolerate up to 4% ethanol concentration under 1 atm. $CO_2$ pressure. However, the modified culture no longer exclusively converted cellobiose to ethanol. All of the cellobiose could not be accounted for as ethanol and $CO_2$ when incubated at low ethanol concentration. It appears that the inventors made the organism more ethanol tolerant by selecting out mutants that could make something besides ethanol. Finally, although this mutant was tolerant to no more than 4% ethanol when grown under 1 atm $CO_2$, it was tolerant to more than 6% ethanol under 1 atm $N_2$. Decreasing one co-product, $CO_2$, increased the possibility of producing a second co-product, ethanol, as would be suggested for thermodynamically limiting reactions.

Thus, the empirical evidence supports the theory that thermodynamic analysis can be used to overcome intolerance to alkyl alcohol as well as select or develop microorganisms that make alkyl alcohol, and provide conditions to shift fermentation toward alcohols: 1) Conditions that favored ethanol resulted in selection of an organisms that could only make ethanol, 2) This organism which produced only ethanol was not able to grow when ethanol concentrations exceeded 2% of volume and $CO_2$ was 1 atm. which are conditions thought to be thermodynamically limiting 3) The same organism could be made to grow under similar conditions by developing mutants that did not need to make ethanol. 4) Removing the co-product $CO_2$ increased the tolerance to ethanol. Intolerance to ethanol can be overcome by making ethanol production thermodynamically favorable to further ethanol production.

16S r DNA Sequence for Exemplary Microorganisms and their Identity as Determined by BLAST Searches
Identification of Microbial Species The microbial isolates were each gram stained and characterized as fungi, gram positive or gram negative rods or cocci. Isolates were further identified by other phenotypic characteristics such as aerobicity and carbon sources utilized.

The phylogenetical relationship to other microorganisms was determined by base-pair sequence of the 16S ribosomal DNA. Twenty bacterial isolates were selected for their ability to convert a high percentage of cellobiose to ethanol, or ability to produce ethanol even when ethanol concentrations were greater than 6% by volume. Each isolate was purified and plated on slant agar tubes and sent to an outside contractor. The contractor performed colony PCR using a forward (8FPL; AGTTTGATCCTGGCTCAG (SEQ ID NO: 1)) and reverse (1492RPL; GGYTACCTTGTTACGACTT (SEQ ID NO: 2)) primer and verified fragments using gel electrophoresis. The PCR product was sequenced using an automated sequencer with the same primers.

Contiguous 16S rDNA sequences obtained with forward or reverse primers were edited using Chromas Lite 2.01 (Technelysium Pty Ltd) and assembled using CAP3 program (Huang and Madan, 1999). See Huang, X. and A. Madan. 1999. CAP3: A DNA sequence assembly program, Genome Res. 9: 868-877. CAP3 was operated on and the resulting assembled fragments are indicated below. After the two sequences for each organism were assembled, the sequence was compared to the NCBI database against all nucleic acid deposits accepting 97% or greater homology with identified bacterial 16S rDNA as potentially the same species. When more than one species was identified as similar to the isolates, each species is listed in Table 5. Some of these alternative species may have been misidentified in the database, they may have been incorrectly classified as separate species, but most likely they are close relatives that could not be differentiated based on 16S rDNA. Four isolates did not produce PCR product and were not sequenced.

The 20 isolates that were sent out for identification were selected because they produced a greater amount of ethanol from cellobiose than the average of all isolates. Results of the identification using rDNA sequences were confirmed by separately obtained results based on phenotype. The results in Table 5 show substantial diversity of bacterial species that can produce ethanol from cellulosic biomass, and also recall that fungi that converted cellobiose to ethanol were also isolated. Thus, microorganisms isolated by the described procedures represented two kingdoms (fungi and bacteria). Within the bacterial kingdom, isolates represented two classes (bacilli and clostridia), three orders (Lactobacillales, Bacillales, Clostridales), four families (Lactobacillaceae, Staphylococcaceae, Enterococcaceae, Clostridiaceae), and five genera (*Lactobacillus, Staphylococcus, Enterococcus, Clostridium, Pediococcus*). These isolates represent strict anaerobes, facultative anaerobes, and aerobic microorganisms capable of respiration. It is likely that several other species of microorganism could also be isolated and made to convert cellulosic feedstock to ethanol. Thus, the inventors have demonstrated and disclosed the use of any of the bacterial species named in Table 5 for ethanol production, as well as many other species that will be isolated by similar means as described in this application.

Some functional characteristics can be attributed to certain isolates, which can now be traced to a certain genus and species. For example, *Staphylococcus epidermidis* is known to grow by aerobic respiration as well as fermentation. Thus, it is possible to use aerobic conditions to grow the desired organism while ethanol would be produced under anaerobic conditions. *Enterococcus, Lactobacillus* or *Pediococcus* are known to tolerate oxygen so their use may be facile compared to strict anaerobes like *Clostridium*.

An organism (#247) with rDNA which was 99% homologus with *Pediococcus acidilactici* was cultured from 5% butanol, and was tolerant to 10% ethanol. Organism #115 converted about 50% cellobiose to ethanol when ethanol exceeded 6 to 7% of media by volume; it was tolerant to sulfite and oxygen, and was identified as a member of the genus *Enterococcus*, with 99% homology of the 16S rDNA to one of the close relatives of *E. mundtii, E. hirae, E. faecium*, or *E. durans*. Another organism (#149) converted about 50% by weight of cellobiose to ethanol, and repeatedly did so when additional cellobiose was added after several days of incubation. This organism was identified as having rDNA with greater than 99% homology with *Clostridium bifermentans* or *C. sordellii*. This organism also produced ethanol when ethanol concentration exceeded 7% by volume. Organism 213 converted about two thirds of cellobiose or AVICEL® (microcrystalline cellulose) carbon to ethanol irrespective of the gas composition. If $CO_2$ comprised the gas phase, microbial growth was inhibited when ethanol concentration exceeded 2%, but tolerance to ethanol exceeded 6% when $CO_2$ was removed. This organism was identified as a member of the genus *Enterococcus* and had rDNA homology greater than 99% with cultures of *Enterococcus lactis* and *E. faecium*.

Most microorganisms identified in Table 5 (e.g. 52, 115, 116, 157, 237, 189, 197, 223, 232, and 241) increased ethanol production above 6% by volume when initially screened, and again when tested a second time with 6 replicates each using cellobiose (these second results were all statistically significant at $P<0.05$). Thus, the ability to convert cellulosic biomass to ethanol was prevalent among several species of microorganism. These various isolates represent all genus and species identified.

Of the isolates that were largely selected for ethanol production from cellulose as described, ten were found that also produced butanols and one (#5) also produced propanols. Most isolates have not been tested for alcohols other than ethanol at this time. Of the 10 that produced butanols, three of them were identified by 16S rDNA sequencing (149, 189, 213). These represented members of the genera *Clostridium* and *Enterococcus* and had greater than 99% homology with *C. bifermentans, C. sordellii*, and *E. lactis* or *E. faecium*. An isolate from an enrichment in which butanol production was intentionally selected for was identified as a member of the genus *Pediococcus* and had greater than 99% 16S rDNA homology with *P. acidilactici* and greater than 98% 16S rDNA homology with *P. pentosaceus*.

The sequences determined all provided below with BLAST search results, i.e., Lineage Report, summarized for each sequence immediately thereunder. The sequences as shown and numbered below, e.g. KK149, correspond to the same numbers in Table 5, which presents a summary of the results obtained for BLAST search results with concordance between sequence numbers and the bacterial species with which each is most closely identified. Note that (>97%). is commonly used as a benchmark of species identity for bacteria.

```
KK149 (1389 bp)
                                                        (SEQ ID NO: 3)
CTACCATGCAGTCGAGCGATCTCTTCGGAGAGAGCGGCGGACGGGTGAGTAACGCGTGGG

TAACCTGCCCTGTACACACGGATAACATACCGAAAGGTATACTAATACGGGATAACATAT

GAAAGTCGCATGGCTTTTGTATCAAAGCTCCGGCGGTACAGGATGGACCCGCGTCTGATT

AGCTAGTTGGTAAGGTAATGGCTTACCAAGGCAACGATCAGTAGCCGACCTGAGAGGGTG

ATCGGCCACACTGGAACTGAGACACGGTCCAGACTCCTACGGGAGGCAGCAGTGGGGAAT

ATTGCACAATGGGCGAAAGCCTGATGCAGCAACGCCGCGTGAGCGATGAAGGCCTTCGGG

TCGTAAAGCTCTGTCCTCAAGGAAGATAATGACGGTACTTGAGGAGGAAGCCCCGGCTAA

CTACGTGCCAGCAGCCGCGGTAATACGTAGGGGGCTAGCGTTATTCCGGAATTACTGGGC

GTAAAGGGTGCGTAGGTGGTTTTTTAAGTCAGAAGTGAAAGGCTACGGCTCAACCGTAG

TAAGCTTTTGAAACTAGAGAACTTGAGTGCAGGAGAGGAGAGTAGAATTCCTAGTGTAGC

GGTGAAATGCGTAGATATTAGGAGGAATACCAGTAGCGAAGGCGGCTCTCTGGACTGTAA

CTGACACTGAGGCACGAAAGCGTGGGGAGCAAACAGGATTAGATACCCTGGTAGTCCACG

CCGTAAACGATGAGTACTAGGTGTCGGGGGTTACCCCCCTCGGTGCCGCAGCTAACGCAT

TAAGTACTCCGCCTGGGAAGTACGCTCGCAAGAGTGAAACTCAAAGGAATTGACGGGGAC

CCGCACAAGTAGCGGAGCCATGTGGTTTAATTCGAAAGCAACGCGAAGAACCTTACCTAA
```

-continued

GCTTGACATCCCACTGACCTCTCCCCTAATCGGAGATTTCCCTTCGGGGACAGTGGTGAC

AGGTGGTGCATGGTTGTCGTCAAGCTCGTGTCCTGAGATGTTGGGTTAAGTCCCGCAACG

AGCGCAACCCTTGCCTTTAGTTGCCAGCATTAAGTTGGGCACTCTAGAGGGACTGCCGAG

GATAACTCGGAGGAAGGTGGGGATGACGTCAAATCATCATGCCCCTTATGCTTAGGGCTA

CACACGTGCTACAATGGGTGGTACAGAGGGTTGCCAAGCCGCGAGGTGGAGCTAATCCCT

TAAAGCCATTCTCAGTTCGGATTGTAGGCTGAAACTCGCCTACATGAAGCTGGAGTTACT

AGTAATCGCAGATCAGAATGCTGCGGTGAATGCGTTCCCGGGTCTTGTACACACCGCCCG

TCACACCATGGAAGTTGGGGGCGCCCGAAGCCGGTTAGCTAACCTTTAGGAAGCGGCCTC

GAAGGAACC

KK 157 (1376 bp)
                                                         (SEQ ID NO: 4)
TGCAGTCGAGCGATCTCTTCGGAGAGAGCGGCGGACGGGTGAGTAACGCGTGGGTAACCTGCCCTGTACA

CACGGATAACATACCGAAAGGTATACTAATACGGGATAACATACGAAAGTCGCATGGCTTTTGTATCAAA

GCTCCGGCGGTACAGGATGGACCCGCGTCTGATTAGCTAGTTGGTAAGGTAATGGCTTACCAAGGCAACG

ATCAGTAGCCGACCTGAGAGGGTGATCGGCCACACTGGAACTGAGACACGGTCCAGACTCCTACGGGAGG

CAGCAGTGGGGAATATTGCACAATGGGCGAAAGCCTGATGCAGCAACGCCGCGTGAGCGATGAAGGCCTT

CGGGTCGTAAAGCTCTGTCCTCAAGGAAGATAATGACGGTACTTGAGGAGGAAGCCCCGCTAACTACGTG

CCAGCAGCCGCGGTAATACGTAGGGGGCTAGCGTTATCCGGAATTACTGGGCGTAAAGGGTGCGTAGGTG

GTTTTTTAAGTCAGAAGTGAAAGGCTACGGCTCAACCGTAGTAAGCTTTTGAAACTAGAGAACTTGAGTG

CAGGAGAGGAGAGTAGAATTCCTAGTGTAGCGGTGAAATGCGTAGATATTAGGAGGAATACCAGTAGCGA

AGGCGGCTCTCTGGACTGTAACTGACACTGAGGCACGAAAGCGTGGGGAGCAAACAGGATTAGATACCCT

GGTAGTCCACGCCGTAAACGATGAGTACTAGGTGTCGGGGGTTACCCCCCTCGGTGCCGCAGCTAACGCA

TTAAGTACTCCGCCTGGGGAAGTACGCTCGCAAGAGTGAAACTCAAAGGAATTGACGGGACCCGCACAA

GTAGCGGAGCATGTGGTTTAATTCGAAGCAACGCGAAGAACCTTACCTAAGCTTGACATCCCACTGACCT

CTCCCTAATCGGAGATTTCCCTTCGGGAACAGTGGTTGACAGGTGGGTGCATGGTTGTCGTCAGCTCGTG

TCGTGAGATGTTGGGTTAAGTCCCGCAACGAGCGCAACCCTTGCCTTTAGTTGCCAGCATTAAGTTGGGC

ACTCTAGAGGGACTGCCGAGGATAACTCGGAGGAAGGTGGGGATGACGTCAAATCATCATGCCCCTTATG

CTTAGGGCTACACACGTGCTACAATGGGTGGTACAGAGGGTTGCCAAGCCGCGAGGTGGAGCTAATCCCT

TAAAGCCATTCTCAGTTCGGATTGTAGGCTGAAACTCGCCTACATGAAGCTGGAGTTACTAGTAATCGCA

GATCAGAATGCTGCGGTGAATGCGTTCCCGGGTCTTGTACACACCGCCCGTCACACCATGGAAGTTGGGG

GCGCCCGAAGCCGGTTAGCTAACCTTTAGGAAGCGGCC-TCGAAGG

KK 188 (1373 bp)
                                                         (SEQ ID NO: 5)
TGCAGTCGAGCGATCTCTTCGGAGAGAGCGGCGGACGGGTGAGTAACGCGTGGGTAACCT

GCCCTGTACACACGGATAACATACCGAAAGGTATACTAATACGGGATAACATACGAAAGT

CGCATGGCTTTTGTATCAAAGCTCCGGCGGTACAGGATGGACCCGCGTCTGATTAGCTAG

TTGGTAAGGTAATGGCTTACCAAGGCAACGATCAGTAGCCGACCTGAGAGGGTGATCGGC

CACACTGGAACTGAGACACGGTCCAGACTCCTACGGGAGGCAGCAGTGGGGAATATTGCA

CAATGGGCGAAAGCCTGATGCAGCAACGCCGCGTGAGCGATGAAGGCCTTCGGGTCGTAA

AGCTCTGTCCTCAAGGAAGATAATGACGGTACTTGAGGAGGAAGCCCCGGCTAACTACGT

GCCAGCAGCCGCGGTAATACGTAGGGGGCTAGCGTTATCCGGAATTACTGGGCGTAAAGG

GTGCGTAGGTGGTTTTTTAAGTCAGAAGTGAAAGGCTACGGCTCAACCGTAGTAAGCTTT

-continued

```
TGAAACTAGAGAACTTGAGTGCAGGAGAGGAGAGTAGAATTCCTAGTGTAGCGGTGAAAT

GCGTAGATATTAGGAGGAATACCAGTAGCGAAGGCGGCTCTCTGGACTGTAACTGACACT

GAGGCACGAAAGCGTGGGGAGCAAACAGGATTAGATACCCTGGTAGTCCACGCCGTAAAC

GATGAGTACTAGGTGTCGGGGGTTACCCCCCTCGGTGCCGCAGCTAACGCATTAAGTACT

CCGCCTGGGAAGTACGCTCGCAAGAGTGAAACTCAAAGGAATTGACGGGGACCCGCACAA

GTAGCGGAGCATGTGGTTTAATTCGAAGCAACGCGAAGAACCTTACCTAAGCTTGACATC

CCACTGACCTCTCCCTAATCGGAGATTTCCCTTCGGGACAGTGGTGACAGGTGGTGCAT

GGTTGTCGTCAGCTCGTGTCGTGAGATGTTGGGTTAAGTCCCGCAACGAGCGCAACCCTT

GCCTTTAGTTGCCAGCATTAAGTTGGGCACTCTAGAGGGACTGCCGAGGATAACTCGGAG

GAAGGTGGGGATGACGTCAAATCATCATGCCCCTTATGCTTAGGGCTACACACGTGCTAC

AATGGGTGGTACAGAGGGTTGCCAAGCCGCGAGGTGGAGCTAATCCCTTAAAGCCATTCT

CAGTTCGGATTGTAGGCTGAAACTCGCCTACATGAAGCTGGAGTTACTAGTAATCGCAGA

TCAGAATGCTGCGGTGAATGCGTTCCCGGGTCTTGTACACACCGCCCGTCACACCATGGA

AGTTGGGGGCGCCCGAAGCCGGTTAGCTAACCTTTTAGGAAGCGGCCGTCGAA

KK189(1368 bp)
                                                        (SEQ ID NO: 6)
GTCGAGCGATCTCTTCGGAGAGAGCGGCGGACGGGTGAGTAACGCGTGGGTAACCTGCCC

TGTACACACGGATAACATACCGAAAGGTATACTAATACGGGATAACATATGAAAGTCGCA

TGGCTTTTGTATCAAAGCTCCGGCGGTACAGGATGGACCCGCGTCTGATTAGCTAGTTGG

TAAGGTAATGGCTTACCAAGGCAACGATCAGTAGCCGACCTGAGAGGGTGATCGGCCACA

CTGGAACTGAGACACGGTCCAGACTCCTACGGGAGGCAGCAGTGGGGAATATTGCACAAT

GGGCGAAAGCCTGATGCAGCAACGCCGCGTGAGCGATGAAGGCCTTCGGGTCGTAAAGCT

CTGTCCTCAAGGAAGATAATGACGGTACTTGAGGAGGAAGCCCCGGCTAACTACGTGCCA

GCAGCCGCGGTAATACGTAGGGGGCTAGCGTTATCCGGAATTACTGGGCGTAAAGGGTGC

GTAGGTGGTTTTTTAAGTCAGAAGTGAAAGGCTACGGCTCAACCGTAGTAAGCTTTTGAA

ACTAGAGAACTTGAGTGCAGGAGAGGAGAGTAGAATTCCTAGTGTAGCGGTGAAATGCGT

AGATATTAGGAGGAATACCAGTAGCGAAGGCGGCTCTCTGGACTGTAACTGACACTGAGG

CACGAAAGCGTGGGGAGCAAACAGGATTAGATACCCTGGTAGTCCACGCCGTAAACGATG

AGTACTAGGTGTCGGGGGTTACCCCCCTCGGTGCCGCAGCTAACGCATTAAGTACTCCGC

CTGGGAAGTACGCTCGCAAGAGTGAAACTCAAAGGAATTGACGGGGACCCGCACAAGTAG

CGGAGCATGTGGTTTAATTCGAAGCAACGCGAAGAACCTTACCTAAGCTTGACATCCCAC

TGACCTCTCCCTAATCGGAGATTTCCCTTCGGGACAGTGGTGACAGGTGGTGCATGGTT

GTCGTCAGCTCGTGTCGTGAGATGTTGGGTTAAGTCCCGCAACGAGCGCAACCCTTGCCT

TTAGTTGCCAGCATTAAGTTGGGCACTCTAGAGGGACTGCCGAGGATAACTCGGAGGAAG

GTGGGGATGACGTCAAATCATCATGCCCCTTATGCTTAGGGCTACACACGTGCTACAATG

GGTGGTACAGAGGGTTGCCAAGCCGCGAGGTGGAGCTAATCCCTTAAAGCCATTCTCAGT

TCGGATTGTAGGCTGAAACTCGCCTACATGAAGCTGGAGTTACTAGTAATCGCAGATCAG

AATGCTGCGGTGAATGCGTTCCCGGGTCTTGTACACACCGCCCGTCACACCATGGAAGTT

GGGGGCGCCCGAAGCCGGTTAGCTANCCTTTTAGGAAGCGGCCNTCGA

KK 84 (1433 bp)
                                                        (SEQ ID NO: 7)
TGGAAGTCGAACGCTTTTTCTTTCACCGGAGCTTGCTCCACCGAAAGAAAAAGAGTGGCG

AACGGGTGAGTAACACGTGGGTAACCTGCCCATCAGAAGGGGATAACACTTGGAAACAGGT
```

```
GCTAATACCGTATAACACTATTTTCCGCATGGAAGAAAGTTGAAAGGCGCTTTTGCGTCAC

TGATGGATGGACCCGCGGTGCATTAGCTAGTTGGTGAGGTAACGGCTCACCAAGGCAACGA

TGCATAGCCGACCTGAGAGGGTGATCGGCCACACTGGGACTGAGACACGGCCCAGACTCC

TACGGGAGGCAGCAGTAGGGAATCTTCGGCAATGGACGAAAGTCTGACCGAGCAACGCCGCGT

GAGTGAAGAAGGTTTTCGGATCGTAAAACTCTGTTGTTAGAGAAGAACAAGGATGAGAGT

AAAATGTTCATCCCTTGACGGTATCTAACCAGAAAGCCACGGCTAACTACGTGCCAGCAG

CCGCGGTAATACGTAGGTGGCAAGCGTTGTCCGGATTTATTGGGCGTAAAGCGAGCGCAGG

CGGTTTCTTAAGTCTGATGTGAAAGCCCCCGGCTCAACCGGGGAGGGTCATTGGAAACTG

GGAGACTTGAGTGCAGAAGAGGAGAGTGGAATTCCATGTGTAGCGGTGAAATGCGTAGAT

ATATGGAGGAACACCAGTGGCGAAGGCGGCTCTCTGGTCTGTAACTGACGCTGAGGCTCG

AAAGCGTGGGGAGCGAACAGGATTAGATACCCTGGTAGTCCACGCCGTAAACGATGAGTGCTA

AGTGTTGGAGGGTTTCCGCCCTTCAGTGCTGCAGCAAACGCATTAAGCACTCCGCCTGGGG

AGTACGACCGCAAGGTTGAAACTCAAAGGAATTGACGGGGGCCCGCACAAGCGGTGGAGC

ATGTGGTTTAATTCGAAGCAACGCGAAGAACCTTACCAGGTCTTGACATCCTTTGACCACT

CTAGAGATAGAGCTTCCCCTTCGGGGCAAAGTGACAGGTGGTGCATGGTTGTCGTCAGCT

CGTGTCGTGAGATGTTGGGTTAAGTCCCGCAACGAGCGCAACCCTTATTGTTAGTTGCCAT

CATTTAGTTGGGCACTCTAGCGAGACTGCCGGTGACAAACCGGAGGAAGGTGGGGATGAC

GTCAAATCATCATGCCCCTTATGACCTGGGCTACACACGTGCTACAATGGAAGTACAAC

GAGTTGCGAAGTCGCGAGGCTAAGCTAATCTCTTAAAGCTTCTCTCAGTTCGGATTGTAG

GCTGCAACTCGCCTACATGAAGCCGGAATCGCTAGTAATCGCGGATCAGCACGCCGCGGT

GAATACGTTCCCGGGCCTTGTACACACCGCCCGTCACGACCACGAGAGTTTGTAACACCCG

AAGTCGGTGAGGTAACCTTTTTGGAGCCAGCCGCCTAA

KK115 (1431 bp)
                                                    (SEQ ID NO: 8)
TGCAAGTCGAACGCTTCTTTTCCCACCGGAGCTTGCTCCACCGGGAAAAGAGGAGTGGCG

AACGGGTGAGTAACACGTGGGTAACCTGCCCATCAGAAGGGGATAACACTTGGAAACAGG

TGCTAATACCGTATAACAATCGAAACCGCATGGTTTCGTTTTGAAAGGCGCTTTACGGTG

CCGCTGATGGATGGACCCGCGGTGCATTAGCTAGTTGGTGAGGTAACGGCTCACCAAGGC

CACGATGCATAGCCGACCTGAGAGGGTGATCGGCCACATTGGGACTGAGACACGGCCCAA

ACTCCTACGGGAGGCAGCAGTAGGGAATCTTCGGCAATGGACGAAAGTCTGACCGAGCAA

CGCCGCGTGAGTGAAGAAGGTTTTCGGATCGTAAAACTCTGTTGTTAGAGAAGAACAAGG

GTGAGAGTAACTGTTCACCCCTTGACGGTATCTAACCAGAAAGCCACGGCTAACTACGTG

CCAGCAGCCGCGGTAATACGTAGGTGGCAAGCGTTGTCCGGATTTATTGGGCGTAAAGCG

AGCGCAGGCGGTTTCTTAAGTCTGATGTGAAAGCCCCCGGCTCAACCGGGGAGGGTCATT

GGAAACTGGGAGACTTGAGTGCAGAAGAGGAGAGTGGAATTCCATGTGTAGCGGTGAAAT

GCGTAGATATATGGAGGAACACCAGTGGCGAAGGCGGCTCTCTGGTCTGTAACTGACGCT

GAGGCTCGAAAGCGTGGGGAGCAAACAGGATTAGATACCCTGGTAGTCCACGCCGTAAAC

GATGAGTGCTAAGTGTTGGAGGGTTTCCGCCCTTCAGTGCTGCAGCTAACGCATTAAGCA

CTCCGCCTGGGGAGTACGACCGCAAGGTTGAAACTCAAAGGAATTGACGGGGCCCGCA

CAAGCGGTGGAGCATGTGGTTTAATTCGAAGCAACGCGAAGAACCTTACCAGGTCTTGAC

ATCCTTTGACCACTCTAGAGATAGAGCTTCCCCTTCGGGGCAAAGTGACAGGTGGTGCA
```

-continued

TGGTTGTCGTCAGCTCGTGTCGTGAGATGTTGGGTTAAGTCCCGCAACGAGCGCAACCCT

TATTGTTAGTTGCCATCATTTAGTTGGGCACTCTAGCAAGACTGCCGGTGACAAACCGGA

GGAAGGTGGGGATGACGTCAAATCATCATGCCCCTTATGACCTGGGCTACACACGTGCTA

CAATGGGAAGTACAACGAGTCGCGAAGTCGCGAGGCTAAGCTAATCTCTTAAAGCTTCTC

TCAGTTCGGATTGTAGGCTGCAACTCGCCTACATGAAGCCGGAATCGCTAGTAATCGCGG

ATCAGCACGCCGCGGTGAATACGTTCCCGGGCCTTGTACACACCGCCCGTCACACCACGA

GAGTTTGTAACACCCGAAGTCGGTGAGGTAACCTTTTGGAGCCAGCCGCCT

KK149 (SEQ ID NO: 9)

TGCAGTCGTACGCTTTTTCTTTcaCCGGAGCTTGCTCCACCGAAAGAAAAGGAGTGGCGA

ACGGGTGAGTAACACGTGGGTAACCTGCCCATCAGAAGGGGATAACACTTGGAAACAGGT

GCTAATACCGTATAACAATCGAAACCGCATGGTTTTGATTTGAAAGGCGCTTTCGGGTGT

CGCTGATGGATGGACCCGCGGTGCATTAGCTAGTTGGTGAGGTAACGGCTCACCAAGGCC

ACGATGCATAGCCGACCTGAGAGGGTGATCGGCCACATTGGGACTGAGACACGGCCCAAA

CTCCTACGGGAGGCAGCAGTAGGGAATCTTCGGCAATGGACGAAAGTCTGACCGAGCAAC

GCCGCGTGAGTGAAGAAGGTTTTCGGATCGTAAAACTCTGTTGTTAGAGAAGAACAAGGA

TGAGAGTAACTGTTCATCCCTTGACGGTATCTAACCAGAAAGCCACGGCTAACTACGTGC

CAGCAGCCGCGGTAATACGTAGGTGGCAAGCGTTGTCCGGATTTATTGGGCGTAAAGCGA

GCGCAGGCGGTTTCTTAAGTCTGATGTGAAAGCCCCCGGCTCAACCGGGGAGGGTCATTG

GAAACTGGGAGACTTGAGTGCAGAAGAGGAGAGTGGAATTCCATGTGTAGCGGTGAAATG

CGTAGATATATGGAGGAACACCAGTGGCGAAGGCGACTCTCTGGTCTGTAACTGACGCTG

AgGCTCGAAAGCGTGGGGAGCAAACAGGATTAGATACCCTGGTAGTCCACGCCGTAAACG

ATGAGTGCTAAGTOTTGGAGGGTTTCCGCCCTTCAGTGCTGCAGCTAACGCATTAAGCAC

TCCGCCTGGGGAGTACGAcCGCAAGGTTGAAACTCAAAgGAATTGACGGGGCCCGCACA

AGCGGTGGAgCATGTGGTTTAATTCGAAgCAACGCGAAgAACCTTACCaGGTCTTGaCAT

CCTTTGACCACTCTAGAGAtAGAGCTTCCCTTCGGGGCAAAGTGacaGtGtGCATGtgTC

GTC

KK197 (SEQ ID NO: 10)

GCANGTCGTACGCTTCTTTTTCCACCGGAGCTTGCTCCACCGGAAAAAGAGGAGTGGCGA

ACGGGTGAGTAACACGTGGGTAACCTGCCCATCAGAAGGGGATAACACTTGGAAACAGGT

GCTAATACCGTATAACAATCGAAACCGCATGGTTTTGATTTGAAAGGCGCTTTCGGGTGT

CGCTGATGGATGGACCCGCGGTGCATTAGCTAGTTGGTGAGGTAACGGCTCACCAAGGCC

ACGATGCATAGCCGACCTGAGAGGGTGATCGGCCACATTGGGACTGAGACACGGCCCAAA

CTCCTACGGGAGGCAGCAGTAGGGAATCTTCGGCAATGGACGAAAGTCTGACCGAGCAAC

GCCGCGTGAGTGAAGAAGGTTTTCGGATCGTAAAACTCTGTTGTTAGAGAAGAACAAGGA

TGAGAGTAACTGTTCATCCCTTGACGGTATCTAACCAGAAAGCCACGGCTAACTACGTGC

CAGCAGCCGCGGTAATACGTAGGTGGCAAGCGTTGTCCGGATTTATTGGGCGTAAAGCG

AGCGCAGGCGGTTTCTTAAGTCTGATGTGAAAGCCCCCGGCTCAACCGGGGAGGGTCATT

GGAAACTGGGAGACTTGAGTGCAGAAGAGGAGAGTGGAATTCCATGTGTAGCGGTGAAAT

GCGTAGATATATGGAGGAACACCAGTGGCGAAGGCGGCTCTCTGGTCTGTAACTGACGCT

GAGGCTCGAAAGCGTGGGGAGCAAACAGGATTAGATACCCTGGTAGTCCACGCCGTAAAC

GATGAGTGCTAAGTGTTGGAGGGTTTCCGCCCTTCAGTGCTGCAGCTAACGCATTAAGCA

-continued

CTCCGCCTGGGGAGTACGACCGCAAGGTTGAAACTCAAAGGAATTGACGGGGGCCCGCAC

AAGCGGTGGAGCATGTGGTTTAATTCGAAGCAACGCGAAGAACCTTACCAGGTCTTGACA

TCCTTTGACCACTCTAGAGATAGAGCTTCCCCTTCGGGGGCAAAGTGACAGGTGGTGCAT

GGTTGTCGTCAGCTCGTGTCGTGAGATGTTGGGTTAAGTCCCGCAACGAGCGCAACCCTT

ATTGTTAGTTGCCATCATTCAGTTGGGCACTCTAGCAAGACTGCCGGTGACAAACCGGAG

GAAGGTGGGGATGACGTCAAATCATCATGCCCCTTATGACCTGGGCTACACACGTGCTAC

AATGGGAAGTACAACGAGTTGCGAAGTCGCGAGGCTAAGCTAATCTCTTAAAGCTTCTCT

CAGTTCGGATTGCAGGCTGCAACTCGCCTGCATGAAGCCGGAATCGCTAGTAATCGCGGA

TCAGCACGCCGCGGTGAATACGTTCCCGGGCCTTGTACACACCGCCCGTCACACCACGAG

AGTTTGTAACACCCGAAGTCGGTGAGGTAACCTTT

KK.213 (1429 bp)
(SEQ ID NO: 11)
TGCAGTCGTACGCTTCTTTTTCCACCGGAGCTTGCTCCACCGGAAAAAGAGGAGTGGCGA

ACGGGTGAGTAACACGTGGGTAACCTGCCCATCAGAAGGGGATAACACTTGGAAACAGGT

GCTAATACCGTATAACAATCGAAACCGCATGGTTTTGATTTGAAAGGCGCTTTCGGGTGT

CGCTGATGGATGGACCCGCGGTGCATTAGCTAGTTGGTGAGGTAACGGCTCACCAAGGCC

ACGATGCATAGCCGACCTGAGAGGGTGATCGGCCACATTGGGACTGAGACACGGCCCAAA

CTCCTACGGGAGGCAGCAGTAGGGAATCTTCGGCAATGGACGAAAGTCTGACCGAGCAAC

GCCGCGTGAGTGAAGAAGGTTTTCGGATCGTAAAACTCTGTTGTTAGAGAAGAACAAGGA

TGAGAGTAACTGTTCATCCCTTGACGGTATCTAACCAGAAAGCCACGGCTAACTACGTGC

CAGCAGCCGCGGTAATACGTAGGTGGCAAGCGTTGTCCGGATTTATTGGGCGTAAAGCGA

GCGCAGGCGGTTTCTTAAGTCTGATGTGAAAGCCCCCGGCTCAACCGGGGAGGGTCATTG

GAAACTGGGAGACTTGAGTGCAGAAGAGGAGAGTGGAATTCCATGTGTAGCGGTGAAATG

CGTAGATATATGGAGGAACACCAGTGGCGAAGGCGGCTCTCTGGTCTGTAACTGACGCTG

AGGCTCGAAAGCGTGGGGAGCAAACAGGATTAGATACCCTGGTAGTCCACGCCGTAAACG

ATGAGTGCTAAGTGTTGGAGGGTTTCCGCCCTTCAGTGCTGCAGCTAACGCATTAAGCAC

TCCGCCTGGGGAGTACGACCGCAAGGTTGAAACTCAAAGGAATTGACGGGGGCCCGCACA

AGCGGTGGAGCATGTGGTTTAATTCGAAGCAACGCGAAGAACCTTACCAGGTCTTGACAT

CCTTTGACCACTCTAGAGATAGAGCTTCCCCTTCGGGGGCAAAGTGACAGGTGGTGCATG

GTTGTCGTCAGCTCGTGTCGTGAGATGTTGGGTTAAGTCCCGCAACGAGCGCAACCCTTA

TTGTTAGTTGCCATCATTCAGTTGGGCACTCTAGCAAGACTGCCGGTGACAAACCGGAGG

AAGGTGGGGATGACGTCAAATCATCATGCCCCTTATGACCTGGGCTACACACGTGCTACA

ATGGGAAGTACAACGAGTTGCGAAGTCGCGAGGCTAAGCTAATCTCTTAAAGCTTCTCTC

AGTTCGGATTGCAGGCTGCAACTCGCCTGCATGAAGCCGGAATCGCTAGTAATCGCGGAT

CAGCACGCCGCGGTGAATACGTTCCCGGGCCTTGTACACACCGCCCGTCACACCACGAGA

GTTTGTAACACCCGAAGTCGGTGAGGTAACCTTTTGGAGCCAGCCGCCT

KK22
(SEQ ID NO: 12)
CCTAATACATGCAAGTCGAACGCGTTGGCCCAACTGATTGAACGTGCTTGCACGGACTTG

ACGTTGGTTTACCAGCGAGTGGCGGACGGGTGAGTAACACGTAGGTAACCTGCCCCAAAG

CGGGGGATAACATTTGGAAACAGATGCTAATACCGCATAACAATTTGAATCGCATGATTC

AAATTTAAAAGATGGCTTCGGCTATCACTTTGGGATGGACCTGCGGCGCATTAGCTTGTT

-continued

GGTAGGGTAACGGCCTACCAAGGCTGTGATGCGTAGCCGAGTTGAGAGACTGATCGGCCA

CAATGGAACTGAGACACGGTCCATACTCCTACGGGAGGCAGCAGTAGGGAATCTTCCACA

ATGGGCGCAAGCCTGATGGAGCAACACCGCGTGAGTGAAGAAGGGTTTCGGCTCGTAAAG

CTCTGTTGTTAGAGAAGAACGTGCGTGAGAGCAACTGTTCACGCAGTGACGGTATCTAAC

CAGAAAGTCACGGCTAACTACGTGCCAGCAGCCGCGGTAATACGTAGGTGGCAAGCGTTA

TCCGGATTTATTGGGCGTAAAGCGAGCGCAGGCGGTTTGATAAGTCTGATGTGAAAGCCT

TTGGCTTAACCAAAGAAGTGCATCGGAAACTGTCAGACTTGAGTGCAGAAGAGGACAGTG

GAACTCCATGTGTAGCGGTGGAATGCGTAGATATATGGAAGAACACCAGTGGCGAAGGCG

GCTGTCTGGTCTGCAACTGACGCTGAGGCTCGAAAGCATGGGTAGCGAACAGGATTAGAT

ACCCTGGTAGTCCATGCCGTAAACGATGAGTGCTAGGTGTTGGAGGGTTTCCGCCCTTCA

GTGCCGCAGCTAACGCATTAAGCACTCCGCCTGGGGAGTACGACCGCAAGGTTGAAACTC

AAAGGAATTGACGGGGGCCCGCACAAGCGGTGGAGCATGTGGTTTAATTCGAAGCTACGC

GAAGAACCTTACCAGGTCTTGACATCTTGCGCCAACCCTAGAGATAGGGCGTTTCCTTCG

GGAACGCAATGACAGGTGGTGCATGGTCGTCGTCAGCTCGTGTCGTGAGATGTTGGGTTA

AGTCCCGCAACGAGCGCAACCCTTGTTACTAGTTGCCAGCATTCAGTTGGGCACTCTAGT

GAGACTGCCGGTGACAAACCGGAGGAAGGTGGGGACGACGTCAGATCATCATGCCCCTTA

TGACCTGGGCTACACACGTGCTACAATGGACGGTACAACGAGTCGCGAACTCGCGAGGGC

AAGCTAATCTCTTAAAACCGTTCTCAGTTCGGACTGCAGGCTGCAACTCGCCTGCACGAA

GTCGGAATCGCTAGTAATCGCGGATCAGCATGCCGCGGTGAATACGTTCCCGGGCCTTGT

ACACACCGCCCGTCACACCATGAGAGTTTGCAACACCCAAAGTCGGTGGGGTAACCCTTC

GGGGAGCTAGCCGCCT

KK223

(SEQ ID NO: 13)
CGAGCGATGAAGCTTCCTTCGGGAAGTGGATTAGCGGCGGACGGGTGAGTAACACGTGGG

TAACCTGCCTCAAAGTGGGGGATAGCCTTCCGAAAGGAAGATTAATACCGCATAACATAA

GAGAATCGCATGATTTTCTTATCAAAGATTTATTGCTTTGAGATGGACCCGCGGCGCATT

AGCTAGTTGGTAAGGTAACGGCTTACCAAGGCAACGATGCGTAGCCGACCTGAGAGGGTG

ATCGGCCACATTGGAACTGAGACACGGTCCAGACTCCTACGGGAGGCAGCAGTGGGGAAT

ATTGCGCAATGGGGGAAACCCTGACGCAGCAACGCCGCGTGGGTGATGAAGGTCTTCGGA

TTGTAAAGCCCTGTTTTCTGGGACGATAATGACGGTACCAGAGGAGGAAGCCACGGCTAA

CTACGTGCCAGCAGCCGCGGTAATACGTAGGTGGCGAGCGTTGTCCGGATTTACTGGGCG

TAAAGGGTGCGTAGGCGGATGTTTAAGTGGGATGTGAAATCCCCGGGCTTAACCTGGGGG

CTGCATTCCAAACTGGATATCTAGAGTGCAGGAGAGGAAAGCGGAATTCCTAGTGTAGCG

GTGAAATGCGTAGAGATTAGGAAGAACACCAGTGGCGAAGGCGGCTTTCTGGACTGTAAC

TGACGCTGAGGCACGAAAGCGTGGGTAGCAAACAGGATTAGATACCCTGGTAGTCCACGC

CGTAAACGATGGATACTAGGTGTAGGGGGTATCAACTCCCCCTGTGCCGCAGTTAACACA

ATAAGTATCCCGCCTGGGGAGTACGGTCGCAAGATTAAAACTCAAAGGAATTGACGGGGG

CCCGCACAAGCAGCGGAGCATGTGGTTTAATTCGAAGCAACGCGAAGAACCTTACCTGGA

CTTGACATCCCTTGCATAGCCTAGAGATAGGTGAAGCCCTTCGGGGCAAGGAGACAGGTG

GTGCATGGTTGTCGTCAGCTCGTGTCGTGAGATGTTAGGTTAAGTCCTGCAACGAGCGCA

ACCCTTGTTATTAGTTGCTACCATTAAGTTGAGCACTCTAATGAGACTGCCTGGGTAACC

AGGAGGAAGGTGGGGATGACGTCAAATCATCATGCCCCTTATGTCCAGGGCTACACACGT

```
GCTACAATGGTAGGTACAATAAGACGCAAGACCGTGAGGTGGAGCAAAACTTATAAAACC

TATCTCAGTTCGGATTGTAGTGCTGCAACTCGCCTACATGAAGCTGGAGTTGCTAGTAAT

CGCGAATCAGAATGTCGCGGTGAATACGTTCCCGGGCCTTGTACACACCGCCCGTCACAC

CATGAGAGCTGGTAACACCCGAAGTCCGTGAGGTAACCGTAAGGAGCCAGC
```

KK232                                                        (SEQ ID NO: 14)
```
CCAGAAAgccACGGCTAAcTACGtgCCAGCAGCCGCGGTAATACGTAGGtGGCAAGCGTt GTCcGGATTTATTGGGCGTAAAGCGAGCGCAGGCGGTTTCTTAAGTcTGATGTGAAAGCC

CCCGGCTCAACCGGGGAGGGTCATTGGAAACTGGGAGACTTGAGTGCAGAAGAGGAGAGT

GGAATTCCATGTGTAGCGGTGAAATGCGTAGATATATGGAGGAACACCAGTGGCGAAGGC

GACTCTCTGGTCTGTAACTGACGCTGAGGCTCGAAAGCGTGGGGAGCAAACAGGATTAGA

TACCCTGGTAGTCCACGCCGTAAACGATGAGTGCTAAGTGTTGGAGGGTTTCCGCCCTTC

AGTGCTGCAGCTAACGCATTAAGCACTCCGCCTGGGGAGTACGACCGCAAGGTTGAAACT

CAAAGGAATTGACGGGGGCCCGCACAAGCGGTGGAGCATGTGGTTTAATTCGAAGCAACG

CGAAGAACCTTACCAGGTCTTGACATCCTTTGACCACTCTAGAGATAGAGCTTCCCCTTC

GGGGGCAAAGTGACAGGTGGTGCATGGTTGTCGTCAGCTCGTGTCGTGAGATGTTGGGTT

AAGTCCCGCAACGAGCGCAACCCTTATTGTTAGTTGCCATCATTAAGTTGGGCACTCTAG

CAAGACTGCCGGTGACAAACCGGAGGAAGGTGGGGATGACGTCAAATCATCATGCCCCTT

ATGACCTGGGCTACACACGTGCTACAATGGGAAGTACAACGAGTCGCGAAGTCGCGAGGC

TAAGCTAATCTCTTAAAGCTTCTCTCAGTTCGGATTGTAGGCTGCAACTCGCCTACATGA

AGCCGGAATCGCTAGTAATCGCGGATCAGCACGCCGCGGTGAATACGTTCCCGGGCctTG

TNCACACCGCCcgtCaCaCCACGAAAGTTTGTAACACCCgAAGTCGGTGAGGTAaCCTTT
```

KK241                                                        (SEQ ID NO: 15)
```
AGAGTACtgTCATCCcTGACGGTATcTAcCagAAGCCaCGGCTAAcTACGTGCCAGCAGC

CGCGGTAATACGTAGGTGGCAAGCGTTGTCcGGATTTATTGGGCGTAAAGCGAGCGCAGG

CGGTTTcTTAAgTCTGATGTGAAAGCCCCCGGCTCAACCGGGGAGGGTCATTGGAAACTG

GGAGACTTGAGTGCAGAAGAGGAGAGTGGAATTCCATGTGTAGCGGTGAAATGCGTAGAT

ATATGGAGGAACACCAGTGGCGAAGGCGACTCTCTGGTCTGTAACTGACGCTGAGGCTCG

AAAGCGTGGGGAGCAAACAGGATTAGATACCCTGGTAGTCCACGCCGTAAACGATGAGTG

CTAAGTGTTGGAGGGTTTCCGCCCTTCAGTGCTGCAGCTAACGCATTAAGCACTCCGCCT

GGGGAGTACGACCGCAAGGTTGAAACTCAAAGGAATTGACGGGGCCCGCACAAGCGGTG

GAGCATGTGGTTTAATTCGAAGCAACGCGAAGAACCTTACCAGGTCTTGACATCCTTTGA

CCACTCTAGAGATAGAGCTTCCCCTTCGGGGGCAAAGTGACAGGTGGTGCATGGTTGTCG

TCAGCTCGTGTCGTGAGATGTTGGGTTAAGTCCCGCAACGAGCGCAACCCTTATTGTTAG

TTGCCATCATTAAGTTGGGCACTCTAGCAAGACTGCCGGTGACAAACCGGAGGAAGGTGG

GGATGACGTCAAATCATCATGCCCCTTATGACCTGGGCTACACACGTGcTACAATGGGAA

GTACAACGAGTcGCGAAGTCGCGAGGCTAAGCTAATCTCTTAAAGCTTCTCTCAGTTCGG

ATTGTAGGCTGCAACTCGCCTACATGAAGCCGGAATCGCTAGTAATCGCGGATCAGCACG

CCGCGGTGAATACGTTCCCGGGCCTTGTACACACCGCCCGTCACACCACGAAAGTTTGTA

ACACCCGAAGTCGGTGAGGTAaCCTTTtGGAGCCAgCCGCC
```

KK245

(SEQ ID NO: 16)
CGTACGCTTCTTTTTCCACCGGAGCTTGCTCCACCGGAAAAAGAGGAGTGGCGAACGGGT
GAGTAACACGTGGGTAACCTGCCCATCAGAAGGGGATAACACTTGGAAACAGGTGCTAAT
ACCGTATAACAATCGAAACCGCATGGTTTTGATTTGAAAGGCGCTTTCGGGTGTCGCTGA
TGGATGGACCCGCGGTGCATTAGCTAGTTGGTGAGGTAACGGCTCACCAAGGCCACGATG
CATAGCCGACCTGAGAGGGTGATCGGCCACATTGGGACTGAGACACGGCCCAAACTCCTA
CGGGAGGCAGCAGTAGGGAATCTTCGGCAATGGACGAAAGTCTGACCGAGCAACGCCGCG
TGAGTGAAGAAGGTTTTCGGATCGTAAAACTCTGTTGTTAGAGAAGAACAAGGATGAGAG
TAACTGTTCATCCCTTGACGGTATCTAACCAGAAAGCCACGGCTAACTACGTGCCAGCAG
CCGCGGTAATACGTAGGTGGCAAGCGTTGTCCGGATTTATTGGGCGTAAAGCGAGCGCAG
GCGGTTTCTTAAGTCTGATGTGAAAGCCCCCGGCTCAACCGGGGAGGGTCATTGGAAACT
GGGAGACTTGAGTGCAGAAGAGGAGAGTGGAATTCCATGTGTAGCGGTGAAATGCGTAGA
TATATGGAGGAACACCAGTGGCGAAGGCGGCTCTCTGGTCTGTAACTGACGCTGAGGCTC
GAAAGCGTGGGGAGCAAACAGGATTAGATACCCTGGTAGTCCACGCCGTAAACGATGAGT
GCTAAGTGTTGGAGGGTTTCCGCCCTTCAGTGCTGCAGCTAACGCATTAAGCACTCCGCC
TGGGGAGTACGACCGCAAGGTTGAAACTCAAAGGAATTGACGGGGGCCCGCACAAGCGGT
GGAGCATGTGGTTTAATTCGAAGCAACGCGAAGAACCTTACCAGGTCTTGACATCCTTTG
ACCACTCTAGAGATAGAGCTTCCCCTTCGGGGGCAAAGTGACAGGTGGTGCATGGTTGTC
GTCAGCTCGTGTCGTGAGATGTTGGGTTAAGTCCCGCAACGAGCGCAACCCTTATTGTTA
GTTGCCATCATTCAGTTGGGCACTCTAGCAAGACTGCCGGTGACAAACCGGAGGAAGGTG
GGGATGACGTCAAATCATCATGCCCCTTATGACCTGGGCTACACACGTGCTACAATGGGA
AGTACAACGAGTTGCGAAGTCGCGAGGCTAAGCTAATCTCTTAAAGCTTCTCTCAGTTCG
GATTGCAGGCTGCAACTCGCCTGCATGAAGCCGGAATCGCTAGTAATCGCGGATCAGCAC
GCCGCGGTGAATACGTTCCCGGGCCTTGTACACACCGCCCGTCACACCACGAGAGTTTGT
AACACCCGAAGTCGGTGAGGTAACCTTT

KK247

(SEQ ID NO: 17)
acaCGAAGTGAGTGGCGGACGGGTGAGTAACACGTGGGTAACCTGCCCAGAAGCAGGGGA
TAACACCTGGAAACAGATGCTAATACCGTATAACAGAGAAAACCGCCTGGTTTTCTTTTA
AAAGATGGCTCTGCTATCACTTCTGGATGGACCCGCGGCGCATTAGCTAGTTGGTGAGGT
AACGGCTCACCAAGGCGATGATGCGTAGCCGACCTGAGAGGGTAATCGGCCACATTGGGA
CTGAGACACGGCCCAGACTCCTACGGGAGGCAGCAGTAGGGAATCTTCCACAATGGACGC
AAGTCTGATGGAGCAACGCCGCGTGAGTGAAGAAGGGTTTCGGCTCGTAAAGCTCTGTTG
TTAAAGAAGAACGTGGGTGAGAGTAACTGTTCACCCAGTGACGGTATTTAACCAGAAAGC
CACGGCTAACTACGTGCCAGCAGCCGCGGTAATACGTAGGTGGCAAGCGTTATCCGGATT
TATTGGGCGTAAAGCGAGCGCAGGCGGTCTTTTAAGTCTAATGTGAAAGCCTTCGGCTCA
ACCGAAGAAGTGCATTGGAAACTGGGAGACTTGAGTGCagAAGAGGACAGTGGAACTCCA
TGTGTAGCGGTGAAATGCGTAGATATATGGAAGAACACCAGTGGCGAAggCGGCTGTCTG
GTCTGTAACTGACGCTGAggCTCGAAAGCATGGGTAGCGAACAGGATTAGATACCCTGGT
AGTCCATGCCGTAAACGATGATTACTAAGTGTTGGAGGGTTCCGCCCTTCAGTGCTGCA
GCTAACGCATTAAGTAATCCGCCTGGgGAGTACgACCGCAAGGTTGAAACTCAAAAGAAT -continued TGACGGGCCCGCACaAgCGGtGGAGCATGTGG

KK52

(SEQ ID NO: 18)

TACATGCAAGTCGAGCGAACAGACGAGGAGCTTGCTCCTCTGACGTTAGCGGCGGACGGG

TGAGTAACACGTGGATAACCTACCTATAAGACTGGGATAACTTCGGGAAACCGGAGCTAA

TACCGGATAATATATTGAACCGCATGGTTCAATAGTGAAAGACGGTTTTGCTGTCACTTA

TAGATGGATCCGCGCCGCATTAGCTAGTTGGTAAGGTAACGGCTTACCAAGGCAACGATG

CGTAGCCGACCTGAGAGGGTGATCGGCCACACTGGAACTGAGACACGGTCCAGACTCCTA

CGGGAGGCAGCAGTAGGGAATCTTCCGCAATGGGCGAAAGCCTGACGGAGCAACGCCGCG

TGAGTGATGAAGGTCTTCGGATCGTAAAACTCTGTTATTAGGGAAGAACAAATGTGTAAG

TAACTATGCACGTCTTGACGGTACCTAATCAGAAAGCCACGGCTAACTACGTGCCAGCAG

CCGCGGTAATACGTAGGTGGCAAGCGTTATCCGGAATTATTGGGCGTAAAGCGCGCGTAG

GCGGTTTTTTAAGTCTGATGTGAAAGCCCACGGCTCAACCGTGGAAGGTCATTGGAAACT

GGAAAACTTGAGTGCAGAAGAAGAAAGTGGAATTCCATGTGTAGCGGTGAAATGCGCAGA

AATATGGAGGAACACCAGTGGCGAAGGCGACTTTCTGGTCTGTAACTGACGCTGATGTGC

GAAAGCGTGGGGATCAAACAGGATTAAATACCCTGGTAGTCCACGCCGTAAACGATGAAT

GCTAAGTGGTAGGGGGTTTCCGCCCCTTAATGCTGCAGCTAACGCATTAAGCACTCCGCC

TGGGGAGTACGACCGCAAGGTTGAAACTCAAAGGAATTGACGGGACCCGCACAAGCGGT

GGAGCATGTGGTTTAATTCGAAGCAACGCGAAGAACCTTACCAAATCTTGACATCCTCTG

ACCCCTCTAGAGATAGAGTTTTCCCCTTCGGGGACAGAGTGACAGGTGGTGCATGGTTG

TCGTCAGCTCGTGTCGTGAGATGTTGGGTTAAGTCCCGCAACGAGCGCAACCCTTAAGCT

TAGTTGCCATCATTAAGTTGGGCACTCTAAGTTGACTGCCGGTGACAAACCGGAGGAAGG

TGGGGATGACGTCAAATCATCATGCCCCTTATGATTTGGGCTACACACGTGCTACAATGG

ACAATACAAAGGGCAGCGAAACCGCGAGGTCAAGCAAATCCCATAAAGTTGTTCTCAGTT

CGGATTGTAGTCTGCAACTCGACTATATGAAGCTGGAATCGCTAGTAATCGTAGATCAGC

ATGCTACGGTGAATACGTTCCCGGGTCTTGTACACACCGCCCGTCACACCACGAGAGTTT

GTAACACCCGAAGCCGGTGGAGTAACCATTGGAGCTA

KK80

(SEQ ID NO: 19)

TGCAGTCGAACGCTTTTTCTTTCACCGGAGCTTGCTCCACCGAAAGAAAAAGAGTGGCGA

ACGGGTGAGTAACACGTGGGTAACCTGCCCATCAGAAGGGGATAACACTTGGAAACAGGT

GCTAATACCGTATAACACTATTTTCCGCATGGAAGAAAGTTGAAAGGCGCTTTTGCGTCA

CTGATGGATGGACCCGCGGTGCATTAGCTAGTTGGTGAGGTAACGGCTCACCAAGGCAAC

GATGCATAGCCGACCTGAGAGGGTGATCGGCCACACTGGGACTGAGACACGGCCCAGACT

CCTACGGGAGGCAGCAGTAGGGAATCTTCGGCAATGGACGAAAGTCTGACCGAGCAACGC

CGCGTGAGTGAAGAAGGTTTTCGGATCGTAAAACTCTGTTGTTAGAGAAGAACAAGGATG

AGAGTAAAATGTTCATCCCTTGACGGTATCTAACCAGAAAGCCACGGCTAACTACGTGCC

AGCAGCCGCGGTAATACGTAGGTGGCAAGCGTTGTCCGGATTTATTGGGCGTAAAGCGAG

CGCAGGCGGTTTCTTAAGTCTGATGTGAAAGCCCCCGGCTCAACCGGGGAGGGTCATTGG

AAACTGGGAGACTTGAGTGCAGAAGAGGAGAGTGGAATTCCATGTGTAGCGGTGAAATGC

GTAGATATATGGAGGAACACCAGTGGCGAAGGCGGCTCTCTGGTCTGTAACTGACGCTGA

GGCTCGAAAGCGTGGGGAGCGAACAGGATTAGATACCCTGGTAGTCCACGCCGTAAACGA

TGAGTGCTAAGTGTTGGAGGGTTTCCGCCCTTCAGTGCTGCAGCAAACGCATTAAGCACT

```
CCGCCTGGGGAGTACGACCGCAAGGTTGAAACTCAAAGGAATTGACGGGGGCCCGCACAA

GCGGTGGAGCATGTGGTTTAATTCGAAGCAACGCGAAGAACCTTACCAGGTCTTGACATC

CTTTGACCACTCTAGAGATAGAGCTTCCCCTTCGGGGGCAAAGTGACAGGTGGTGCATGG

TTGTCGTCAGCTCGTGTCGTGAGATGTTGGGTTAAGTCCCGCAACGAGCGCAACCCTTAT

TGTTAGTTGCCATCATTTAGTTGGGCACTCTAGCGAGACTGCCGGTGACAAACCGGAGGA

AGGTGGGGATGACGTCAAATCATCATGCCCCTTATGACCTGGGCTACACACGTGCTACAA

TGGGAAGTACAACGAGTTGCGAAGTCGCGAGGCTAAGCTAATCTCTTAAAGCTTCTCTCA

GTTCGGATTGTAGGCTGCAACTCGCCTACATGAAGCCGGAATCGCTAGTAATCGCGGATC

AGCACGCCGCGGTGAATACGTTCCCGGGCCTTGTACACACCGCCCGTCACACCACGAGAG

TTTGTAACACCCGAAGTCGGTGAGGTAACCTTTTTGGAGCCAGCCGC
```

For convenience, the information provided above obtained by BLAST searches is summarized below.

Although it has been demonstrated that 16S rRNA gene sequence data on an individual strain with a nearest neighbor exhibiting a similarity score of <97% represents anew species, the meaning of similarity scores of >97% is not as clear (Petti, C. A. 2007. Detection and identification of microorganisms by gene amplification and sequencing. Clin. Infect. Dis. 44: 1108-1114. [PubMed].).

Whereas 16S rRNA gene sequence data can be used for multiplicity of purposes, unlike DNA hybridization (>70% reassociation) there are no defined "threshold values" (e.g., 98.5% similarity) above which there is universal agreement of what constitutes definitive and conclusive identification to a given bacterial species.

However, (>97%) is commonly used as a benchmark of species identity for bacteria.

TABLE 5

Identification of selected organisms that produce ethanol from cellobiose. All cultured species deposited to NCBI that match 97% or more nucleic acids are indicated.

| Number | Phylum | Class | Order | Family | Genus | Species | Base | Match | ≥% |
|---|---|---|---|---|---|---|---|---|---|
| 22 | Firmicutes | Bacilli | Lactobacillales | Lactobacillaceae | Lactobacillus | mucosae | 1456 | 1456/1456 | 100 |
|  |  |  |  |  |  | fermentum |  | 1450/1452 | 99 |
| 52 | Firmicutes | Bacilli | Bacillales | Staphylococcaceae | Staphylococcus | epidermidis | 1417 | 1410/1417 | 99 |
| 80 | Firmicutes | Bacilli | Lactobacillales | Enterococcaceae | Enterococcus | casselitlavus | 1427 | 1427/1428 | 99 |
|  |  |  |  |  |  | gallinarum |  | 1425/1428 | 99 |
|  |  |  |  |  |  | saccharolyticus |  | 1419/1424 | 99 |
| 84 | Firmicutes | Bacilli | Lactobacillales | Enterococcaceae | Enterococcus | casselitlavus | 1433 | 1429/1430 | 99 |
|  |  |  |  |  |  | gallinarum |  | 1427/1430 | 99 |
|  |  |  |  |  |  | saccharolyticus |  | 1424/1432 | 99 |
| 149 | Firmicutes | Clostridia | Clostridiales | Clostridiaceae | Clostridium | bifermentans | 1389 | 1373/1384 | 99 |
|  |  |  |  |  |  | sordellii |  | 1371/1381 | 99 |
| 157 | Firmicutes | Clostridia | Clostridiales | Clostridiaceae | Clostridium | bifermentans | 1376 | 1372/1379 | 99 |
|  |  |  |  |  |  | sordellii |  | 1349/1380 | 97 |
| 188 | Firmicutes | Clostridia | Clostridiales | Clostridiaceae | Clostridium | bifermentans | 1373 | 1373/1374 | 99 |
|  |  |  |  |  |  | sordellii |  | 1349/1375 | 98 |
| 189 | Firmicutes | Clostridia | Clostridiales | Clostridiaceae | Clostridium | sordellii | 1368 | 1366/1368 | 99 |
|  |  |  |  |  |  | bifermentans |  | 1365/1368 | 99 |
| 115 | Firmicutes | Bacilli | Lactobacillales | Enterococcaceae | Enterococcus | mundtii | 1431 | 1430/1431 | 99 |
|  |  |  |  |  |  | hirae |  | 1420/1432 | 99 |
|  |  |  |  |  |  | faecium |  | 1419/1432 | 99 |
|  |  |  |  |  |  | durans |  | 1415/1427 | 99 |
| 197 | Firmicutes | Bacilli | Lactobacillales | Enterococcaceae | Enterococcus | faecium | 1415 | 1413/1415 | 99 |
|  |  |  |  |  |  | lactis |  | 1413/1515 | 99 |
|  |  |  |  |  |  | faecalis |  | 1412/1415 | 99 |
| 213 | Firmicutes | Bacilli | Lactobacillales | Enterococcaceae | Enterococcus | lactis | 1429 | 1429/1430 | 99 |
|  |  |  |  |  |  | faecium |  | 1428/1429 | 99 |
| 223 | Firmicutes | Clostridia | Clostridiales | Closrridiaceae | Clostridium | sporogenes | 1371 | 1370/1371 | 99 |
|  |  |  |  |  |  | botulinum |  | 1370/1371 | 99 |
| 232 | Firmicutes | Bacilli | Lactobacillales | Enterococcaceae | Enterococcus | sanguinicola | 960 | 958/960 | 99 |
|  |  |  |  |  |  | thailandicus |  | 958/960 | 99 |
|  |  |  |  |  |  | mundtii |  | 9561960 | 99 |
|  |  |  |  |  |  | durans |  | 9561960 | 99 |
|  |  |  |  |  |  | faecium |  | 9551960 | 99 |
|  |  |  |  |  |  | hirae |  | 9551960 | 99 |
|  |  |  |  |  |  | pseudoavium |  | 9541960 | 99 |
|  |  |  |  |  |  | gilvus |  | 954/960 | 99 |
| 241 | Firmicutes | Bacilli | Lactobacillales | Enterococcaceae | Enterococcus | sanguinicola | 1001 | 1000/1006 | 99 |
|  |  |  |  |  |  | thailandicus |  | 1000/1007 | 99 |
|  |  |  |  |  |  | durans |  | 998/1006 | 99 |
|  |  |  |  |  |  | faecium |  | 997/1006 | 99 |

TABLE 5-continued

Identification of selected organisms that produce ethanol from cellobiose. All cultured species deposited to NCBI that match 97% or more nucleic acids are indicated.

| Number | Phylum | Class | Order | Family | Genus | Species | Base | Match | ≥% |
|---|---|---|---|---|---|---|---|---|---|
| | | | | | | hirae | | 997/1006 | 99 |
| | | | | | | mundtii | | 996/1007 | 99 |
| | | | | | | pemyi | | 997/1007 | 99 |
| | | | | | | faecalis | | 99511006 | 98 |
| | | | | | | gilvus | | | |
| 245 | Firmicutes | Bacilli | Lactobacillales | Enterococcaceae | Enterococcus | lactis | 1408 | 1408/1408 | 100 |
| | | | | | | faecium | | 1407/1408 | 99 |
| | | | | | | faecalis | | 1407/1408 | 99 |
| | | | | | | durans | | 1403/1408 | 99 |
| 247 | Firmicutes | Bacilli | Lactobacillales | Lactobacillaceae | Pediococcus | acidilactici | 873 | 873/874 | 99 |
| | | | | | | pentosaceus | | 863/875 | 98 |

Identification of selected organisms that produce ethanol from cellobiose. All cultured species deposited to NCBI that match 97% or more nucleic acids are indicated.

Closest Species

*Clostridium bifermentans*

*Clostridium sordellii*

*Clostridium sporogenes*

*Enterococcus casseliflavus*

*Enterococcus muntii*

*Enterococcus sanguinicola*

*Enterococcus faecium*

*Enterococcus lactis*

*Pediococcus acidilactici*

*Lactobacillus mucosae*

*Staphylococcus epidermidis* (grows by aerobic respiration). Many are lactic acid bacteria but when isolated without $H_2$ or selecting non-acid producers gave other types.

*Clostridium* are strict anaerobes. *Enterococcus* or *Lactobacillus* or *Pediococcus* tolerate oxygen and *Staphylococcus epidermidis* grows by aerobic respiration or fermentation. 245 cultured for 2 months on AVICEL® (microcrystalline cellulose).

247 isolated from 5% butanol and tolerates 10% ethanol 115, 189 convert about 50% cellobiose to ethanol when ethanol exceeds 6% (not as high a conversion when ethanol is not present)

213 converts most cellobiose to ethanol even without ethanol present, also digests AVICEL® (microcrystalline cellulose) well to ethanol.

Finally, as noted above in the section on Term Definitions, and as used herein, the phrase "conversion percentage by weight" means the percentage of cellulose weight converted to ethanol or other biofuel, such as propanol or butanol, for example. As noted also, these calculations do not include exogenous water or hydrogen that may also be incorporated into produced ethanol, for example. For example, 50% conversion of cellulose by weight means that 1 g of cellulose is converted to 0.5 g of ethanol, for example. Nearly as much $CO_2$ may be produced, which if included in the product yield would lead to higher conversion percentage. Generally, the theoretical maximum yield of ethanol from cellulose, in accordance with the present invention, is about 57% by weight, unless the $CO_2$ also produced is also converted, but this requires more $H_2$.

Having described the present invention, it will be apparent that many changes and modifications may be made to the above-described embodiments without departing from the spirit and the scope of the present invention.

What is claimed is:

1. A process for digesting and fermenting cellulosic biomass in a fermentation vessel, wherein the cellulosic biomass is inoculated with selected microorganisms, and wherein said selected microorganisms were selected for their ability to digest the cellulosic biomass and convert at least 30% by weight of digested cellulosic biomass to ethanol in a broth comprising at least 5% ethanol by volume, and wherein the selected microorganisms comprise a member of a taxonomic genus from among: *Ruminococcus, Enterococcus, Clostridium, Pediococcus, Lactobacillus*, and *Staphylococcus*.

2. The process of claim 1, wherein the cellulosic biomass is combined with a fermentation broth comprising the selected microorganisms, and the selected microorganisms in the fermentation broth convert at least 30% by weight of the digested cellulosic biomass to ethanol, and wherein ethanol concentration in the fermentation broth reaches a volume of at least 5% of the fermentation broth volume.

3. The process of claim 1, wherein the cellulosic biomass is combined with a fermentation broth comprising the selected microorganisms, and the selected microorganisms in the fermentation broth convert cellulosic biomass to ethanol when ethanol volume reaches at least 7% of the fermentation broth volume.

4. The process of claim 1, wherein at least 50% by weight of the digested cellulosic biomass is converted to ethanol.

5. The process of claim 1, wherein partial pressure of hydrogen gas is increased in the fermentation vessel by adding or recirculating the hydrogen gas.

6. The process of claim 1, wherein partial pressure of hydrogen gas in the fermentation vessel is at least 0.02 atm.

7. The process of claim 1, wherein a reducing agent is added to the fermentation vessel.

8. The process of claim 1, wherein the cellulosic biomass is chopped or pulverized.

9. The process of claim 1, wherein water or liquid is added to the cellulosic biomass in the fermentation vessel.

10. The process of claim 1, which further comprises adding sulfite to the fermentation vessel.

11. A process for digesting and fermenting cellulosic biomass, wherein the cellulosic biomass is combined with a fermentation broth comprising ethanol-adapted microorganisms; and wherein said ethanol-adapted microorganisms were selected for their ability to produce ethanol from cellulosic biomass in a fermentation broth with at least 5% ethanol concentration by volume of the fermentation broth, and wherein said ethanol-adapted microorganisms comprise a member of a taxonomic genus from among: *Ruminococcus, Enterococcus, Clostridium, Pediococcus, Lactobacillus*, and *Staphylococcus*.

12. The process of claim 11, wherein a mixture of the cellulosic biomass and the fermentation broth produces ethanol when the ethanol concentration reaches a volume of at least 7% of the fermentation broth volume.

13. A process for digesting and fermenting cellulosic biomass in a fermentation vessel with a microbial culture in a fermentation broth, comprising the steps: (a) inoculating the cellulosic biomass with microorganisms that were selected for their ability to grow on cellulosic biomass and produce lower alkyl alcohol in a broth comprising at least 2% lower alkyl alcohol by volume; and (b) adding or re-circulating hydrogen gas into the fermentation vessel.

14. The process of claim 13, wherein concentration of lower alkyl alcohol reaches at least 4% by volume of the fermentation broth.

15. The process of claim 13, wherein the lower alkyl alcohol comprises ethanol.

16. The process of claim 13, wherein the lower alkyl alcohol comprises propanol.

17. The process of claim 13, wherein the lower alkyl alcohol comprises butanol.

18. The process of claim 13, wherein the hydrogen gas partial pressure in the fermentation vessel is at least 0.02 atmospheres.

19. The process of claim 13, wherein co-products of the process are fed to animals.

20. A method of digesting and fermenting cellulosic biomass with a microbial culture to produce butanol, wherein said method comprises the steps: (a) inoculating the cellulosic biomass with microorganisms selected for their ability to digest the cellulosic biomass and produce butanol; (b) wherein the microbial culture digests the cellulosic biomass and produces butanol in a fermentation broth; (c) wherein the fermentation broth comprises at least 0.5% butanol concentration by volume; and (d) removing the butanol from the fermentation broth.

21. The process of claim 20, wherein the microbial culture comprises microorganisms selected for their ability to digest the cellulosic biomass in a fermentation broth comprising at least 2% butanol concentration by volume.

* * * * *

SEQUENCE LISTING

```
<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agtttgatcc tggctcag                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggytaccttg ttacgactt                                                19
```

<210> SEQ ID NO 3
<211> LENGTH: 1389
<212> TYPE: DNA
<213> ORGANISM: Clostridium sp.

<400> SEQUENCE: 3

| | | | | | |
|---|---|---|---|---|---|
| ctaccatgca | gtcgagcgat | ctcttcggag | agagcggcgg | acgggtgagt | aacgcgtggg | 60 |
| taacctgccc | tgtacacacg | gataacatac | cgaaaggtat | actaatacgg | gataacatat | 120 |
| gaaagtcgca | tggctttgt | atcaaagctc | cggcggtaca | ggatggaccc | gcgtctgatt | 180 |
| agctagttgg | taaggtaatg | gcttaccaag | gcaacgatca | gtagccgacc | tgagagggtg | 240 |
| atcggccaca | ctggaactga | gacacggtcc | agactcctac | gggaggcagc | agtggggaat | 300 |
| attgcacaat | gggcgaaagc | ctgatgcagc | aacgccgcgt | gagcgatgaa | ggccttcggg | 360 |
| tcgtaaagct | ctgtcctcaa | ggaagataat | gacggtactt | gaggaggaag | ccccggctaa | 420 |
| ctacgtgcca | gcagccgccg | taatacgtag | ggggctagcg | ttattccgga | attactgggc | 480 |
| gtaaagggt | gcgtaggtgg | ttttttaagt | cagaagtgaa | aggctacggc | tcaaccgtag | 540 |
| taagctttg | aaactagaga | acttgagtgc | aggagaggga | agtagaattc | ctagtgtagc | 600 |
| ggtgaaatgc | gtagatatta | ggaggaatac | cagtagcgaa | ggcggctctc | tggactgtaa | 660 |
| ctgacactga | ggcacgaaag | cgtggggagc | aaacaggatt | agataccctg | gtagtccacg | 720 |
| ccgtaaacga | tgagtactag | gtgtcggggg | ttaccccct | cggtgccgca | gctaacgcat | 780 |
| taagtactcc | gcctgggaag | tacgctcgca | agagtgaaac | tcaaaggaat | tgacggggac | 840 |
| ccgcacaagt | agcggagcca | tgtggtttaa | ttcgaaagca | acgcgaagaa | ccttacctaa | 900 |
| gcttgacatc | ccactgacct | ctcccctaat | cggagatttc | ccttcgggga | cagtggtgac | 960 |
| aggtggtgca | tggttgtcgt | caagctcgtg | tcctgagatg | ttgggttaag | tcccgcaacg | 1020 |
| agcgcaaccc | ttgcctttag | ttgccagcat | taagttgggc | actctagagg | gactgccgag | 1080 |
| gataactcgg | aggaaggtgg | ggatgacgtc | aaatcatcat | gccccttatg | cttagggcta | 1140 |
| cacacgtgct | acaatgggtg | gtacagaggg | ttgccaagcc | gcgaggtgga | gctaatccct | 1200 |
| taaagccatt | ctcagttcgg | attgtaggct | gaaactcgcc | tacatgaagc | tggagttact | 1260 |
| agtaatcgca | gatcagaatg | ctgcggtgaa | tgcgttcccg | ggtcttgtac | acaccgcccg | 1320 |
| tcacaccatg | gaagttgggg | gcgcccgaag | ccggttagct | aacctttagg | aagcggcctc | 1380 |
| gaaggaacc | | | | | | 1389 |

<210> SEQ ID NO 4
<211> LENGTH: 1376
<212> TYPE: DNA
<213> ORGANISM: Clostridium sp.

<400> SEQUENCE: 4

| | | | | | |
|---|---|---|---|---|---|
| tgcagtcgag | cgatctcttc | ggagagagcg | gcggacgggt | gagtaacgcg | tgggtaacct | 60 |
| gccctgtaca | cacggataac | ataccgaaag | gtatactaat | acgggataac | atacgaaagt | 120 |
| cgcatggctt | ttgtatcaaa | gctccggcgg | tacaggatgg | acccgcgtct | gattagctag | 180 |
| ttggtaaggt | aatggcttac | caaggcaacg | atcagtagcc | gacctgagag | ggtgatcggc | 240 |
| cacactggaa | ctgagacacg | gtccagactc | ctacgggagg | cagcagtggg | gaatattgca | 300 |
| caatgggcga | aagcctgatg | cagcaacgcc | gcgtgagcga | tgaaggcctt | cgggtcgtaa | 360 |
| agctctgtcc | tcaaggaaga | taatgacggt | acttgaggag | gaagcccgc | taactacgtg | 420 |

```
ccagcagccg cggtaatacg taggggggcta gcgttatccg gaattactgg gcgtaaaggg      480
tgcgtaggtg gttttttaag tcagaagtga aaggctacgg ctcaaccgta gtaagctttt      540
gaaactagag aacttgagtg caggagagga gagtagaatt cctagtgtag cggtgaaatg      600
cgtagatatt aggaggaata ccagtagcga aggcggctct ctggactgta actgacactg      660
aggcacgaaa gcgtggggag caaacaggat tagataccct ggtagtccac gccgtaaacg      720
atgagtacta ggtgtcgggg gttacccccc tcggtgccgc agctaacgca ttaagtactc      780
cgcctgggga agtacgctcg caagagtgaa actcaaagga attgacgggg acccgcacaa      840
gtagcggagc atgtggttta attcgaagca acgcgaagaa ccttacctaa gcttgacatc      900
ccactgacct ctccctaatc ggagatttcc cttcgggaac agtggttgac aggtgggtgc      960
atggttgtcg tcagctcgtg tcgtgagatg ttgggttaag tcccgcaacg agcgcaaccc     1020
ttgcctttag ttgccagcat taagttgggc actctagagg gactgccgag gataactcgg     1080
aggaaggtgg ggatgacgtc aaatcatcat gccccttatg cttagggcta cacacgtgct     1140 acaatggggtg gtacagaggg ttgccaagcc gcgaggtgga gctaatccct taaagccatt     1200
ctcagttcgg attgtaggct gaaactcgcc tacatgaagc tggagttact agtaatcgca     1260
gatcagaatg ctgcggtgaa tgcgttcccg ggtcttgtac acaccgcccg tcacaccatg     1320
gaagttgggg gcgcccgaag ccggttagct aacctttttag gaagcggcct cgaagg       1376
```

<210> SEQ ID NO 5
<211> LENGTH: 1373
<212> TYPE: DNA
<213> ORGANISM: Clostridium sp.

<400> SEQUENCE: 5

```
tgcagtcgag cgatctcttc ggagagagcg gcggacgggt gagtaacgcg tgggtaacct       60
gccctgtaca cacggataac ataccgaaag gtatactaat acgggataac atacgaaagt      120
cgcatggctt ttgtatcaaa gctccggcgg tacaggatgg acccgcgtct gattagctag      180
ttggtaaggt aatggcttac caaggcaacg atcagtagcc gacctgagag ggtgatcggc      240
cacactggaa ctgagacacg gtccagactc ctacggggagg cagcagtggg gaatattgca      300
caatgggcga aagcctgatg cagcaacgcc gcgtgagcga tgaaggcctt cgggtcgtaa      360
agctctgtcc tcaaggaaga taatgacggt acttgaggag gaagccccgg ctaactacgt      420
gccagcagcc gcggtaatac gtaggggggct agcgttatcc ggaattactg ggcgtaaagg      480
gtgcgtaggt ggtttttttaa gtcagaagtg aaaggctacg gctcaaccgt agtaagcttt      540
tgaaactaga gaacttgagt gcaggagagg agagtagaat tcctagtgta gcggtgaaat      600
gcgtagatat taggaggaat accagtagcg aaggcggctc tctggactgt aactgacact      660
gaggcacgaa agcgtgggga gcaaacagga ttagataccc tggtagtcca cgccgtaaac      720
gatgagtact aggtgtcggg ggttacccccc ctcggtgccg cagctaacgc attaagtact      780 ccgcctgggga agtacgctcg caagagtgaa actcaaagga attgacgggg acccgcacaa      840
gtagcggagc atgtggttta attcgaagca acgcgaagaa ccttacctaa gcttgacatc      900
ccactgacct ctccctaatc ggagatttcc cttcggggac agtggtgaca ggtggtgcat      960
ggttgtcgtc agctcgtgtc gtgagatgtt gggttaagtc ccgcaacgag cgcaaccctt     1020
gcctttagtt gccagcatta gttgggcac tctagaggga ctgccgagga taactcggag     1080
gaaggtgggg atgacgtcaa atcatcatgc cccttatgct tagggctaca cacgtgctac     1140 aatggggtggt acagagggtt gccaagccgc gaggtggagc taatccctta aagccattct     1200
```

-continued

```
cagttcggat tgtaggctga aactcgccta catgaagctg gagttactag taatcgcaga      1260
tcagaatgct gcggtgaatg cgttcccggg tcttgtacac accgcccgtc acaccatgga      1320 agttggggge ccccgaagcc ggttagctaa ccttttagga agcggccgtc gaa             1373
```

<210> SEQ ID NO 6
<211> LENGTH: 1368
<212> TYPE: DNA
<213> ORGANISM: Clostridium sp.
<220> FEATURE:
<221> NAME/KEY: modified_base
<222> LOCATION: (1346)..(1346)
<223> OTHER INFORMATION: a, c, g, t, unknown or other
<220> FEATURE:
<221> NAME/KEY: modified_base
<222> LOCATION: (1364)..(1364)
<223> OTHER INFORMATION: a, c, g, t, unknown or other

<400> SEQUENCE: 6

```
gtcgagcgat ctcttcggag agagcggcgg acgggtgagt aacgcgtggg taacctgccc        60
tgtacacacg ataacatac cgaaaggtat actaatacgg gataacatat gaaagtcgca       120
tggcttttgt atcaaagctc cggcggtaca ggatggaccc cgtctgatt agctagttgg       180 taaggtaatg gcttaccaag gcaacgatca gtagccgacc tgagagggtg atcggccaca      240
ctggaactga gacacggtcc agactcctac gggaggcagc agtggggaat attgcacaat      300
gggcgaaagc ctgatgcagc aacgccgcgt gagcgatgaa ggccttcggg tcgtaaagct      360
ctgtcctcaa ggaagataat gacggtactt gaggaggaag ccccggctaa ctacgtgcca      420
gcagccgcgg taatacgtag ggggctagcg ttatccggaa ttactgggcg taaagggtgc      480
gtaggtggtt ttttaagtca gaagtgaaag gctacggctc aaccgtagta agcttttgaa      540
actagagaac ttgagtgcag gagaggagag tagaattcct agtgtagcgg tgaaatgcgt      600
agatattagg aggaataccag gtagcgaagg cggctctctg gactgtaact gacactgagg      660
cacgaaagcg tggggagcaa acaggattag ataccctggt agtccacgcc gtaaacgatg      720
agtactaggt gtcgggggtt acccccctcg gtgccgcagc taacgcatta agtactccgc      780
ctgggaagta cgctcgcaag agtgaaactc aaaggaattg acgggaccc gcacaagtag       840 cggagcatgt ggtttaattc gaagcaacgc gaagaacctt acctaagctt gacatcccac      900
tgacctctcc ctaatcggag atttccttc ggggacagtg tgacaggtg gtgcatggtt        960 gtcgtcagct cgtgtcgtga gatgttgggt taagtcccgc aacgagcgca acccttgcct     1020
ttagttgcca gcattaagtt gggcactcta gaggactgc cgaggataac tcggaggaag      1080
gtggggatga cgtcaaatca tcatgcccct tatgcttagg gctacacacg tgctacaatg     1140
ggtggtacag agggttgcca agccgcgagg tggagctaat ccttaaagc cattctcagt      1200 tcggattgta ggctgaaact cgcctacatg aagctggagt tactagtaat cgcagatcag     1260
aatgctgcgc tgaatgcgtt cccgggtctt gtacacaccg cccgtcacac catggaagtt     1320
gggggcgccc gaagccggtt agctanccttt taggaagcg gccntcga                  1368
```

<210> SEQ ID NO 7
<211> LENGTH: 1433
<212> TYPE: DNA
<213> ORGANISM: Enterococcus sp.

<400> SEQUENCE: 7

```
tggaagtcga acgcttttc tttcaccgga gcttgctcca ccgaaagaaa aagagtggcg        60
```

| | |
|---|---:|
| aacgggtgag taacacgtgg gtaacctgcc catcagaagg ggataacact tggaaacagg | 120 |
| tgctaatacc gtataacact attttccgca tggaagaaag ttgaaaggcg cttttgcgtc | 180 |
| actgatggat ggacccgcgg tgcattagct agttggtgag gtaacggctc accaaggcaa | 240 |
| cgatgcatag ccgacctgag agggtgatcg gccacactgg gactgagaca cggcccagac | 300 |
| tcctacggga ggcagcagta gggaatcttc ggcaatggac gaaagtctga ccgagcaacg | 360 |
| ccgcgtgagt gaagaaggtt ttcggatcgt aaaactctgt tgttagagaa gaacaaggat | 420 |
| gagagtaaaa tgttcatccc ttgacggtat ctaaccagaa agccacggct aactacgtgc | 480 |
| cagcagccgc ggtaatacgt aggtggcaag cgttgtcggg atttattggg cgtaaagcga | 540 |
| gcgcaggcgg tttcttaagt ctgatgtgaa agccccggc tcaaccgggg agggtcattg | 600 |
| gaaactggga gacttgagtg cagaagagga gagtggaatt ccatgtgtag cggtgaaatg | 660 |
| cgtagatata tggaggaaca ccagtggcga aggcggctct ctggtctgta actgacgctg | 720 |
| aggctcgaaa gcgtggggag cgaacaggat tagataccct ggtagtccac gccgtaaacg | 780 |
| atgagtgcta agtgttggag ggtttccgcc cttcagtgct gcagcaaacg cattaagcac | 840 |
| tccgcctggg gagtacgacc gcaaggttga aactcaaagg aattgacggg ggcccgcaca | 900 |
| agcggtggag catgtggttt aattcgaagc aacgcgaaga accttaccag gtcttgacat | 960 |
| cctttgacca ctctagagat agagcttccc cttcggggc aaagtgacag gtggtgcatg | 1020 |
| gttgtcgtca gctcgtgtcg tgagatgttg ggttaagtcc cgcaacgagc gcaacccta | 1080 |
| ttgttagttg ccatcattta gttgggcact ctagcgagac tgccggtgac aaaccggagg | 1140 |
| aaggtgggga tgacgtcaaa tcatcatgcc ccttatgacc tgggctacac acgtgctaca | 1200 |
| atgggaagta caacgagttg cgaagtcgcg aggctaagct aatctcttaa agcttctctc | 1260 |
| agttcggatt gtaggctgca actcgcctac atgaagccgg aatcgctagt aatcgcggat | 1320 |
| cagcacgccg cggtgaatac gttcccgggc cttgtacaca ccgcccgtca cgaccacgag | 1380 |
| agtttgtaac acccgaagtc ggtgaggtaa cctttttgga gccagccgcc taa | 1433 |

<210> SEQ ID NO 8
<211> LENGTH: 1431
<212> TYPE: DNA
<213> ORGANISM: Enterococcus sp.

<400> SEQUENCE: 8

| | |
|---|---:|
| tgcaagtcga acgcttcttt tcccaccgga gcttgctcca ccgggaaaag aggagtggcg | 60 |
| aacgggtgag taacacgtgg gtaacctgcc catcagaagg ggataacact tggaaacagg | 120 |
| tgctaatacc gtataacaat cgaaaccgca tggtttcgtt ttgaaaggcg ctttacggtg | 180 |
| ccgctgatgg atggacccgc ggtgcattag ctagttggtg aggtaacggc tcaccaaggc | 240 |
| cacgatgcat agccgacctg agagggtgat cggccacatt gggactgaga cacggcccaa | 300 |
| actcctacgg gaggcagcag tagggaatct cggcaatgg acgaaagtct gaccgagcaa | 360 |
| cgccgcgtga gtgaagaagg ttttcggatc gtaaaactct gttgttagag aagaacaagg | 420 |
| gtgagagtaa ctgttcaccc cttgacggta tctaaccaga aagccacggc taactacgtg | 480 |
| ccagcagccg cggtaatacg taggtggcaa gcgttgtccg gatttattgg gcgtaaagcg | 540 |
| agcgcaggcg gtttcttaag tctgatgtga aagccccggc tcaaccggg gagggtcatt | 600 |
| ggaaactggg agacttgagt gcagaagagg agagtggaat tccatgtgta gcggtgaaat | 660 |
| gcgtagatat atggaggaac accagtggcg aaggcggctc tctggtctgt aactgacgct | 720 |
| gaggctcgaa agcgtgggga gcaaacagga ttagataccc tggtagtcca cgccgtaaac | 780 |

```
gatgagtgct aagtgttgga gggtttccgc ccttcagtgc tgcagctaac gcattaagca    840
ctccgcctgg gggagtacga ccgcaaggtt gaaactcaaa ggaattgacg ggggcccgca    900
caagcggtgg agcatgtggt ttaattcgaa gcaacgcgaa gaaccttacc aggtcttgac    960
atcctttgac cactctagag atagagcttc cccttcgggg gcaaagtgac aggtggtgca   1020
tggttgtcgt cagctcgtgt cgtgagatgt tgggttaagt cccgcaacga gcgcaaccct   1080
tattgttagt tgccatcatt tagttgggca ctctagcaag actgccggtg acaaaccgga   1140
ggaaggtggg gatgacgtca atcatcatg ccccttatga cctgggctac acacgtgcta   1200
caatgggaag tacaacgagt cgcgaagtcg cgaggctaag ctaatctctt aaagcttctc   1260
tcagttcgga ttgtaggctg caactcgcct acatgaagcc ggaatcgcta gtaatcgcgg   1320
atcagcacgc cgcggtgaat acgttccgg gccttgtaca caccgcccgt cacaccacga   1380
gagtttgtaa cacccgaagt cggtgaggta accttttgga gccagccgcc t            1431
```

<210> SEQ ID NO 9
<211> LENGTH: 1023
<212> TYPE: DNA
<213> ORGANISM: Enterococcus sp.

<400> SEQUENCE: 9

```
tgcagtcgta cgcttttct ttcaccggag cttgctccac cgaaagaaaa ggagtggcga     60
acgggtgagt aacacgtggg taacctgccc atcagaaggg gataacactt ggaaacaggt    120
gctaataccg tataacaatc gaaaccgcat ggttttgatt tgaaaggcgc tttcgggtgt    180
cgctgatgga tggacccgcg gtgcattagc tagttggtga ggtaacggct caccaaggcc    240
acgatgcata gccgacctga gagggtgatc ggccacattg gactgagac acggcccaaa    300 ctcctacggg aggcagcagt agggaatctt cggcaatgga cgaaagtctg accgagcaac    360
gccgcgtgag tgaagaaggt tttcggatcg taaaactctg ttgttagaga agaacaagga    420
tgagagtaac tgttcatccc ttgacggtat ctaaccagaa agccacggct aactacgtgc    480
cagcagccgc ggtaatacgt aggtggcaag cgttgtccgg atttattggg cgtaaagcga    540
gcgcaggcgg tttcttaagt ctgatgtgaa agccccggc tcaaccgggg agggtcattg    600
gaaactggga gacttgagtg cagaagagga gagtggaatt ccatgtgtag cggtgaaatg    660
cgtagatata tggaggaaca ccagtggcga aggcgactct ctggtctgta actgacgctg    720
aggctcgaaa gcgtggggag caaacaggat tagataccct ggtagtccac gccgtaaacg    780
atgagtgcta agtgttggag ggtttccgcc cttcagtgct gcagctaacg cattaagcac    840
tccgcctggg gagtacgacc gcaaggttga aactcaaagg aattgacggg gcccgcaca    900 agcggtggag catgtggttt aattcgaagc aacgcgaaga accttaccag tcttgacat    960 cctttgacca ctctagagat agagcttccc ttcgggcaa agtgacagtg tgcatgtgtc   1020
gtc                                                                 1023
```

<210> SEQ ID NO 10
<211> LENGTH: 1415
<212> TYPE: DNA
<213> ORGANISM: Enterococcus sp.
<220> FEATURE:
<221> NAME/KEY: modified_base
<222> LOCATION: (4)..(4)
<223> OTHER INFORMATION: a, c, g, t, unknown or other

<400> SEQUENCE: 10

```
gcangtcgta cgcttctttt tccaccggag cttgctccac cggaaaaaga ggagtggcga        60
acgggtgagt aacacgtggg taacctgccc atcagaaggg gataacactt ggaaacaggt       120
gctaataccg tataacaatc gaaaccgcat ggttttgatt tgaaaggcgc tttcgggtgt       180
cgctgatgga tggacccgcg gtgcattagc tagttggtga ggtaacggct caccaaggcc       240
acgatgcata gccgacctga gagggtgatc ggccacattg ggactgagac acggcccaaa       300
ctcctacggg aggcagcagt agggaatctt cggcaatgga cgaaagtctg accgagcaac       360
gccgcgtgag tgaagaaggt tttcggatcg taaaactctg ttgttagaga agaacaagga       420
tgagagtaac tgttcatccc ttgacggtat ctaaccagaa agccacggct aactacgtgc       480
cagcagccgc ggtaatacgg taggtggcaa gcgttgtccg gatttattgg gcgtaaagcg       540
agcgcaggcg gtttcttaag tctgatgtga aagcccccgg ctcaaccggg agggtcatt       600 ggaaactggg agacttgagt gcagaagagg agagtggaat tccatgtgta gcggtgaaat       660
gcgtagatat atggaggaac accagtggcg aaggcggctc tctggtctgt aactgacgct       720
gaggctcgaa agcgtgggga gcaaacagga ttagataccc tggtagtcca cgccgtaaac       780
gatgagtgct aagtgttgga gggtttccgc ccttcagtgc tgcagctaac gcattaagca       840
ctccgcctgg ggagtacgac cgcaaggttg aaactcaaag gaattgacgg gggcccgcac       900
aagcggtgga gcatgtggtt taattcgaag caacgcgaag aaccttacca ggtcttgaca       960
tcctttgacc actctagaga tagagcttcc ccttcggggg caaagtgaca ggtggtgcat      1020
ggttgtcgtc agctcgtgtc gtgagatgtt gggttaagtc ccgcaacgag cgcaacccttt      1080 attgttagtt gccatcattc agttgggcac tctagcaaga ctgccggtga caaaccggag      1140
gaaggtgggg atgacgtcaa atcatcatgc cccttatgac ctgggctaca cacgtgctac      1200
aatgggaagt acaacgagtt gcgaagtcgc gaggctaagc taatctctta aagcttctct      1260
cagttcggat tgcaggctgc aactcgcctg catgaagccg gaatcgctag taatcgcgga      1320
tcagcacgcc gcggtgaata cgttcccggg ccttgtacac accgcccgtc acaccacgag      1380
agtttgtaac acccgaagtc ggtgaggtaa ccttt                                 1415
```

<210> SEQ ID NO 11
<211> LENGTH: 1429
<212> TYPE: DNA
<213> ORGANISM: Enterococcus sp.

<400> SEQUENCE: 11

```
tgcagtcgta cgcttctttt tccaccggag cttgctccac cggaaaaaga ggagtggcga        60
acgggtgagt aacacgtggg taacctgccc atcagaaggg gataacactt ggaaacaggt       120
gctaataccg tataacaatc gaaaccgcat ggttttgatt tgaaaggcgc tttcgggtgt       180
cgctgatgga tggacccgcg gtgcattagc tagttggtga ggtaacggct caccaaggcc       240
acgatgcata gccgacctga gagggtgatc ggccacattg ggactgagac acggcccaaa       300
ctcctacggg aggcagcagt agggaatctt cggcaatgga cgaaagtctg accgagcaac       360
gccgcgtgag tgaagaaggt tttcggatcg taaaactctg ttgttagaga agaacaagga       420
tgagagtaac tgttcatccc ttgacggtat ctaaccagaa agccacggct aactacgtgc       480
cagcagccgc ggtaatacgt aggtggcaag cgttgtccgg atttattggg cgtaaagcga       540
gcgcaggcgg tttcttaagt ctgatgtgaa agccccggc tcaaccgggg agggtcattg       600
gaaactggga gacttgagtg cagaagagga gagtggaatt ccatgtgtag cggtgaaatg       660
cgtagatata tggaggaaca ccagtggcga aggcggctct ctggtctgta actgacgctg       720
```

```
aggctcgaaa gcgtggggag caaacaggat tagataccct ggtagtccac gccgtaaacg      780
atgagtgcta agtgttggag ggtttccgcc cttcagtgct gcagctaacg cattaagcac      840
tccgcctggg gagtacgacc gcaaggttga aactcaaagg aattgacggg ggcccgcaca      900
agcggtggag catgtggttt aattcgaagc aacgcgaaga accttaccag gtcttgacat      960
cctttgacca ctctagagat agagcttccc cttcggggc aaagtgacag gtggtgcatg     1020
gttgtcgtca gctcgtgtcg tgagatgttg ggttaagtcc cgcaacgagc gcaaccctta     1080
ttgttagttg ccatcattca gttgggcact ctagcaagac tgccggtgac aaaccggagg     1140
aaggtgggga tgacgtcaaa tcatcatgcc ccttatgacc tgggctacac acgtgctaca     1200
atgggaagta caacgagttg cgaagtcgcg aggctaagct aatctcttaa agcttctctc     1260
agttcggatt gcaggctgca actcgcctgc atgaagccgg aatcgctagt aatcgcggat     1320
cagcacgccg cggtgaatac gttcccgggc cttgtacaca ccgcccgtca caccacgaga     1380
gtttgtaaca cccgaagtcg gtgaggtaac cttttggagc cagccgcct                 1429

<210> SEQ ID NO 12
<211> LENGTH: 1456
<212> TYPE: DNA
<213> ORGANISM: Lactobacillus sp.

<400> SEQUENCE: 12
cctaatacat gcaagtcgaa cgcgttggcc caactgattg aacgtgcttg cacggacttg       60
acgttggttt accagcgagt ggcggacggg tgagtaacac gtaggtaacc tgccccaaag      120
cgggggataa catttggaaa cagatgctaa taccgcataa caatttgaat cgcatgattc      180
aaatttaaaa gatggcttcg gctatcactt tgggatggac ctgcggcgca ttagcttgtt      240
ggtagggtaa cggcctacca aggctgtgat gcgtagccga gttgagagac tgatcggcca      300
caatggaact gagacacggt ccatactcct acgggaggca gcagtaggga atcttccaca      360
atgggcgcaa gcctgatgga gcaacaccgc gtgagtgaag aagggtttcg gctcgtaaag      420
ctctgttgtt agagaagaac gtgcgtgaga gcaactgttc acgcagtgac ggtatctaac      480
cagaaagtca cggctaacta cgtgccagca gccgcggtaa tacgtaggtg gcaagcgtta      540
tccggattta ttgggcgtaa agcgagcgca ggcggtttga taagtctgat gtgaaagcct      600
ttggcttaac caaagaagtg catcggaaac tgtcagactt gagtgcagaa gaggacagtg      660
gaactccatg tgtagcggtg gaatgcgtag atatatggaa gaacaccagt ggcgaaggcg      720
gctgtctggt ctgcaactga cgctgaggct cgaaagcatg ggtagcgaac aggattagat      780
accctggtag tccatgccgt aaacgatgag tgctaggtgt tggagggttt ccgcccttca      840
gtgccgcagc taacgcatta agcactccgc ctggggagta cgaccgcaag gttgaaactc      900
aaaggaattg acggggcccc gcacaagcgg tggagcatgt ggtttaattc gaagctacgc      960
gaagaacctt accaggtctt gacatcttgc gccaacccta gagatagggc gtttccttcg     1020
ggaacgcaat gacaggtggt gcatggtcgt cgtcagctcg tgtcgtgaga tgttgggtta     1080
agtcccgcaa cgagcgcaac ccttgttact agttgccagc attcagttgg cactctagt      1140 gagactgccg gtgacaaacc ggaggaaggt ggggacgacg tcagatcatc atgcccctta     1200
tgacctgggc tacacacgtg ctacaatgga cggtacaacg agtcgcgaac tcgcgagggc     1260
aagctaatct cttaaaaccg ttctcagttc ggactgcagg ctgcaactcg cctgcacgaa     1320
gtcggaatcg ctagtaatcg cggatcagca tgccgcggtg aatacgttcc cgggccttgt     1380
```

```
acacaccgcc cgtcacacca tgagagtttg caacacccaa agtcggtggg gtaacccttc    1440
ggggagctag ccgcct                                                    1456

<210> SEQ ID NO 13
<211> LENGTH: 1371
<212> TYPE: DNA
<213> ORGANISM: Clostridium sp.

<400> SEQUENCE: 13
cgagcgatga agcttccttc gggaagtgga ttagcggcgg acgggtgagt aacacgtggg      60
taacctgcct caaagtgggg gatagccttc cgaaaggaag attaataccg cataacataa     120
gagaatcgca tgattttctt atcaaagatt tattgctttg agatggaccc gcggcgcatt     180
agctagttgg taaggtaacg gcttaccaag gcaacgatgc gtagccgacc tgagagggtg     240
atcggccaca ttggaactga gacacggtcc agactcctac gggaggcagc agtggggaat     300
attgcgcaat gggggaaacc ctgacgcagc aacgccgcgt gggtgatgaa ggtcttcgga     360
ttgtaaagcc ctgttttctg gacgataat  gacggtacca gaggaggaag ccacggctaa     420
ctacgtgcca gcagccgcgg taatacgtag gtggcgagcg ttgtccggat ttactgggcg     480
taaagggtgc gtaggcggat gtttaagtgg gatgtgaaat ccccgggctt aacctggggg     540
ctgcattcca aactggatat ctagagtgca ggagaggaaa gcggaattcc tagtgtagcg     600
gtgaaatgcg tagagattag gaagaacacc agtggcgaag cggctttct  ggactgtaac     660 tgacgctgag gcacgaaagc gtgggtagca acaggatta  gataccctgg tagtccacgc     720
cgtaaacgat ggatactagg tgtaggggggt atcaactccc cctgtgccgc agttaacaca     780
ataagtatcc cgcctgggga gtacggtcgc aagattaaaa ctcaaaggaa ttgacggggg     840
cccgcacaag cagcggagca tgtggtttaa ttcgaagcaa cgcgaagaac cttacctgga     900
cttgacatcc cttgcatagc ctagagatag gtgaagccct cggggcaag  gagacaggtg     960 gtgcatggtt gtcgtcagct cgtgtcgtga tgttaggt  taagtcctgc aacgagcgca    1020
acccttgtta ttagttgcta ccattaagtt gagcactcta atgagactgc ctgggtaacc    1080
aggaggaagg tggggatgac gtcaaatcat catgcccctt atgtccaggg ctacacacgt    1140
gctacaatgg taggtacaat aagacgcaag accgtgaggt ggagcaaaac ttataaaacc    1200
tatctcagtt cggattgtag tgctgcaact cgcctacatg aagctggagt tgctagtaat    1260
cgcgaatcag aatgtcgcgg tgaatacgtt cccgggcctt gtacacaccg cccgtcacac    1320
catgagagct ggtaacaccc gaagtccgtg aggtaaccgt aaggagccag c             1371

<210> SEQ ID NO 14
<211> LENGTH: 960
<212> TYPE: DNA
<213> ORGANISM: Enterococcus sp.
<220> FEATURE:
<221> NAME/KEY: modified_base
<222> LOCATION: (902)..(902)
<223> OTHER INFORMATION: a, c, g, t, unknown or other

<400> SEQUENCE: 14
ccagaaagcc acggctaact acgtgccagc agccgcggta atacgtaggt ggcaagcgtt      60
gtccggattt attgggcgta aagcgagcgc aggcggtttc ttaagtctga tgtgaaagcc     120
cccggctcaa ccggggaggg tcattggaaa ctgggagact tgagtgcaga agaggagagt     180
ggaattccat gtgtagcggt gaaatgcgta gatatatgga ggaacaccag tggcgaaggc     240
gactctctgg tctgtaactg acgctgaggc tcgaaagcgt ggggagcaaa caggattaga     300
```

```
taccctggta gtccacgccg taaacgatga gtgctaagtg ttggagggtt tccgcccttc    360
agtgctgcag ctaacgcatt aagcactccg cctggggagt acgaccgcaa ggttgaaact    420
caaaggaatt gacggggggcc cgcacaagcg gtggagcatg tggtttaatt cgaagcaacg   480
cgaagaacct taccaggtct tgacatcctt tgaccactct agagatagag cttccccttc    540
gggggcaaag tgacaggtgg tgcatggttg tcgtcagctc gtgtcgtgag atgttgggtt    600
aagtcccgca acgagcgcaa cccttattgt tagttgccat cattaagttg ggcactctag    660
caagactgcc ggtgacaaac cggaggaagg tggggatgac gtcaaatcat catgccctt    720 atgacctggg ctacacacgt gctacaatgg aagtacaac gagtcgcgaa gtcgcgaggc    780
taagctaatc tcttaaagct tctctcagtt cggattgtag gctgcaactc gcctacatga    840
agccggaatc gctagtaatc gcggatcagc acgccgcggt gaatacgttc ccgggccttg    900
tncacaccgc ccgtcacacc acgaaagttt gtaacacccg aagtcggtga ggtaacccttt    960
```

<210> SEQ ID NO 15
<211> LENGTH: 1001
<212> TYPE: DNA
<213> ORGANISM: Enterococcus sp.

<400> SEQUENCE: 15

```
agagtactgt catccctgac ggtatctacc agaagccacg gctaactacg tgccagcagc     60
cgcggtaata cgtaggtggc aagcgttgtc cggatttatt gggcgtaaag cgagcgcagg    120
cggtttctta agtctgatgt gaaagccccc ggctcaaccg ggagggtca ttggaaactg    180 ggagacttga gtgcagaaga ggagagtgga attccatgtg tagcggtgaa atgcgtagat    240
atatggagga acaccagtgg cgaaggcgac tctctggtct gtaactgacg ctgaggctcg    300
aaagcgtggg gagcaaacag gattagatac cctggtagtc cacgccgtaa acgatgagtg    360
ctaagtgttg gagggtttcc gcccttcagt gctgcagcta acgcattaag cactccgcct    420
ggggagtacg accgcaaggt tgaaactcaa aggaattgac ggggccccgc acaagcggtg    480
gagcatgtgg tttaattcga agcaacgcga agaaccttac caggtcttga catcctttga    540
ccactctaga gatagagctt cccccttcggg ggcaaagtga caggtggtgc atggttgtcg    600
tcagctcgtg tcgtgagatg ttgggttaag tcccgcaacg agcgcaaccc ttattgttag    660
ttgccatcat taagttgggc actctagcaa gactgccggt gacaaacggg aggaaggtgg    720
ggatgacgtc aaatcatcat gccccttatg acctgggcta cacacgtgct acaatgggaa    780
gtacaacgag tcgcgaagtc gcgaggctaa gctaatctct taaagcttct ctcagttcgg    840
attgtaggct gcaactcgcc tacatgaagc cggaatcgct agtaatcgcg gatcagcacg    900
ccgcggtgaa tacgttcccg ggccttgtac acaccgcccg tcacaccacg aaagtttgta    960
acacccgaag tcggtgaggt aaccttttgg agccagccgc c                         1001
```

<210> SEQ ID NO 16
<211> LENGTH: 1408
<212> TYPE: DNA
<213> ORGANISM: Enterococcus sp.

<400> SEQUENCE: 16

```
cgtacgcttc tttttccacc ggagcttgct ccaccggaaa agaggagtg gcgaacgggt     60 gagtaacacg tgggtaacct gcccatcaga aggggataac acttggaaac aggtgctaat    120
accgtataac aatcgaaacc gcatggtttt gatttgaaag gcgctttcgg gtgtcgctga    180
```

```
tggatggacc cgcggtgcat tagctagttg gtgaggtaac ggctcaccaa ggccacgatg      240
catagccgac ctgagagggt gatcggccac attgggactg agacacggcc caaactccta      300
cgggaggcag cagtagggaa tcttcggcaa tggacgaaag tctgaccgag caacgccgcg      360
tgagtgaaga aggttttcgg atcgtaaaac tctgttgtta gagaagaaca aggatgagag      420
taactgttca tcccttgacg gtatctaacc agaaagccac ggctaactac gtgccagcag      480
ccgcggtaat acgtaggtgg caagcgttgt ccggatttat tgggcgtaaa gcgagcgcag      540
gcggtttctt aagtctgatg tgaaagcccc cggctcaacc ggggagggtc attggaaact      600
gggagacttg agtgcagaag aggagagtgg aattccatgt gtagcggtga aatgcgtaga      660
tatatggagg aacaccagtg gcgaaggcgg ctctctggtc tgtaactgac gctgaggctc      720
gaaagcgtgg ggagcaaaca ggattagata ccctggtagt ccacgccgta acgatgagt      780 gctaagtgtt ggagggtttc cgcccttcag tgctgcagct aacgcattaa gcactccgcc      840
tggggagtac gaccgcaagg ttgaaactca aaggaattga cggggcccg cacaagcggt      900 ggagcatgtg gtttaattcg aagcaacgcg aagaaccta ccaggtcttg acatcctttg      960
accactctag agatagagct tccccttcgg gggcaaagtg acaggtggtg catggttgtc     1020
gtcagctcgt gtcgtgagat gttgggttaa gtcccgcaac gagcgcaacc cttattgtta     1080
gttgccatca ttcagttggg cactctagca agactgccgg tgacaaaccg gaggaaggtg     1140
gggatgacgt caaatcatca tgccccttat gacctgggct acacacgtgc tacaatggga     1200
agtacaacga gttgcgaagt cgcgaggcta agctaatctc ttaaagcttc tctcagttcg     1260
gattgcaggc tgcaactcgc ctgcatgaag ccggaatcgc tagtaatcgc ggatcagcac     1320
gccgcggtga atacgttccc gggccttgta cacaccgccc gtcacaccac gagagtttgt     1380
aacacccgaa gtcggtgagg taaccttt                                       1408

<210> SEQ ID NO 17
<211> LENGTH: 873
<212> TYPE: DNA
<213> ORGANISM: Pediococcus sp.

<400> SEQUENCE: 17
acacgaagtg agtggcggac gggtgagtaa cacgtgggta acctgcccag aagcagggga       60
taacacctgg aaacagatgc taataccgta taacagagaa aaccgcctgg ttttcttta      120 aaagatggct ctgctatcac ttctggatgg acccgcggcg cattagctag ttggtgaggt      180
aacggctcac caaggcgatg atgcgtagcc gacctgagag ggtaatcggc cacattggga      240
ctgagacacg gcccagactc ctacgggagg cagcagtagg gaatcttcca caatggacgc      300
aagtctgatg gagcaacgcc gcgtgagtga agaagggttt cggctcgtaa agctctgttg      360
ttaaagaaga acgtgggtga gagtaactgt tcacccagtg acggtattta accagaaagc      420
cacggctaac tacgtgccag cagccgcggt aatacgtagg tggcaagcgt tatccggatt      480
tattgggcgt aaagcgagcg caggcggtct tttaagtcta atgtgaaagc cttcggctca      540
accgaagaag tgcattggaa actgggagac ttgagtgcag aagaggacag tggaactcca      600
tgtgtagcgg tgaaatgcgt agatatatgg aagaacacca gtggcgaagg cggctgtctg      660
gtctgtaact gacgctgagg ctcgaaagca tgggtagcga acaggattag ataccctggt      720
agtccatgcc gtaaacgatg attactaagt gttggagggt ttccgccctt cagtgctgca      780
gctaacgcat taagtaatcc gcctgggag tacgaccgca aggttgaaac tcaaaagaat      840
tgacggggcc cgcacaagcg gtggagcatg tgg                                   873
```

<210> SEQ ID NO 18
<211> LENGTH: 1417
<212> TYPE: DNA
<213> ORGANISM: Staphylococcus epidermis

<400> SEQUENCE: 18

| | | | | | |
|---|---|---|---|---|---|
| tacatgcaag | tcgagcgaac | agacgaggag | cttgctcctc | tgacgttagc | ggcggacggg | 60 |
| tgagtaacac | gtggataacc | tacctataag | actgggataa | cttcgggaaa | ccggagctaa | 120 |
| taccggataa | tatattgaac | cgcatggttc | aatagtgaaa | gacggttttg | ctgtcactta | 180 |
| tagatggatc | cgcgccgcat | tagctagttg | gtaaggtaac | ggcttaccaa | ggcaacgatg | 240 |
| cgtagccgac | ctgagagggt | gatcggccac | actggaactg | agacacggtc | cagactccta | 300 |
| cgggaggcag | cagtagggaa | tcttccgcaa | tgggcgaaag | cctgacggag | caacgccgcg | 360 |
| tgagtgatga | aggtcttcgg | atcgtaaaac | tctgttatta | gggaagaaca | aatgtgtaag | 420 |
| taactatgca | cgtcttgacg | gtacctaatc | agaaagccac | ggctaactac | gtgccagcag | 480 |
| ccgcggtaat | acgtaggtgg | caagcgttat | ccggaattat | tgggcgtaaa | gcgcgcgtag | 540 |
| gcggttttt | aagtctgatg | tgaaagccca | cggctcaacc | gtggaaggtc | attggaaact | 600 |
| ggaaaacttg | agtgcagaag | aagaaagtgg | aattccatgt | gtagcggtga | aatgcgcaga | 660 |
| aatatgagg | aacaccagtg | gcgaaggcga | ctttctggtc | tgtaactgac | gctgatgtgc | 720 |
| gaaagcgtgg | ggatcaaaca | ggattaaata | ccctggtagt | ccacgccgta | aacgatgaat | 780 |
| gctaagtggt | aggggtttc | cgccccttaa | tgctgcagct | aacgcattaa | gcactccgcc | 840 |
| tggggagtac | gaccgcaagg | ttgaaactca | aaggaattga | cggggacccg | cacaagcggt | 900 |
| ggagcatgtg | gtttaattcg | aagcaacgcg | aagaaccta | ccaaatcttg | acatcctctg | 960 |
| accctctag | agatagagtt | ttccccttcg | ggggacagag | tgacaggtgg | tgcatggttg | 1020 |
| tcgtcagctc | gtgtcgtgag | atgttgggtt | aagtcccgca | acgagcgcaa | cccttaagct | 1080 |
| tagttgccat | cattaagttg | ggcactctaa | gttgactgcc | ggtgacaaac | cggaggaagg | 1140 |
| tggggatgac | gtcaaatcat | catgcccctt | atgatttggg | ctacacacgt | gctacaatgg | 1200 |
| acaatacaaa | gggcagcgaa | accgcgaggt | caagcaaatc | ccataaagtt | gttctcagtt | 1260 |
| cggattgtag | tctgcaactc | gactatatga | agctggaatc | gctagtaatc | gtagatcagc | 1320 |
| atgctacggt | gaatacgttc | ccgggtcttg | tacacaccgc | ccgtcacacc | acgagagttt | 1380 |
| gtaacacccg | aagccggtgg | agtaaccatt | ggagcta | | | 1417 |

<210> SEQ ID NO 19
<211> LENGTH: 1427
<212> TYPE: DNA
<213> ORGANISM: Enterococcus sp.

<400> SEQUENCE: 19

| | | | | | |
|---|---|---|---|---|---|
| tgcagtcgaa | cgcttttct | ttcaccggag | cttgctccac | cgaaagaaaa | agagtggcga | 60 |
| acgggtgagt | aacacgtggg | taacctgccc | atcagaaggg | gataacactt | ggaaacaggt | 120 |
| gctaataccg | tataacacta | ttttccgcat | ggaagaaagt | tgaaaggcgc | ttttgcgtca | 180 |
| ctgatggatg | gacccgcggt | gcattagcta | gttggtgagg | taacggctca | ccaaggcaac | 240 |
| gatgcatagc | cgacctgaga | gggtgatcgg | ccacactggg | actgagacac | ggcccagact | 300 |
| cctacgggag | gcagcagtag | ggaatcttcg | gcaatgacg | aaagtctgac | cgagcaacgc | 360 |
| cgcgtgagtg | aagaaggttt | tcggatcgta | aaactctgtt | gttagagaag | aacaaggatg | 420 |

```
agagtaaaat gttcatccct tgacggtatc taaccagaaa gccacggcta actacgtgcc      480
agcagccgcg gtaatacgta ggtggcaagc gttgtccgga tttattgggc gtaaagcgag      540
cgcaggcggt ttcttaagtc tgatgtgaaa gcccccggct caaccgggga gggtcattgg      600
aaactgggag acttgagtgc agaagaggag agtggaattc catgtgtagc ggtgaaatgc      660
gtagatatat ggaggaacac cagtggcgaa ggcggctctc tggtctgtaa ctgacgctga      720
ggctcgaaag cgtggggagc gaacaggatt agataccctg gtagtccacg ccgtaaacga      780
tgagtgctaa gtgttggagg gtttccgccc ttcagtgctg cagcaaacgc attaagcact      840
ccgcctgggg agtacgaccg caaggttgaa actcaaagga attgacgggg gcccgcacaa      900
gcggtggagc atgtggttta attcgaagca acgcgaagaa ccttaccagg tcttgacatc      960
ctttgaccac tctagagata gagcttcccc ttcgggggca aagtgacagg tggtgcatgg     1020
ttgtcgtcag ctcgtgtcgt gagatgttgg gttaagtccc gcaacgagcg caacccttat     1080
tgttagttgc catcatttag ttgggcactc tagcgagact gccggtgaca aaccggagga     1140
aggtggggat gacgtcaaat catcatgccc cttatgacct gggctacaca cgtgctacaa     1200
tgggaagtac aacgagttgc gaagtcgcga ggctaagcta atctcttaaa gcttctctca     1260
gttcggattg taggctgcaa ctcgcctaca tgaagccgga atcgctagta atcgcggatc     1320
agcacgccgc ggtgaatacg ttcccgggcc ttgtacacac cgcccgtcac accacgagag     1380
tttgtaacac ccgaagtcgg tgaggtaacc tttttggagc cagccgc                   1427
```